(12) United States Patent
Kim et al.

(10) Patent No.: US 12,331,120 B2
(45) Date of Patent: Jun. 17, 2025

(54) ANTIBODIES AGAINST PROGRAMMED DEATH-LIGAND 1 AND USES THEREOF

(71) Applicant: SCRIPPS KOREA ANTIBODY INSTITUTE, Gangwon-do (KR)

(72) Inventors: Dae Hee Kim, Seoul (KR); Eung-Suk Lee, Gwangwon-do (KR); Min Jung Kim, Gangwon-do (KR); Nara Tae, Gangwon-do (KR); Jong Rip Choi, Gangwon-do (KR)

(73) Assignee: SCRIPPS KOREA ANTIBODY INSTITUTE, Gangwon-Do (KR)

( * ) Notice: Subject to any disclaimer, the term of this patent is extended or adjusted under 35 U.S.C. 154(b) by 937 days.

(21) Appl. No.: 17/441,914

(22) PCT Filed: Apr. 9, 2020

(86) PCT No.: PCT/KR2020/004854
§ 371 (c)(1),
(2) Date: Sep. 22, 2021

(87) PCT Pub. No.: WO2020/209645
PCT Pub. Date: Oct. 15, 2020

(65) Prior Publication Data
US 2022/0195049 A1 Jun. 23, 2022

(30) Foreign Application Priority Data
Apr. 11, 2019 (KR) .......... 10-2019-0042501

(51) Int. Cl.
*C07K 16/28* (2006.01)
*A61K 39/395* (2006.01)
(Continued)

(52) U.S. Cl.
CPC ...... *C07K 16/2827* (2013.01); *A61K 39/3955* (2013.01); *A61K 47/6849* (2017.08);
(Continued)

(58) Field of Classification Search
None
See application file for complete search history.

(56) References Cited

U.S. PATENT DOCUMENTS

| 8,715,743 B2 | 5/2014 | Sutkowski et al. |
| 2017/0319690 A1 | 11/2017 | Wang et al. |

FOREIGN PATENT DOCUMENTS

| CN | 108456251 A | 8/2018 |
| CN | 108699146 A | 10/2018 |

(Continued)

OTHER PUBLICATIONS

MacCallum et al., Antibody-antigen interactions: contact analysis and binding site topography, J. Mol. Biol. 262:732-745, 1996.*

(Continued)

*Primary Examiner* — Claire Kaufman
(74) *Attorney, Agent, or Firm* — HULTQUIST, PLLC; Steven J. Hultquist

(57) ABSTRACT

Disclosed are an antibody to programmed death-ligand 1 (PD-L1) or an antigen-binding fragment thereof, a nucleic acid encoding the same, a vector including the nucleic acid, a cell transfected with the vector, a method of producing the antibody or the antigen-binding fragment thereof, a composition for preventing or treating cancer including the same, and a composition for combination therapy for preventing or treating cancer including the same.

11 Claims, 11 Drawing Sheets
Specification includes a Sequence Listing.

(51) Int. Cl.
| | |
|---|---|
| A61K 47/68 | (2017.01) |
| A61P 35/00 | (2006.01) |
| C12N 5/10 | (2006.01) |
| C12N 15/10 | (2006.01) |
| A61K 39/00 | (2006.01) |

(52) U.S. Cl.
CPC ........ *A61P 35/00* (2018.01); *A61K 2039/505* (2013.01); *A61K 2039/507* (2013.01); *C07K 2317/31* (2013.01); *C07K 2317/33* (2013.01); *C07K 2317/565* (2013.01); *C07K 2317/76* (2013.01)

(56) References Cited

FOREIGN PATENT DOCUMENTS

| EP | 3954706 A1 | 2/2022 |
|---|---|---|
| JP | 2018508475 A | 3/2018 |
| KR | 1020170023102 A | 3/2017 |
| KR | 1020170102167 A | 9/2017 |
| KR | 1020180016321 A | 2/2018 |
| KR | 1020190078771 A | 7/2019 |
| RU | 2306320 C2 | 9/2007 |
| RU | 2636023 C2 | 11/2017 |
| RU | 2701797 C2 | 10/2019 |
| WO | WO2016061142 A1 | 4/2016 |
| WO | 2016111646 A1 | 7/2016 |
| WO | 2018195226 A1 | 10/2018 |

OTHER PUBLICATIONS

Chen et al., Enhancement and destruction of antibody function by somatic mutation: unequal occurrence is controlled by V gene combinatorial associations, EMBO J. 14(12):2784-2794, 1995.*
Lamminmaki et al., Crystal structure of a recombinant anti-estradiol Fab fragment in complex with 17B-estradiol, J. Biol. Chem. 276:36687, 2001.*
Office Action Issued in counterpart Japanese Patent Application No. 2021-560053 on Nov. 11, 2022.
English Translation of Office Action Issued in counterpart Japanese Patent Application No. 2021-560053 on Nov. 11, 2022.
EESR Issued on Oct. 11, 2023 in European Patent Applicaiton No. 20787913.1 (Extended European Search).
Office Action issued in European Patent Application 20787913.1 on Jun. 20, 2023.
Powles, T., et al., "MPDL3280A (anti-PD-L1) treatment leads to clinical activity in metastatic bladder cancer", Nature, 2014, doi: 10.1038/Inature13904, vol. 515, Publisher: Macmillan Publishers Limited.
Brown, M., et al., "Tolerance of single, but not multiple, amino acid replacements in antibody VH CDE 2: a means of minimizing B cell wastage from somatic hypermutation", J Immunol., 1996, pp. 3285-3291, vol. 156, No. 9.
Nejadmoghaddam, M-R, et al., "Antibody-Drug Conjugates: Possibilities and Challenges", Avicenna Journal of Medical Biotechnology, 2019, pp. 3, vol. 11, No. 1.
Perez, H.L., et al., "Antibody-drug conjugates: current status and future directions", Drug Discovery Today, 2014, pp. 869-881, vol. 19, No. 7, Publisher: Elsevier.
Rudikoff, S., et al., "Single amino acid substitutions altering antigen-binding specificity", Proc. Natl. Acad. Sci. USA: Immunology, 1982, pp. 1979-1983, vol. 79.
Sharpe, A.H., et al., "The functin of programmed cell death 1 and its ligands in regulating autoimmunity and infection", Nature Immunology, 2007, pp. 239-245, vol. 8, No. 3.
Tol, J., et al., "Chemotherapy, Bevacizumab, and Cetuximab in Metastatic Colorectal Cancer", The New England Journal of Medicine, 2009, pp. 563-572, vol. 360, No. 6.
Mao, S., et al., "Phage-display library selection of high-affinity human single-chain antibodies to tumor-associated carbohydrate antigens sialyl Lewisx and Lewisx", Proc. Natl. Acad. Sci. USA, 1999, pp. 6953-6958, vol. 96, Publisher: Medical Sciences.
Yang, H., et al., "Construction of a Large Synthetic Human scFv Library with Six Diversified CDRs and High Functional Diversity", Mol. Cells, Feb. 28, 2009, pp. 225-235, vol. 27, Publisher: Springer.
AU Office Action issued on Feb. 6, 2024 for Australian patent application No. 2020271467.
CN Office Action issued on Nov. 2, 2023 for Chinese patent application No. 202080028102.8.
CN Office Action issued on Nov. 2, 2023 for Chinese patent application No. 2020800288102.8, English Translation.
CN Search Report issued on Nov. 1, 2023 for Chinese patent application No. 202080028102.8.
Yang, X., et al., "Anti-PD-1/PD-L1 antibodies in tumor treatment", J Surg Concepts Pract, 2018, pp. 227-239, vol. 23, No. 3.
Yang, X., et al., "Anti-PD-1/PD-L1 antibodies in tumor treatment", J Surg Concepts Pract, 2018, pp. 227-239, vol. 23, No. 3, English Translation.

* cited by examiner

[Fig. 1]
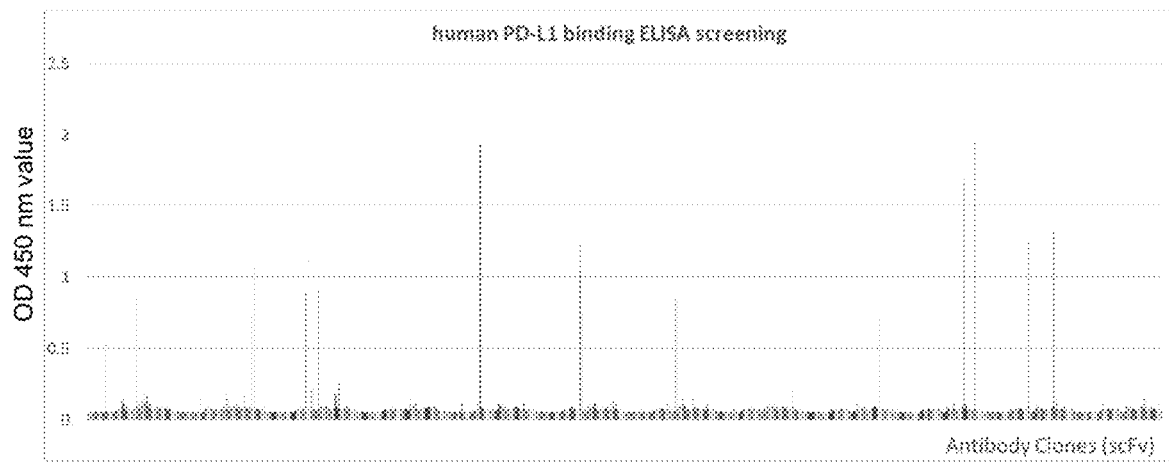
[Fig. 2]
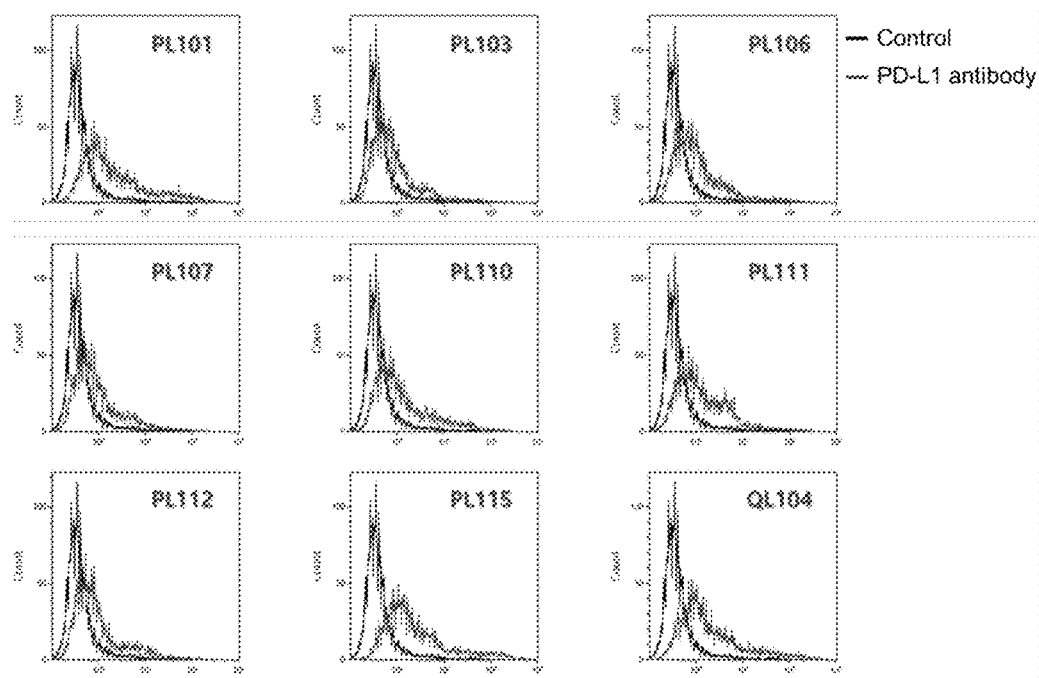

[Fig. 3]
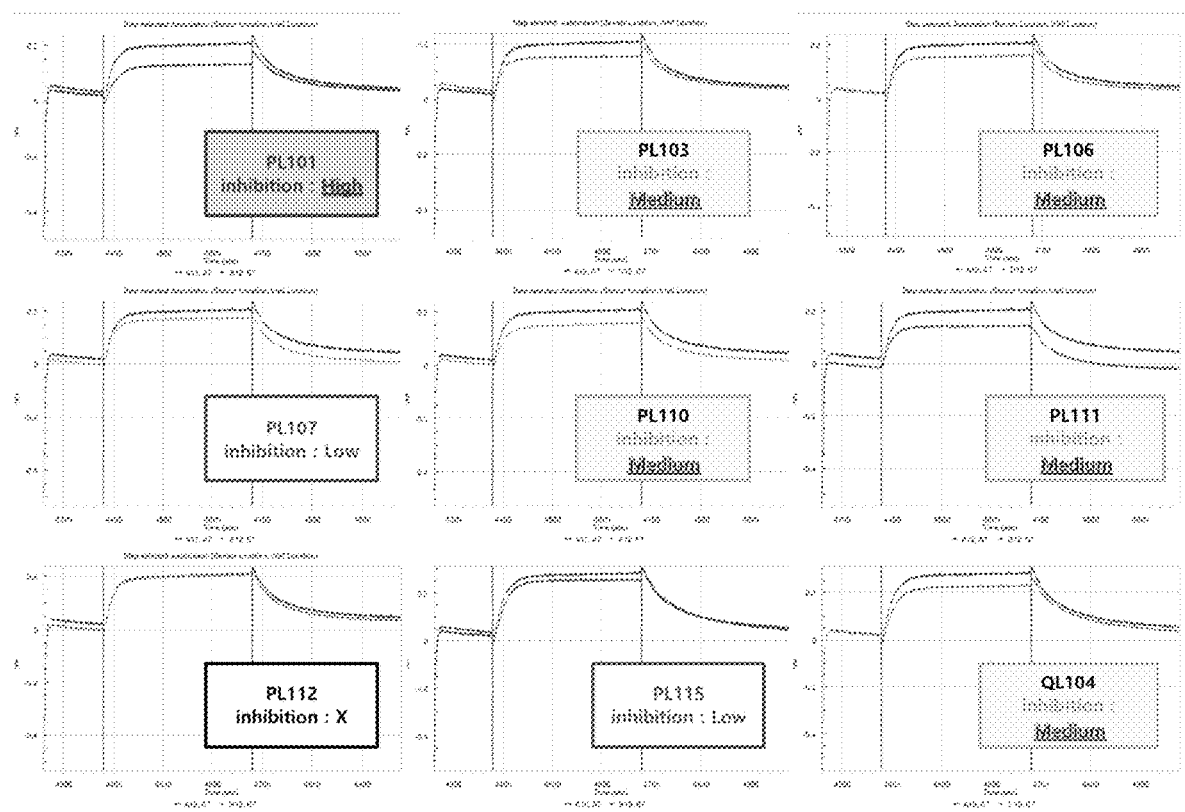

[Fig. 4]
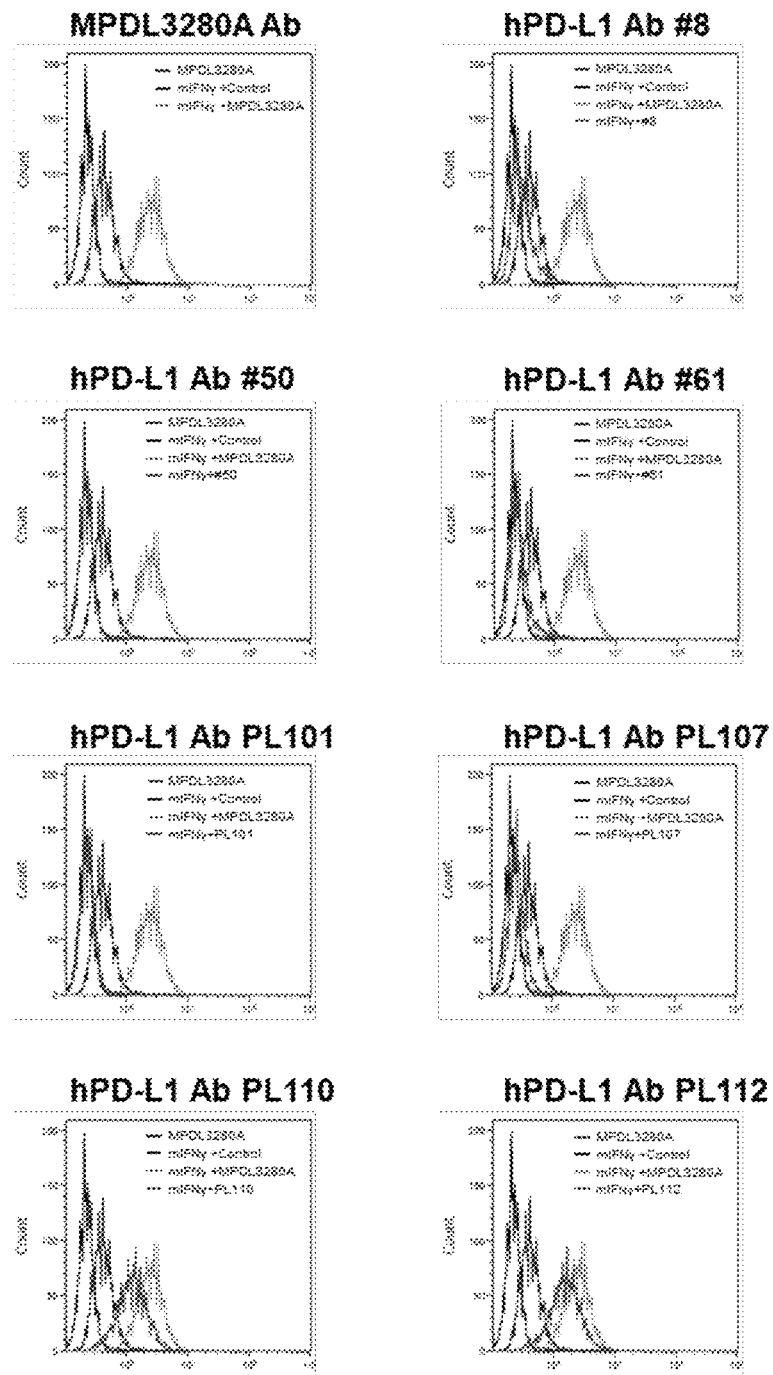

[Fig. 5]
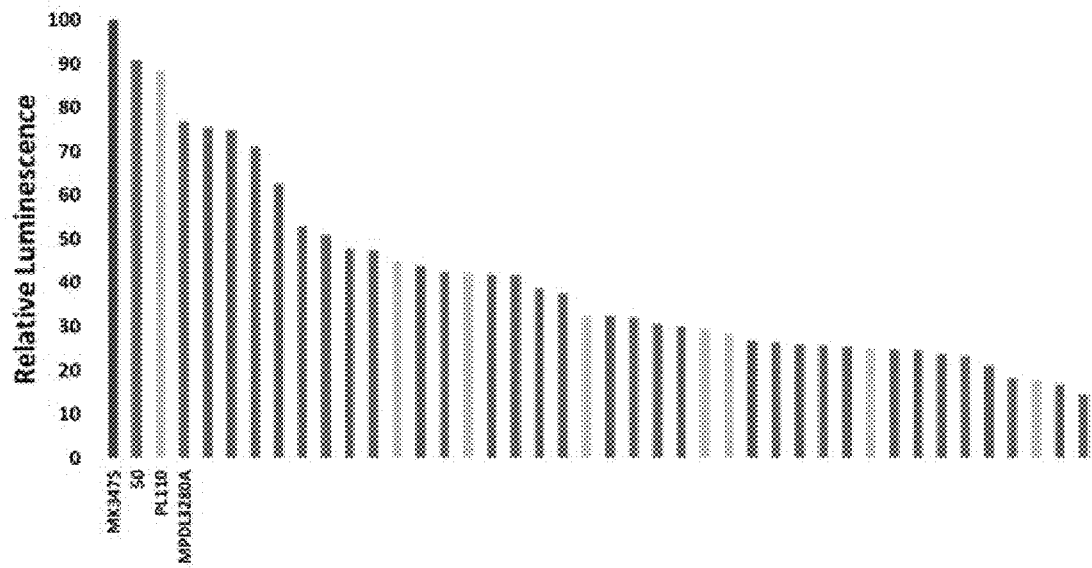
[Fig. 6]
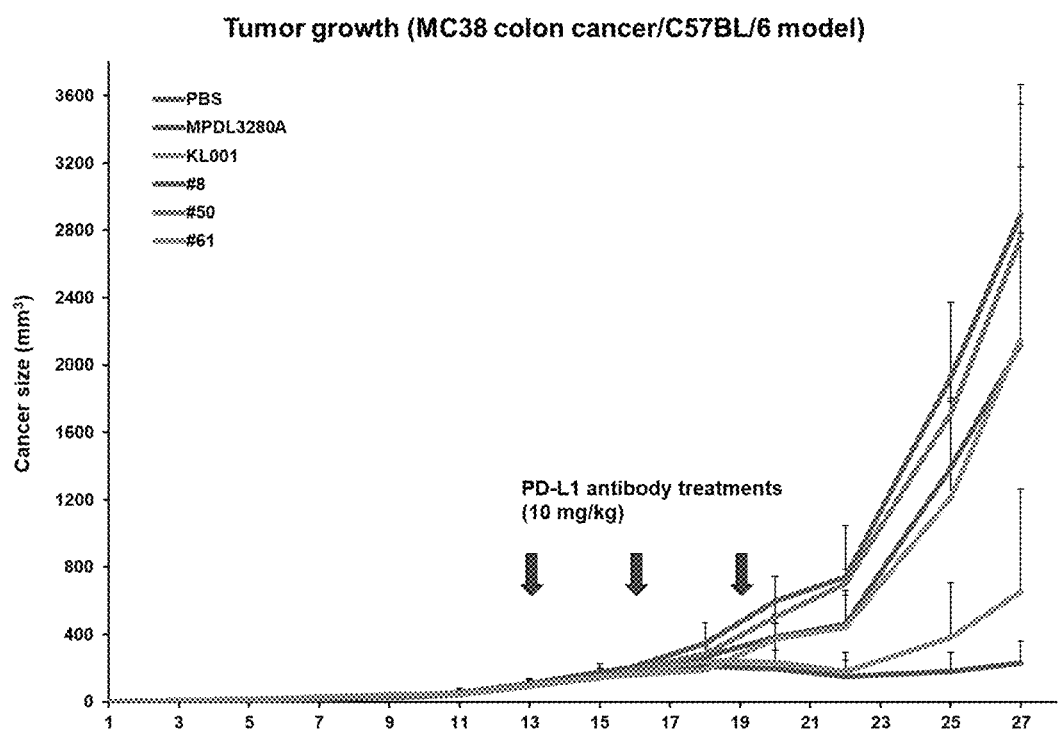

[Fig. 7]
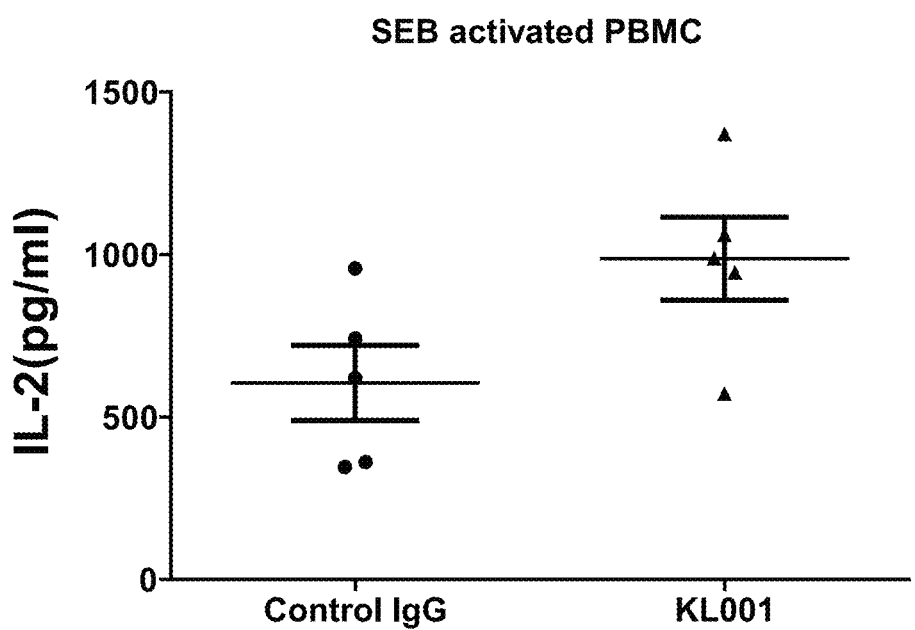
[Fig. 8]
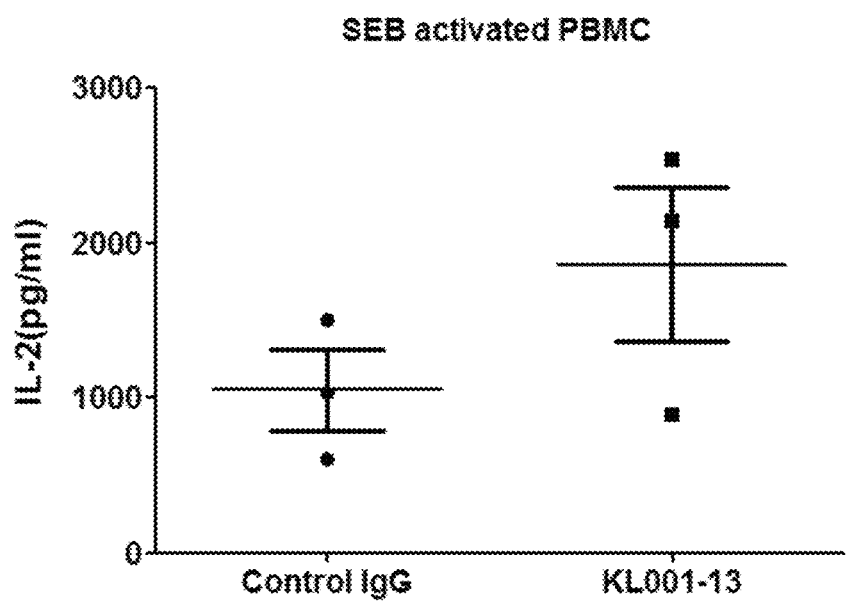

【Fig. 9】
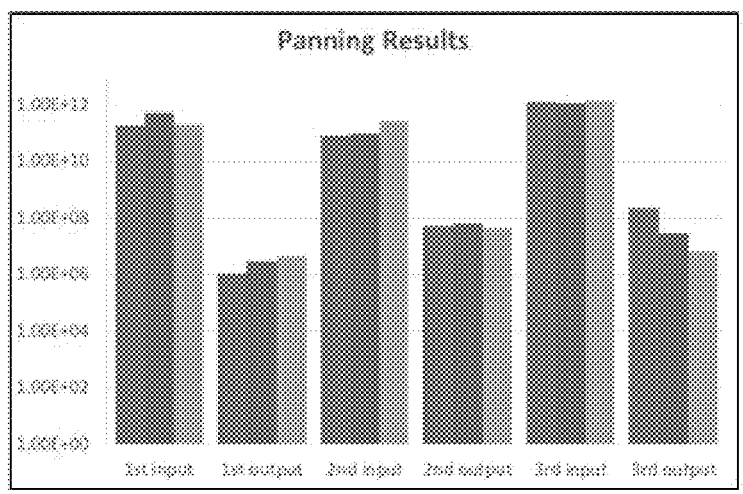
【Fig. 10】
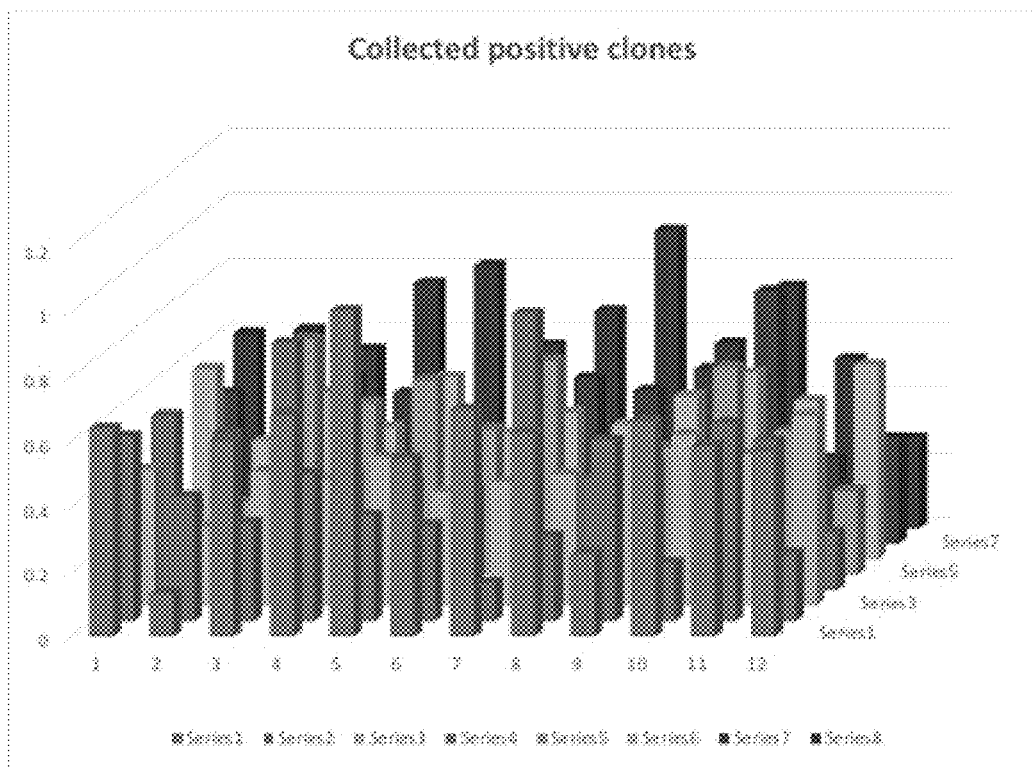

[Fig. 11]
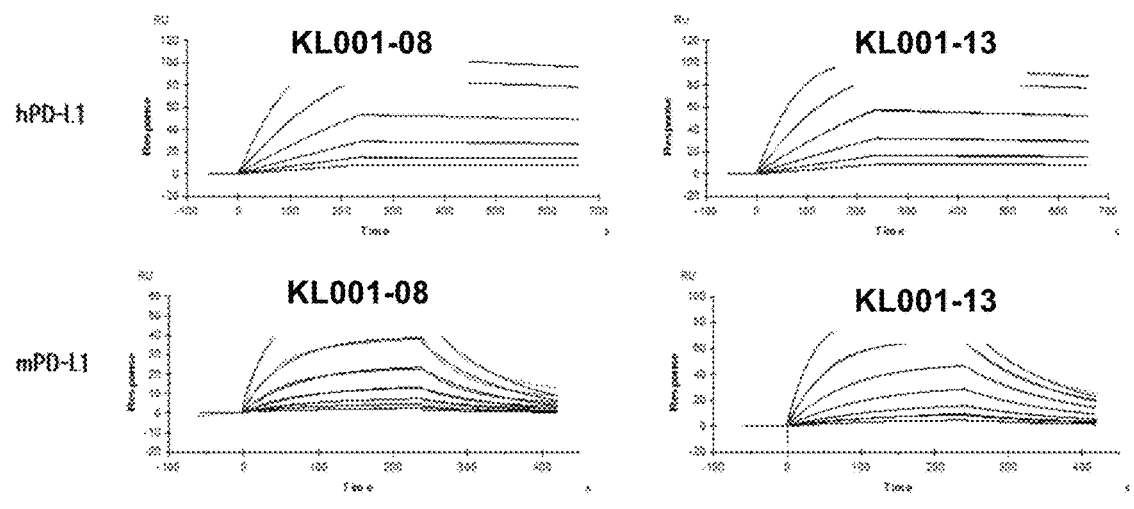

[Fig. 12]
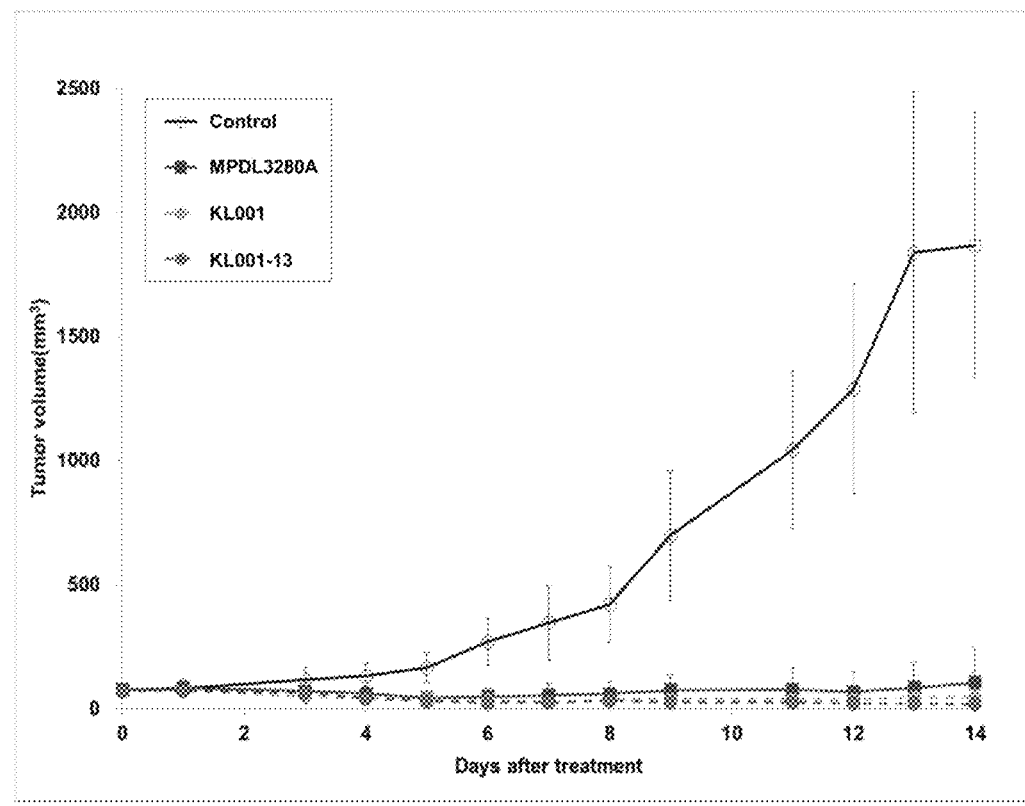
[Fig. 13]
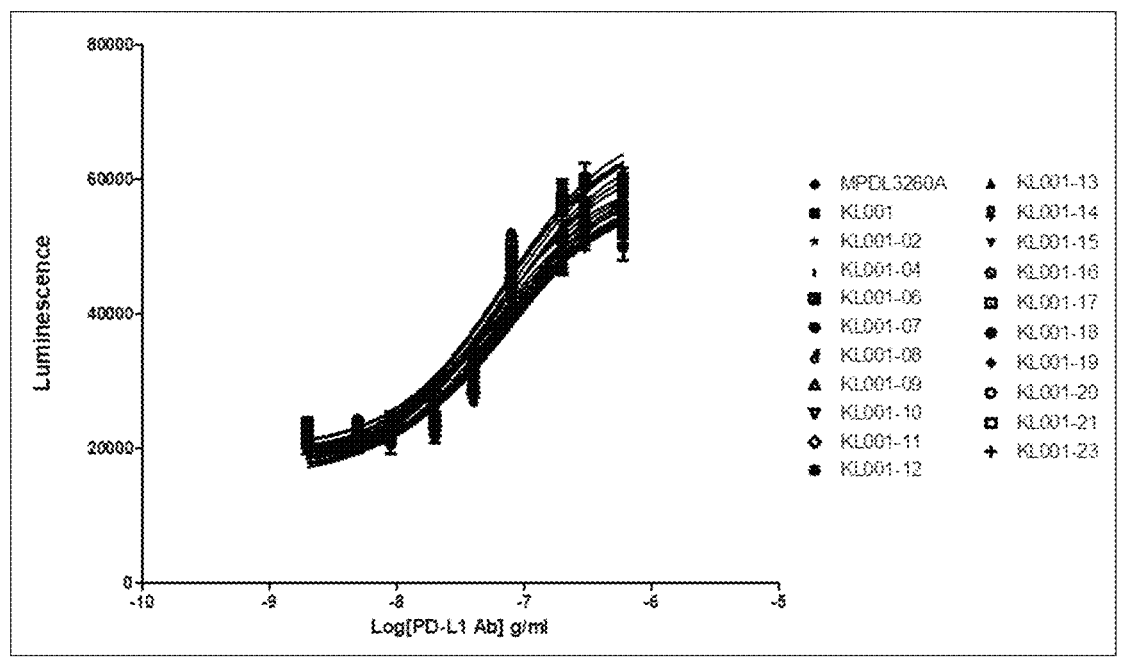

[Fig. 14]
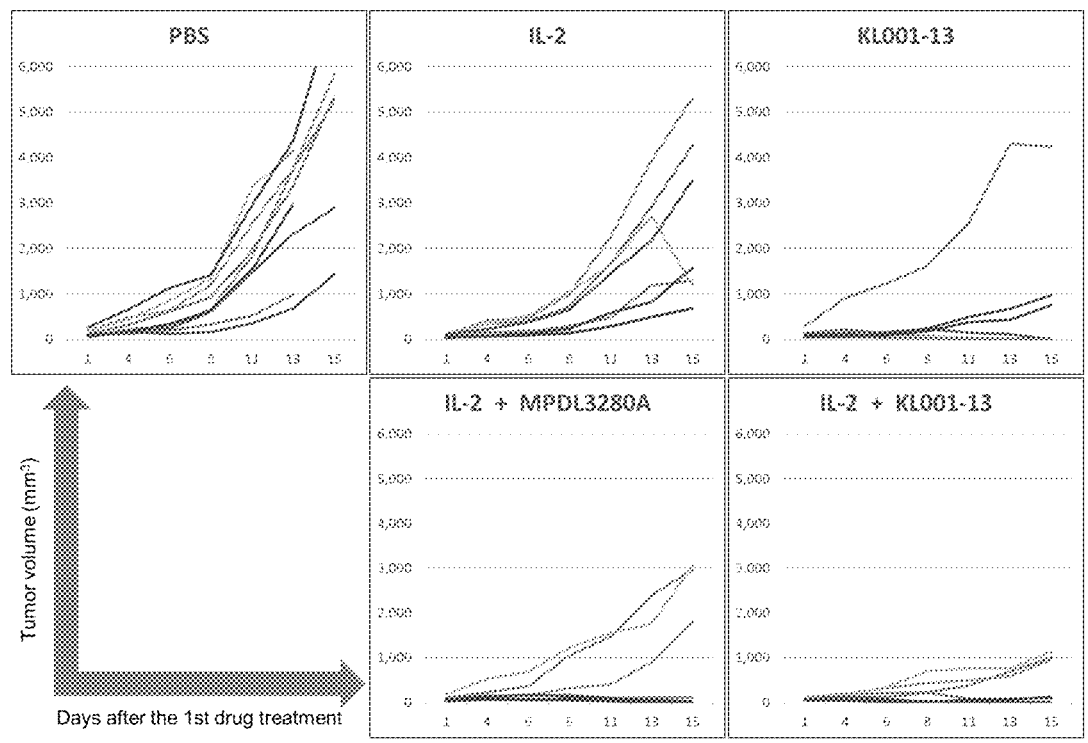
[Fig. 15]
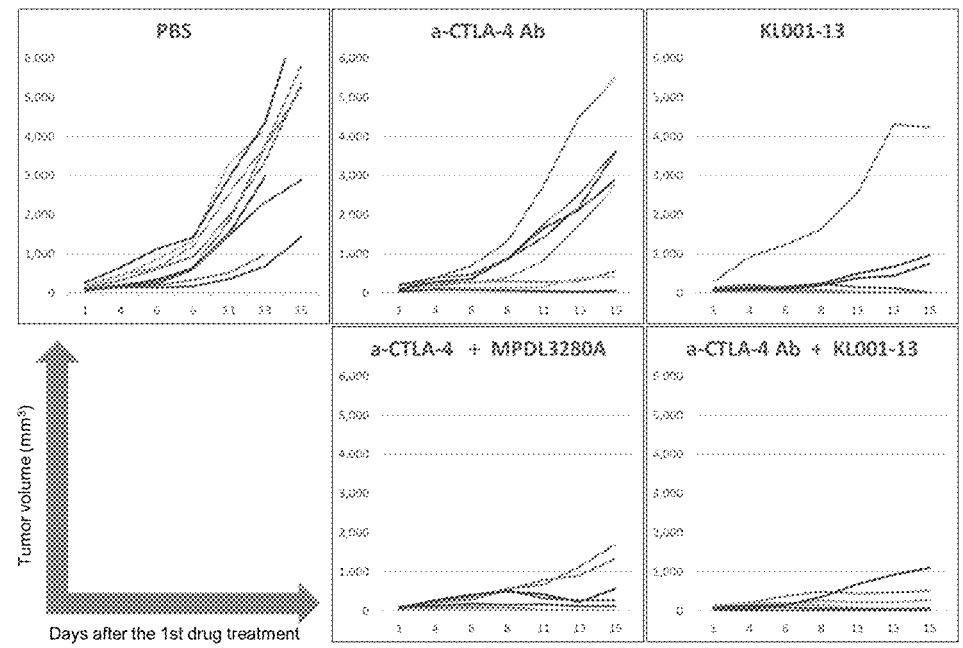

[Fig. 16]

(A) Heavy chain variable region (SEQ ID NO: 87)

```
                            CDR1                                  CDR2
QVQLVESGAEVKKPGSSVKVSCKASGGTFSSYAISWVRQAPGQGLEWMGRIIPILGIANYAQKFQGRV
                    IMGT: GGTFSSYA (SEQ ID NO: 1)     IMGT:  IIPILGIA (SEQ ID NO: 2)
                    Kabat:         SYAIS (SEQ ID NO: 22)  Kabat: RIIPILGIANYA (SEQ ID NO: 23)
                    Chothia : GGTFSSY (SEQ ID NO: 29)   Chothia:   IPILGI (SEQ ID NO: 30)

CDR3
TVTADKSTSTAYMELSSLRSEDTAVYYCARSGYGYAYGSFDYWGQGTLVTVSS
                    IMGT:   ARSGYGYAYGSFDY (SEQ ID NO: 11)
                    Kabat:     SGYGYAYGSFDY (SEQ ID NO: 25)
                    Chothia :  SGYGYAYGSFDY (SEQ ID NO: 25)
```

(B) Light chain variable region (SEQ ID NO: 88)

```
                            CDR1                              CDR2
QLVLTQPPSVSGAPGQTVTISCTGQTIGAGYDVHWYQQLPGAAPKLLIYGNLNRPSGVPDRFSGSKS
                    IMGT:  GQTIGAGYD (SEQ ID NO: 13)     IMGT:  GNL (SEQ ID NO: 6)
                    Kabat: TGQTIGAGYDVH (SEQ ID NO: 27) Kabat: GNLNRPS (SEQ ID NO: 28)
                    Chothia: TGQTIGAGYDVH (SEQ ID NO: 27) Chothia : GNLNRPS (SEQ ID NO: 28)

CDR3
GTSASLAITDLQAEDEADYYCQSYDSRLGVVFGGGTKLTVL
                    IMGT:   QSYDSRLGVV (SEQ ID NO: 7)
                    Kabat:  QSYDSRLGVV (SEQ ID NO: 7)
                    Chothia: QSYDSRLGVV (SEQ ID NO: 7)
```

[Fig. 17]
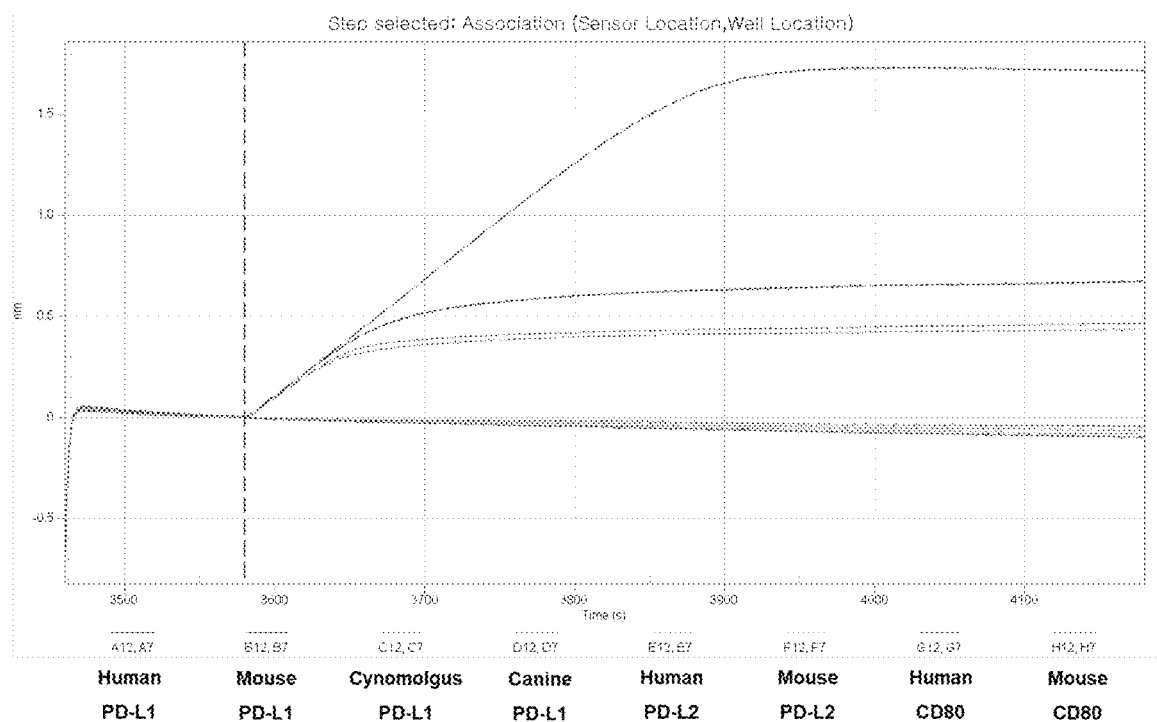

```
SEQUENCE LISTING

<160> NUMBER OF SEQ ID NOS: 88

<210> SEQ ID NO 1
<211> LENGTH: 8
<212> TYPE: PRT
<213> ORGANISM: Artificial Sequence
<220> FEATURE:
<223> OTHER INFORMATION: Synthetic Construct

<400> SEQUENCE: 1

Gly Gly Thr Phe Ser Ser Tyr Ala
1               5
```

<210> SEQ ID NO 2
<211> LENGTH: 8
<212> TYPE: PRT
<213> ORGANISM: Artificial Sequence
<220> FEATURE:
<223> OTHER INFORMATION: Synthetic Construct

<400> SEQUENCE: 2

Ile Ile Pro Ile Leu Gly Ile Ala
1               5

<210> SEQ ID NO 3
<211> LENGTH: 14
<212> TYPE: PRT
<213> ORGANISM: Artificial Sequence
<220> FEATURE:
<223> OTHER INFORMATION: Synthetic Construct

<400> SEQUENCE: 3

Ala Arg Ser Gly Tyr Ser Tyr Ala Tyr Gly Ser Phe Asp Tyr
1               5                   10

<210> SEQ ID NO 4
<211> LENGTH: 121
<212> TYPE: PRT
<213> ORGANISM: Artificial Sequence
<220> FEATURE:
<223> OTHER INFORMATION: Synthetic Construct

<400> SEQUENCE: 4

Gln Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Val Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Tyr Ser Tyr Ala Tyr Gly Ser Phe Asp Tyr Trp Gly
            100                 105                 110

Gln Gly Thr Leu Val Thr Val Ser Ser
        115                 120

<210> SEQ ID NO 5
<211> LENGTH: 9
<212> TYPE: PRT
<213> ORGANISM: Artificial Sequence
<220> FEATURE:
<223> OTHER INFORMATION: Synthetic Construct

<400> SEQUENCE: 5

Gly Pro Thr Ile Gly Ala Gly Tyr Asp
1               5

<210> SEQ ID NO 6

<400> SEQUENCE: 6

000

<210> SEQ ID NO 7
<211> LENGTH: 10
<212> TYPE: PRT
<213> ORGANISM: Artificial Sequence
<220> FEATURE:
<223> OTHER INFORMATION: Synthetic Construct

<400> SEQUENCE: 7

```
Gln Ser Tyr Asp Ser Arg Leu Gly Val Val
1               5                   10
```

<210> SEQ ID NO 8
<211> LENGTH: 108
<212> TYPE: PRT
<213> ORGANISM: Artificial Sequence
<220> FEATURE:
<223> OTHER INFORMATION: Synthetic Construct

<400> SEQUENCE: 8

```
Gln Leu Val Leu Thr Gln Pro Pro Ser Val Ser Gly Ala Pro Gly Gln
1               5                   10                  15

Thr Val Thr Ile Ser Cys Thr Gly Pro Thr Ile Gly Ala Gly Tyr Asp
            20                  25                  30

Val His Trp Tyr Gln Gln Leu Pro Gly Ala Ala Pro Lys Leu Leu Ile
        35                  40                  45

Tyr Gly Asn Leu Asn Arg Pro Ser Gly Val Pro Asp Arg Phe Ser Gly
    50                  55                  60

Ser Lys Ser Gly Thr Ser Ala Ser Leu Ala Ile Thr Asp Leu Gln Ala
65                  70                  75                  80

Glu Asp Glu Ala Asp Tyr Tyr Cys Gln Ser Tyr Asp Ser Arg Leu Gly
                85                  90                  95

Val Val Phe Gly Gly Gly Thr Lys Leu Thr Val Leu
            100                 105
```

<210> SEQ ID NO 9
<211> LENGTH: 451
<212> TYPE: PRT
<213> ORGANISM: Artificial Sequence
<220> FEATURE:
<223> OTHER INFORMATION: Synthetic Construct

<400> SEQUENCE: 9

```
Gln Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Val Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Tyr Ser Tyr Ala Tyr Gly Ser Phe Asp Tyr Trp Gly
                100                 105                 110

Gln Gly Thr Leu Val Thr Val Ser Ser Ala Ser Thr Lys Gly Pro Ser
            115                 120                 125
```

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 10
<211> LENGTH: 215
<212> TYPE: PRT
<213> ORGANISM: Artificial Sequence
<220> FEATURE:
<223> OTHER INFORMATION: Synthetic Construct

<400> SEQUENCE: 10

Gln Leu Val Leu Thr Gln Pro Pro Ser Val Ser Gly Ala Pro Gly Gln
1               5                   10                  15

Thr Val Thr Ile Ser Cys Thr Gly Pro Thr Ile Gly Ala Gly Tyr Asp
            20                  25                  30

```
Val His Trp Tyr Gln Gln Leu Pro Gly Ala Ala Pro Lys Leu Leu Ile
         35                  40                  45

Tyr Gly Asn Leu Asn Arg Pro Ser Gly Val Pro Asp Arg Phe Ser Gly
     50                  55                  60

Ser Lys Ser Gly Thr Ser Ala Ser Leu Ala Ile Thr Asp Leu Gln Ala
 65                  70                  75                  80

Glu Asp Glu Ala Asp Tyr Tyr Cys Gln Ser Tyr Asp Ser Arg Leu Gly
                 85                  90                  95

Val Val Phe Gly Gly Gly Thr Lys Leu Thr Val Leu Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 11
<211> LENGTH: 14
<212> TYPE: PRT
<213> ORGANISM: Artificial Sequence
<220> FEATURE:
<223> OTHER INFORMATION: Synthetic Construct

<400> SEQUENCE: 11

Ala Arg Ser Gly Tyr Gly Tyr Ala Tyr Gly Ser Phe Asp Tyr
1               5                   10

<210> SEQ ID NO 12
<211> LENGTH: 121
<212> TYPE: PRT
<213> ORGANISM: Artificial Sequence
<220> FEATURE:
<223> OTHER INFORMATION: Synthetic Construct

<400> SEQUENCE: 12

Gln Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Val Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Tyr Gly Tyr Ala Tyr Gly Ser Phe Asp Tyr Trp Gly
            100                 105                 110
```

Gln Gly Thr Leu Val Thr Val Ser Ser
        115                 120

<210> SEQ ID NO 13
<211> LENGTH: 9
<212> TYPE: PRT
<213> ORGANISM: Artificial Sequence
<220> FEATURE:
<223> OTHER INFORMATION: Synthetic Construct

<400> SEQUENCE: 13

Gly Gln Thr Ile Gly Ala Gly Tyr Asp
1               5

<210> SEQ ID NO 14
<211> LENGTH: 108
<212> TYPE: PRT
<213> ORGANISM: Artificial Sequence
<220> FEATURE:
<223> OTHER INFORMATION: Synthetic Construct

<400> SEQUENCE: 14

Gln Leu Val Leu Thr Gln Pro Pro Ser Val Ser Gly Ala Pro Gly Gln
1               5                   10                  15

Thr Val Thr Ile Ser Cys Thr Gly Gln Thr Ile Gly Ala Gly Tyr Asp
            20                  25                  30

Val His Trp Tyr Gln Gln Leu Pro Gly Ala Ala Pro Lys Leu Leu Ile
        35                  40                  45

Tyr Gly Asn Leu Asn Arg Pro Ser Gly Val Pro Asp Arg Phe Ser Gly
    50                  55                  60

Ser Lys Ser Gly Thr Ser Ala Ser Leu Ala Ile Thr Asp Leu Gln Ala
65                  70                  75                  80

Glu Asp Glu Ala Asp Tyr Tyr Cys Gln Ser Tyr Asp Ser Arg Leu Gly
                85                  90                  95

Val Val Phe Gly Gly Gly Thr Lys Leu Thr Val Leu
            100                 105

<210> SEQ ID NO 15
<211> LENGTH: 451
<212> TYPE: PRT
<213> ORGANISM: Artificial Sequence
<220> FEATURE:
<223> OTHER INFORMATION: Synthetic Construct

<400> SEQUENCE: 15

Gln Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Arg Ile Ile Pro Ile Leu Gly Ile Ala Asn Tyr Ala Gln Lys Phe
    50                  55                  60

Gln Gly Arg Val Thr Val Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Tyr Gly Tyr Ala Tyr Gly Ser Phe Asp Tyr Trp Gly
            100                 105                 110

```
Gln Gly Thr Leu Val Thr Val Ser Ser Ala Ser Thr Lys Gly Pro Ser
            115                 120                 125

Val Phe Pro Leu Ala Pro Ser Ser Lys Ser Thr Ser Gly Gly Thr Ala
        130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
            290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 16
<211> LENGTH: 215
<212> TYPE: PRT
<213> ORGANISM: Artificial Sequence
<220> FEATURE:
<223> OTHER INFORMATION: Synthetic Construct

<400> SEQUENCE: 16

Gln Leu Val Leu Thr Gln Pro Pro Ser Val Ser Gly Ala Pro Gly Gln
1               5                   10                  15
```

Thr Val Thr Ile Ser Cys Thr Gly Gln Thr Ile Ala Gly Tyr Asp
            20                  25                  30

Val His Trp Tyr Gln Gln Leu Pro Gly Ala Ala Pro Lys Leu Leu Ile
        35                  40                  45

Tyr Gly Asn Leu Asn Arg Pro Ser Gly Val Pro Asp Arg Phe Ser Gly
    50                  55                  60

Ser Lys Ser Gly Thr Ser Ala Ser Leu Ala Ile Thr Asp Leu Gln Ala
65                  70                  75                  80

Glu Asp Glu Ala Asp Tyr Tyr Cys Gln Ser Tyr Asp Ser Arg Leu Gly
                85                  90                  95

Val Val Phe Gly Gly Gly Thr Lys Leu Thr Val Leu Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 17
<211> LENGTH: 448
<212> TYPE: PRT
<213> ORGANISM: Artificial Sequence
<220> FEATURE:
<223> OTHER INFORMATION: Synthetic Construct

<400> SEQUENCE: 17

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Ser
            20                  25                  30

Trp Ile His Trp Val Arg Gln Ala Pro Gly Lys Gly Leu Glu Trp Val
        35                  40                  45

Ala Trp Ile Ser Pro Tyr Gly Gly Ser Thr Tyr Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Arg His Trp Pro Gly Gly Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

```
Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
        180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
        210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 18
<211> LENGTH: 214
<212> TYPE: PRT
<213> ORGANISM: Artificial Sequence
<220> FEATURE:
<223> OTHER INFORMATION: Synthetic Construct

<400> SEQUENCE: 18

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80
```

```
Glu Asp Phe Ala Thr Tyr Tyr Cys Gln Gln Tyr Leu Tyr His Pro Ala
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
                180                 185                 190

Ala Cys Glu Val Thr His Gln Gly Leu Ser Ser Pro Val Thr Lys Ser
            195                 200                 205

Phe Asn Arg Gly Glu Cys
        210
```

<210> SEQ ID NO 19
<211> LENGTH: 450
<212> TYPE: PRT
<213> ORGANISM: Artificial Sequence
<220> FEATURE:
<223> OTHER INFORMATION: Synthetic Construct

<400> SEQUENCE: 19

```
Gln Val Gln Leu Val Gln Ser Gly Val Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Met Tyr Trp Val Arg Gln Ala Pro Gly Gln Gly Leu Glu Trp Met
        35                  40                  45

Gly Gly Ile Asn Pro Ser Asn Gly Gly Thr Asn Phe Asn Glu Lys Phe
    50                  55                  60

Lys Asn Arg Val Thr Leu Thr Thr Asp Ser Ser Thr Thr Thr Ala Tyr
65                  70                  75                  80

Met Glu Leu Lys Ser Leu Gln Phe Asp Asp Thr Ala Val Tyr Tyr Cys
                85                  90                  95

Ala Arg Arg Asp Tyr Arg Phe Asp Met Gly Phe Asp Tyr Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
            195                 200                 205

Pro Ser Asn Thr Lys Val Asp Lys Lys Val Glu Pro Lys Ser Cys Asp
        210                 215                 220
```

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
            245                 250                 255

Ser Arg Thr Pro Glu Val Thr Cys Val Val Val Asp Val Ser His Glu
        260                 265                 270

Asp Pro Glu Val Lys Phe Asn Trp Tyr Val Asp Gly Val Glu Val His
    275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
            325                 330                 335

Lys Thr Ile Ser Lys Ala Lys Gly Gln Pro Arg Glu Pro Gln Val Tyr
        340                 345                 350

Thr Leu Pro Pro Ser Arg Asp Glu Leu Thr Lys Asn Gln Val Ser Leu
    355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
    435                 440                 445

Gly Lys
450

<210> SEQ ID NO 20
<211> LENGTH: 218
<212> TYPE: PRT
<213> ORGANISM: Artificial Sequence
<220> FEATURE:
<223> OTHER INFORMATION: Synthetic Construct

<400> SEQUENCE: 20

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Lys Gly Val Ser Thr Ser
            20                  25                  30

Gly Tyr Ser Tyr Leu His Trp Tyr Gln Gln Lys Pro Gly Gln Ala Pro
        35                  40                  45

Arg Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Thr Ile Ser
65                  70                  75                  80

Ser Leu Glu Pro Glu Asp Phe Ala Val Tyr Tyr Cys Gln His Ser Arg
            85                  90                  95

Asp Leu Pro Leu Thr Phe Gly Gly Gly Thr Lys Val Glu Ile Lys Arg
        100                 105                 110

Thr Val Ala Ala Pro Ser Val Phe Ile Phe Pro Pro Ser Asp Glu Gln
    115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Gln Asp Ser Lys Asp Ser Thr
            165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
210                 215

<210> SEQ ID NO 21
<211> LENGTH: 214
<212> TYPE: PRT
<213> ORGANISM: Artificial Sequence
<220> FEATURE:
<223> OTHER INFORMATION: Synthetic Construct

<400> SEQUENCE: 21

Gln Leu Val Leu Thr Gln Pro Pro Ser Val Ser Gly Ala Pro Gly Gln
1               5                   10                  15

Thr Val Thr Ile Ser Cys Thr Gly Gln Thr Ile Gly Ala Gly Tyr Asp
            20                  25                  30

Val His Trp Tyr Gln Gln Leu Pro Gly Ala Ala Pro Lys Leu Leu Ile
        35                  40                  45

Tyr Gly Asn Leu Asn Arg Pro Ser Gly Val Pro Asp Arg Phe Ser Gly
    50                  55                  60

Ser Lys Ser Gly Thr Ser Ala Ser Leu Ala Ile Thr Asp Leu Gln Ala
65                  70                  75                  80

Glu Asp Glu Ala Asp Tyr Tyr Cys Gln Ser Tyr Asp Ser Arg Leu Gly
                85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser
    210

<210> SEQ ID NO 22
<211> LENGTH: 5
<212> TYPE: PRT
<213> ORGANISM: Artificial Sequence
<220> FEATURE:
<223> OTHER INFORMATION: Synthetic Construct

<400> SEQUENCE: 22

Ser Tyr Ala Ile Ser
1               5

<210> SEQ ID NO 23
<211> LENGTH: 12
<212> TYPE: PRT
<213> ORGANISM: Artificial Sequence
<220> FEATURE:
<223> OTHER INFORMATION: Synthetic Construct

<400> SEQUENCE: 23

Arg Ile Ile Pro Ile Leu Gly Ile Ala Asn Tyr Ala
1               5                   10

<210> SEQ ID NO 24
<211> LENGTH: 12
<212> TYPE: PRT
<213> ORGANISM: Artificial Sequence
<220> FEATURE:
<223> OTHER INFORMATION: Synthetic Construct

<400> SEQUENCE: 24

Ser Gly Tyr Ser Tyr Ala Tyr Gly Ser Phe Asp Tyr
1               5                   10

<210> SEQ ID NO 25
<211> LENGTH: 12
<212> TYPE: PRT
<213> ORGANISM: Artificial Sequence
<220> FEATURE:
<223> OTHER INFORMATION: Synthetic Construct

<400> SEQUENCE: 25

Ser Gly Tyr Gly Tyr Ala Tyr Gly Ser Phe Asp Tyr
1               5                   10

<210> SEQ ID NO 26
<211> LENGTH: 12
<212> TYPE: PRT
<213> ORGANISM: Artificial Sequence
<220> FEATURE:
<223> OTHER INFORMATION: Synthetic Construct

<400> SEQUENCE: 26

Thr Gly Pro Thr Ile Gly Ala Gly Tyr Asp Val His
1               5                   10

<210> SEQ ID NO 27
<211> LENGTH: 12
<212> TYPE: PRT
<213> ORGANISM: Artificial Sequence
<220> FEATURE:
<223> OTHER INFORMATION: Synthetic Construct

<400> SEQUENCE: 27

Thr Gly Gln Thr Ile Gly Ala Gly Tyr Asp Val His
1               5                   10

<210> SEQ ID NO 28
<211> LENGTH: 7
<212> TYPE: PRT
<213> ORGANISM: Artificial Sequence
<220> FEATURE:
<223> OTHER INFORMATION: Synthetic Construct

<400> SEQUENCE: 28

Gly Asn Leu Asn Arg Pro Ser
1               5

<210> SEQ ID NO 29
<211> LENGTH: 7
<212> TYPE: PRT
<213> ORGANISM: Artificial Sequence
<220> FEATURE:
<223> OTHER INFORMATION: Synthetic Construct

<400> SEQUENCE: 29

Gly Gly Thr Phe Ser Ser Tyr
1               5

<210> SEQ ID NO 30
<211> LENGTH: 6
<212> TYPE: PRT
<213> ORGANISM: Artificial Sequence
<220> FEATURE:
<223> OTHER INFORMATION: Synthetic Construct

<400> SEQUENCE: 30

Ile Pro Ile Leu Gly Ile
1               5

<210> SEQ ID NO 31
<211> LENGTH: 9
<212> TYPE: PRT
<213> ORGANISM: Artificial Sequence
<220> FEATURE:
<223> OTHER INFORMATION: Synthetic Construct

<400> SEQUENCE: 31

Gly Pro Thr Ile Gly Gln Gly Tyr Asp
1               5

<210> SEQ ID NO 32
<211> LENGTH: 9
<212> TYPE: PRT
<213> ORGANISM: Artificial Sequence
<220> FEATURE:
<223> OTHER INFORMATION: Synthetic Construct

<400> SEQUENCE: 32

Gly Pro Pro Ile Gly Ala Gly Tyr Asp
1               5

<210> SEQ ID NO 33
<211> LENGTH: 9
<212> TYPE: PRT
<213> ORGANISM: Artificial Sequence
<220> FEATURE:
<223> OTHER INFORMATION: Synthetic Construct

<400> SEQUENCE: 33

Gly Gln Thr Ile Gly Ala Gly Tyr Asp
1               5

<210> SEQ ID NO 34
<211> LENGTH: 9
<212> TYPE: PRT
<213> ORGANISM: Artificial Sequence
<220> FEATURE:
<223> OTHER INFORMATION: Synthetic Construct

<400> SEQUENCE: 34

Gly Pro Gln Ile Gly Ala Gly Tyr Asp

```
1               5
```

<210> SEQ ID NO 35
<211> LENGTH: 9
<212> TYPE: PRT
<213> ORGANISM: Artificial Sequence
<220> FEATURE:
<223> OTHER INFORMATION: Synthetic Construct

<400> SEQUENCE: 35

```
Gly Pro Thr Ile Gln Ala Gly Tyr Asp
1               5
```

<210> SEQ ID NO 36
<211> LENGTH: 9
<212> TYPE: PRT
<213> ORGANISM: Artificial Sequence
<220> FEATURE:
<223> OTHER INFORMATION: Synthetic Construct

<400> SEQUENCE: 36

```
Gly Pro Val Ile Gly Ala Gly Tyr Asp
1               5
```

<210> SEQ ID NO 37
<211> LENGTH: 9
<212> TYPE: PRT
<213> ORGANISM: Artificial Sequence
<220> FEATURE:
<223> OTHER INFORMATION: Synthetic Construct

<400> SEQUENCE: 37

```
Gly Gln Thr Ile Gly Ala Gly Tyr Asp
1               5
```

<210> SEQ ID NO 38
<211> LENGTH: 9
<212> TYPE: PRT
<213> ORGANISM: Artificial Sequence
<220> FEATURE:
<223> OTHER INFORMATION: Synthetic Construct

<400> SEQUENCE: 38

```
Gly Pro Thr Ile Gly Ala Gly Phe Asp
1               5
```

<210> SEQ ID NO 39
<211> LENGTH: 9
<212> TYPE: PRT
<213> ORGANISM: Artificial Sequence
<220> FEATURE:
<223> OTHER INFORMATION: Synthetic Construct

<400> SEQUENCE: 39

```
Gln Pro Thr Ile Gly Ala Gly Tyr Asp
1               5
```

<210> SEQ ID NO 40
<211> LENGTH: 9
<212> TYPE: PRT
<213> ORGANISM: Artificial Sequence
<220> FEATURE:
<223> OTHER INFORMATION: Synthetic Construct

<400> SEQUENCE: 40

```
Gly Pro Thr Ile Gly Gln Gly Tyr Asp
1               5
```

```
<210> SEQ ID NO 41
<211> LENGTH: 9
<212> TYPE: PRT
<213> ORGANISM: Artificial Sequence
<220> FEATURE:
<223> OTHER INFORMATION: Synthetic Construct

<400> SEQUENCE: 41

Gly Gln Thr Ile Gly Ala Gly Tyr Asp
1               5

<210> SEQ ID NO 42
<211> LENGTH: 10
<212> TYPE: PRT
<213> ORGANISM: Artificial Sequence
<220> FEATURE:
<223> OTHER INFORMATION: Synthetic Construct

<400> SEQUENCE: 42

Gln Ser Tyr Asp Arg Thr Leu Gly Val Val
1               5                   10

<210> SEQ ID NO 43
<211> LENGTH: 10
<212> TYPE: PRT
<213> ORGANISM: Artificial Sequence
<220> FEATURE:
<223> OTHER INFORMATION: Synthetic Construct

<400> SEQUENCE: 43

Gln Ser Tyr Asp Ser Thr Gln Gly Val Val
1               5                   10

<210> SEQ ID NO 44
<211> LENGTH: 10
<212> TYPE: PRT
<213> ORGANISM: Artificial Sequence
<220> FEATURE:
<223> OTHER INFORMATION: Synthetic Construct

<400> SEQUENCE: 44

Gln Ser Tyr Asp Ser Thr Leu Gly Val Val
1               5                   10

<210> SEQ ID NO 45
<211> LENGTH: 10
<212> TYPE: PRT
<213> ORGANISM: Artificial Sequence
<220> FEATURE:
<223> OTHER INFORMATION: Synthetic Construct

<400> SEQUENCE: 45

Gln Ser Tyr Asp Ser Thr His Gly Val Val
1               5                   10

<210> SEQ ID NO 46
<211> LENGTH: 10
<212> TYPE: PRT
<213> ORGANISM: Artificial Sequence
<220> FEATURE:
<223> OTHER INFORMATION: Synthetic Construct

<400> SEQUENCE: 46

Gln Ser Tyr Asp Ser Thr Pro Gly Val Val
1               5                   10
```

```
<210> SEQ ID NO 47
<211> LENGTH: 10
<212> TYPE: PRT
<213> ORGANISM: Artificial Sequence
<220> FEATURE:
<223> OTHER INFORMATION: Synthetic Construct

<400> SEQUENCE: 47

Gln Ser Tyr Asp Gln Thr Leu Gly Val Val
1               5                   10

<210> SEQ ID NO 48
<211> LENGTH: 10
<212> TYPE: PRT
<213> ORGANISM: Artificial Sequence
<220> FEATURE:
<223> OTHER INFORMATION: Synthetic Construct

<400> SEQUENCE: 48

Gln Ser Tyr Asp Arg Thr Leu Gly Val Val
1               5                   10

<210> SEQ ID NO 49
<211> LENGTH: 10
<212> TYPE: PRT
<213> ORGANISM: Artificial Sequence
<220> FEATURE:
<223> OTHER INFORMATION: Synthetic Construct

<400> SEQUENCE: 49

Gln Ser Tyr Asp Ser Ala Leu Gly Val Val
1               5                   10

<210> SEQ ID NO 50
<211> LENGTH: 10
<212> TYPE: PRT
<213> ORGANISM: Artificial Sequence
<220> FEATURE:
<223> OTHER INFORMATION: Synthetic Construct

<400> SEQUENCE: 50

Gln Ser Tyr Asp Ser Thr Glu Gly Val Val
1               5                   10

<210> SEQ ID NO 51
<211> LENGTH: 10
<212> TYPE: PRT
<213> ORGANISM: Artificial Sequence
<220> FEATURE:
<223> OTHER INFORMATION: Synthetic Construct

<400> SEQUENCE: 51

Gln Ser Tyr Asp Ser Thr Val Gly Val Val
1               5                   10

<210> SEQ ID NO 52
<211> LENGTH: 10
<212> TYPE: PRT
<213> ORGANISM: Artificial Sequence
<220> FEATURE:
<223> OTHER INFORMATION: Synthetic Construct

<400> SEQUENCE: 52

Gln Ala Tyr Asp Ser Thr Leu Gly Val Val
1               5                   10
```

```
<210> SEQ ID NO 53
<211> LENGTH: 10
<212> TYPE: PRT
<213> ORGANISM: Artificial Sequence
<220> FEATURE:
<223> OTHER INFORMATION: Synthetic Construct

<400> SEQUENCE: 53

Gln Ser Met Asp Ser Thr Leu Gly Val Val
1               5                   10

<210> SEQ ID NO 54
<211> LENGTH: 10
<212> TYPE: PRT
<213> ORGANISM: Artificial Sequence
<220> FEATURE:
<223> OTHER INFORMATION: Synthetic Construct

<400> SEQUENCE: 54

Gln Ser Tyr Asp Ser Thr Asp Gly Val Val
1               5                   10

<210> SEQ ID NO 55
<211> LENGTH: 8
<212> TYPE: PRT
<213> ORGANISM: Artificial Sequence
<220> FEATURE:
<223> OTHER INFORMATION: Synthetic Construct

<400> SEQUENCE: 55

Gly Gly Thr Phe Ser Gly Tyr Ala
1               5

<210> SEQ ID NO 56
<211> LENGTH: 8
<212> TYPE: PRT
<213> ORGANISM: Artificial Sequence
<220> FEATURE:
<223> OTHER INFORMATION: Synthetic Construct

<400> SEQUENCE: 56

Gln Ile Pro Ile Leu Gly Ile Ala
1               5

<210> SEQ ID NO 57
<211> LENGTH: 8
<212> TYPE: PRT
<213> ORGANISM: Artificial Sequence
<220> FEATURE:
<223> OTHER INFORMATION: Synthetic Construct

<400> SEQUENCE: 57

Ile Ile Pro Ala Leu Gly Ile Ala
1               5

<210> SEQ ID NO 58
<211> LENGTH: 8
<212> TYPE: PRT
<213> ORGANISM: Artificial Sequence
<220> FEATURE:
<223> OTHER INFORMATION: Synthetic Construct

<400> SEQUENCE: 58

Ile Ile Pro Ile Leu Gln Ile Ala
1               5

<210> SEQ ID NO 59
```

```
<211> LENGTH: 8
<212> TYPE: PRT
<213> ORGANISM: Artificial Sequence
<220> FEATURE:
<223> OTHER INFORMATION: Synthetic Construct

<400> SEQUENCE: 59

Ile Ile Pro Ile Met Gly Ile Ala
1               5

<210> SEQ ID NO 60
<211> LENGTH: 8
<212> TYPE: PRT
<213> ORGANISM: Artificial Sequence
<220> FEATURE:
<223> OTHER INFORMATION: Synthetic Construct

<400> SEQUENCE: 60

Ile Ile Pro Val Leu Gly Ile Ala
1               5

<210> SEQ ID NO 61
<211> LENGTH: 8
<212> TYPE: PRT
<213> ORGANISM: Artificial Sequence
<220> FEATURE:
<223> OTHER INFORMATION: Synthetic Construct

<400> SEQUENCE: 61

Ile Ser Pro Ile Leu Gly Ile Ala
1               5

<210> SEQ ID NO 62
<211> LENGTH: 8
<212> TYPE: PRT
<213> ORGANISM: Artificial Sequence
<220> FEATURE:
<223> OTHER INFORMATION: Synthetic Construct

<400> SEQUENCE: 62

Ile Ile Pro Ile Leu Gly Gln Ala
1               5

<210> SEQ ID NO 63
<211> LENGTH: 14
<212> TYPE: PRT
<213> ORGANISM: Artificial Sequence
<220> FEATURE:
<223> OTHER INFORMATION: Synthetic Construct

<400> SEQUENCE: 63

Ala Gln Ser Gly Tyr Gly Tyr Ala Tyr Gly Ser Phe Asp Tyr
1               5                   10

<210> SEQ ID NO 64
<211> LENGTH: 14
<212> TYPE: PRT
<213> ORGANISM: Artificial Sequence
<220> FEATURE:
<223> OTHER INFORMATION: Synthetic Construct

<400> SEQUENCE: 64

Ala Arg Ser Gly His Gly Tyr Ala Tyr Gly Ser Phe Asp Tyr
1               5                   10

<210> SEQ ID NO 65
<211> LENGTH: 14
```

```
<212> TYPE: PRT
<213> ORGANISM: Artificial Sequence
<220> FEATURE:
<223> OTHER INFORMATION: Synthetic Construct

<400> SEQUENCE: 65

Ala Arg Ser Gly Pro Gly Tyr Ala Tyr Gly Ser Phe Asp Tyr
1               5                   10

<210> SEQ ID NO 66
<211> LENGTH: 14
<212> TYPE: PRT
<213> ORGANISM: Artificial Sequence
<220> FEATURE:
<223> OTHER INFORMATION: Synthetic Construct

<400> SEQUENCE: 66

Ala Arg Ser Gly Tyr Gly Tyr Ala Tyr Gly Ser Phe Ala Ala
1               5                   10

<210> SEQ ID NO 67
<211> LENGTH: 14
<212> TYPE: PRT
<213> ORGANISM: Artificial Sequence
<220> FEATURE:
<223> OTHER INFORMATION: Synthetic Construct

<400> SEQUENCE: 67

Ala Arg Ser Gly Tyr Gly Tyr Ala Tyr Gly Ser Phe Asp Met
1               5                   10

<210> SEQ ID NO 68
<211> LENGTH: 14
<212> TYPE: PRT
<213> ORGANISM: Artificial Sequence
<220> FEATURE:
<223> OTHER INFORMATION: Synthetic Construct

<400> SEQUENCE: 68

Ala Arg Ser Gly Tyr Gly Tyr Ala Tyr Gly Ser Phe Asp Val
1               5                   10

<210> SEQ ID NO 69
<211> LENGTH: 14
<212> TYPE: PRT
<213> ORGANISM: Artificial Sequence
<220> FEATURE:
<223> OTHER INFORMATION: Synthetic Construct

<400> SEQUENCE: 69

Ala Arg Ser Gly Tyr Gly Tyr Ala Tyr Gly Ser Phe Asp Tyr
1               5                   10

<210> SEQ ID NO 70
<211> LENGTH: 14
<212> TYPE: PRT
<213> ORGANISM: Artificial Sequence
<220> FEATURE:
<223> OTHER INFORMATION: Synthetic Construct

<400> SEQUENCE: 70

Ala Arg Ser Gly Tyr Gly Tyr Ala Tyr Gly Ser Phe Asp Tyr
1               5                   10

<210> SEQ ID NO 71
<211> LENGTH: 14
<212> TYPE: PRT
```

<213> ORGANISM: Artificial Sequence
<220> FEATURE:
<223> OTHER INFORMATION: Synthetic Construct

<400> SEQUENCE: 71

Ala Arg Ser Gly Tyr Gly Tyr Ala Tyr Gly Ser Phe Asp Tyr
1               5                   10

<210> SEQ ID NO 72
<211> LENGTH: 14
<212> TYPE: PRT
<213> ORGANISM: Artificial Sequence
<220> FEATURE:
<223> OTHER INFORMATION: Synthetic Construct

<400> SEQUENCE: 72

Ala Arg Ser Gly Tyr Gly Tyr Ala Tyr Gly Ser Phe Asp Tyr
1               5                   10

<210> SEQ ID NO 73
<211> LENGTH: 14
<212> TYPE: PRT
<213> ORGANISM: Artificial Sequence
<220> FEATURE:
<223> OTHER INFORMATION: Synthetic Construct

<400> SEQUENCE: 73

Ala Arg Ser Gly Tyr Gly Tyr Ala Tyr Gly Ser Phe Asp Tyr
1               5                   10

<210> SEQ ID NO 74
<211> LENGTH: 14
<212> TYPE: PRT
<213> ORGANISM: Artificial Sequence
<220> FEATURE:
<223> OTHER INFORMATION: Synthetic Construct

<400> SEQUENCE: 74

Ala Arg Ser Gly Tyr Gly Tyr Ala Tyr Gly Ser Phe Asp Tyr
1               5                   10

<210> SEQ ID NO 75
<211> LENGTH: 14
<212> TYPE: PRT
<213> ORGANISM: Artificial Sequence
<220> FEATURE:
<223> OTHER INFORMATION: Synthetic Construct

<400> SEQUENCE: 75

Ala Arg Ser Gly Tyr Gly Tyr Ala Tyr Gly Ser Phe Asp Tyr
1               5                   10

<210> SEQ ID NO 76
<211> LENGTH: 14
<212> TYPE: PRT
<213> ORGANISM: Artificial Sequence
<220> FEATURE:
<223> OTHER INFORMATION: Synthetic Construct

<400> SEQUENCE: 76

Ala Arg Ser Gly Tyr Gly Tyr Ala Tyr Gly Ser Phe Asp Tyr
1               5                   10

<210> SEQ ID NO 77
<211> LENGTH: 14
<212> TYPE: PRT
<213> ORGANISM: Artificial Sequence

```
<220> FEATURE:
<223> OTHER INFORMATION: Synthetic Construct

<400> SEQUENCE: 77

Ala Arg Ser Gly Tyr Gly Tyr Ala Tyr Gly Ser Phe Asp Tyr
1               5                   10

<210> SEQ ID NO 78
<211> LENGTH: 14
<212> TYPE: PRT
<213> ORGANISM: Artificial Sequence
<220> FEATURE:
<223> OTHER INFORMATION: Synthetic Construct

<400> SEQUENCE: 78

Ala Arg Ser Gly Tyr Gly Tyr Ala Tyr Gly Ser Phe Asp Tyr
1               5                   10

<210> SEQ ID NO 79
<211> LENGTH: 14
<212> TYPE: PRT
<213> ORGANISM: Artificial Sequence
<220> FEATURE:
<223> OTHER INFORMATION: Synthetic Construct

<400> SEQUENCE: 79

Ala Arg Ser Gly Tyr Gly Tyr Ala Tyr Gly Ser Phe Asp Tyr
1               5                   10

<210> SEQ ID NO 80
<211> LENGTH: 14
<212> TYPE: PRT
<213> ORGANISM: Artificial Sequence
<220> FEATURE:
<223> OTHER INFORMATION: Synthetic Construct

<400> SEQUENCE: 80

Ala Arg Ser Gly Tyr Gly Tyr Ala Tyr Gly Ser Phe Asp Tyr
1               5                   10

<210> SEQ ID NO 81
<211> LENGTH: 14
<212> TYPE: PRT
<213> ORGANISM: Artificial Sequence
<220> FEATURE:
<223> OTHER INFORMATION: Synthetic Construct

<400> SEQUENCE: 81

Ala Arg Ser Gly Tyr Gly Tyr Ala Tyr Gly Ser Phe Asp Tyr
1               5                   10

<210> SEQ ID NO 82
<211> LENGTH: 14
<212> TYPE: PRT
<213> ORGANISM: Artificial Sequence
<220> FEATURE:
<223> OTHER INFORMATION: Synthetic Construct

<400> SEQUENCE: 82

Ala Arg Ser Gly Tyr Gly Tyr Ala Tyr Gly Ser Phe Asp Tyr
1               5                   10

<210> SEQ ID NO 83
<211> LENGTH: 14
<212> TYPE: PRT
<213> ORGANISM: Artificial Sequence
<220> FEATURE:
```

```
<223> OTHER INFORMATION: Synthetic Construct

<400> SEQUENCE: 83

Ala Arg Ser Gly Tyr Gly Tyr Ala Tyr Gly Ser Phe Asp Tyr
1               5                   10

<210> SEQ ID NO 84
<211> LENGTH: 14
<212> TYPE: PRT
<213> ORGANISM: Artificial Sequence
<220> FEATURE:
<223> OTHER INFORMATION: Synthetic Construct

<400> SEQUENCE: 84

Ala Arg Ser Gly Tyr Gly Tyr Ala Tyr Gly Ser Phe Asp Tyr
1               5                   10

<210> SEQ ID NO 85
<211> LENGTH: 14
<212> TYPE: PRT
<213> ORGANISM: Artificial Sequence
<220> FEATURE:
<223> OTHER INFORMATION: Synthetic Construct

<400> SEQUENCE: 85

Ala Arg Ser Gly Tyr Gly Tyr Ala Tyr Gly Val Phe Asp His
1               5                   10

<210> SEQ ID NO 86
<211> LENGTH: 4
<212> TYPE: PRT
<213> ORGANISM: Artificial Sequence
<220> FEATURE:
<223> OTHER INFORMATION: Synthetic Construct

<400> SEQUENCE: 86

Gly Phe Leu Gly
1

<210> SEQ ID NO 87
<211> LENGTH: 121
<212> TYPE: PRT
<213> ORGANISM: Artificial Sequence
<220> FEATURE:
<223> OTHER INFORMATION: Synthetic Construct

<400> SEQUENCE: 87

Gln Val Gln Leu Val Glu Ser Gly Ala Glu Val Lys Lys Pro Gly Ser
1               5                   10                  15

Ser Val Lys Val Ser Cys Lys Ala Ser Gly Gly Thr Phe Ser Ser Tyr
                20                  25                  30

Ala Ile Ser Trp Val Arg Gln Ala Pro Gly Gln Gly Leu Glu Trp Met
            35                  40                  45

Gly Arg Ile Ile Pro Ile Leu Gly Ile Ala Asn Tyr Ala Gln Lys Phe
        50                  55                  60

Gln Gly Arg Val Thr Val Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Gly Tyr Gly Tyr Ala Tyr Gly Ser Phe Asp Tyr Trp Gly
                100                 105                 110

Gln Gly Thr Leu Val Thr Val Ser Ser
            115                 120
```

<210> SEQ ID NO 88
<211> LENGTH: 108
<212> TYPE: PRT
<213> ORGANISM: Artificial Sequence
<220> FEATURE:
<223> OTHER INFORMATION: Synthetic Construct

<400> SEQUENCE: 88

```
Gln Leu Val Leu Thr Gln Pro Pro Ser Val Ser Gly Ala Pro Gly Gln
1               5                   10                  15

Thr Val Thr Ile Ser Cys Thr Gly Gln Thr Ile Gly Ala Gly Tyr Asp
            20                  25                  30

Val His Trp Tyr Gln Gln Leu Pro Gly Ala Ala Pro Lys Leu Leu Ile
        35                  40                  45

Tyr Gly Asn Leu Asn Arg Pro Ser Gly Val Pro Asp Arg Phe Ser Gly
    50                  55                  60

Ser Lys Ser Gly Thr Ser Ala Ser Leu Ala Ile Thr Asp Leu Gln Ala
65                  70                  75                  80

Glu Asp Glu Ala Asp Tyr Tyr Cys Gln Ser Tyr Asp Ser Arg Leu Gly
                85                  90                  95

Val Val Phe Gly Gly Gly Thr Lys Leu Thr Val Leu
            100                 105
```

ANTIBODIES AGAINST PROGRAMMED DEATH-LIGAND 1 AND USES THEREOF

CROSS-REFERENCE TO RELATED APPLICATIONS

This is a U.S. national phase under 35 USC § 371 of International Patent Application No. PCT/KR20/04854 filed Apr. 9, 2020, which in turn claims priority under 35 USC § 119 of Korean Patent Application No. 10-2019-0042501 filed Apr. 11, 2002. The disclosures of all such applications are hereby incorporated herein by reference in their respective entireties, for all purposes.

REFERENCE TO SEQUENCE LISTING SUBMITTED VIA PATENT CENTER

This application includes an electronically submitted sequence listing in .txt format. The .txt file contains a sequence listing entitled "582_UpdatedSeqListing_ST25.txt" created on Feb. 16, 2025 and is 47,412 bytes in size. The sequence listing contained in this .txt file is part of the specification and is hereby incorporated by reference herein in its entirety.

TECHNICAL FIELD

The present invention relates to an antibody to PD-L1 (programmed death-ligand 1) or an antigen-binding fragment thereof, a nucleic acid encoding the same, a vector including the nucleic acid, a cell transfected with the vector, a method of producing the antibody or the antigen-binding fragment thereof, a composition for preventing or treating cancer comprising the same, and a composition for combination therapy for preventing or treating cancer including the same.

BACKGROUND ART

PD-L1 is a type 1 transmembrane protein having two Ig-like domains within the extracellular region, a transmembrane domain, and a short cytoplasmic domain. The cytoplasmic domain does not have a known signal transduction motif, indicating that PD-L1 has no signaling for interaction with the receptor thereof. PD-L1 has a molecular weight of 40 kDa (290 amino acids) and is encoded by the CD274 gene on mouse chromosome 19 and human chromosome 9. PD-L1 is a member of the B7 protein family and shares about 20% amino acid sequence identity with B7.1 and B7.2. Human PD-L1 shares amino acid identity of 70% and 93% with PD-L1 of murine and a cynomolgus ortholog, respectively.

PD-L1 binds to PD-1, which is the receptor thereof, with an affinity (KD) of 770 nM. PD-1 is expressed on activated T cells, B cells, and bone marrow cells, and modulates the activation or suppression of cellular immune responses. PD-L1 expression in cells may mediate protection against cytotoxic T lymphocyte (CTL) death, which is a regulatory mechanism that blunts chronic immune responses during viral infection. Cancers, such as chronic and pro-inflammatory diseases, subvert the immune-protective pathway through upregulation of PD-L1 expression to thus evade the host immune response. In the active immune response, IFNγ also upregulates the expression of PD-L1.

PD-L1 also mediates immunosuppression through interaction with another protein B7.1 (also known as CD80), thus blocking the ability to transmit one of the secondary signals of activation to T cells through CD28. In view of PD-L1 expression on tumor cells and engagement with B7.1, the relevance of this specific interaction in tumor immune resistance remains unclear.

The immune function of the human body regulates the overall function of T lymphocytes through the control of co-stimulatory and co-inhibitory signals at the same time as antigen recognition. This regulatory mechanism is called an immune checkpoint. The immune function of the human body detects tumor-specific neo-antigens expressed due to changes such as mutations occurring in tumor cells and removes tumor cells or sources of viral infection therethrough.

However, some tumor cells suppress the immune function by changing the tumor microenvironment in order to avoid such an immune attack, or promote immune escape through T-cell immune tolerance or immuno-editing.

As one of these escape strategies, the function of tumor-specific T lymphocytes is suppressed through changes in immune checkpoint function. Specifically, by activating the inhibitory immune checkpoint in tumor cells, the attack of tumor-specific T-lymphocytes is avoided. In this regard, an antitumor effect may be obtained by enhancing the suppressed tumor-specific T-lymphocyte cell activity and effect by inhibiting the function thereof using a monoclonal antibody to PD-1 or the ligand PD-L1.

Against this technical background, the inventors of the present application have endeavored to develop an antibody that specifically binds to PD-L1. As a result, the present inventors have developed an anti-PD-L1 antibody that binds to PD-L1 with high affinity, and ascertained that the anti-PD-L1 antibody may inhibit the formation of a PD-1/PD-L1 complex and thus may desirably function as an immuno-oncology drug, thereby culminating in the present invention.

DISCLOSURE

It is an object of the present invention to provide a novel antibody to PD-L1 or an antigen-binding fragment thereof.

It is another object of the present invention to provide a nucleic acid encoding the antibody or the antigen-binding fragment thereof.

It is still another object of the present invention to provide a vector including the nucleic acid, a cell transfected with the vector, and a method of producing the same.

It is yet another object of the present invention to provide a composition for preventing or treating cancer or infectious disease comprising the antibody or the antigen-binding fragment thereof.

It is still yet another object of the present invention to provide a composition for combination therapy for preventing or treating cancer by administering the antibody or the antigen-binding fragment thereof in combination with another anticancer agent.

In order to accomplish the above objects, the present invention provides an antibody binding to PD-L1 or an antigen-binding fragment thereof, which comprises a heavy-chain CDR1 comprising a sequence having at least 90% sequence homology with the sequence of SEQ ID NO: 1, a heavy-chain CDR2 comprising a sequence having at least 90% sequence homology with the sequence of SEQ ID NO: 2, a heavy-chain CDR3 comprising a sequence having at least 90% sequence homology with the sequence of SEQ ID NO: 3 or SEQ ID NO: 11, a light-chain CDR1 comprising a sequence having at least 90% sequence homology with the sequence of SEQ ID NO: 5 or SEQ ID NO: 13, a light-chain CDR2 comprising a sequence having at least 90% sequence homology with the sequence of SEQ ID NO: 6, and a light-chain CDR3 comprising a sequence having at least 90% sequence homology with the sequence of SEQ ID NO: 7.

In addition, the present invention provides a nucleic acid encoding the antibody or the antigen-binding fragment thereof.

In addition, the present invention provides a vector comprising the nucleic acid.

In addition, the present invention provides a cell transfected with the vector.

In addition, the present invention provides a method of producing the antibody or the antigen-binding fragment thereof comprising (a) culturing the cell described above and (b) purifying an antibody or an antigen-binding fragment thereof from the cultured cell.

In addition, the present invention provides a composition for preventing or treating cancer comprising the antibody or the antigen-binding fragment thereof as an active ingredient.

In addition, the present invention provides a composition for combination therapy for preventing or treating cancer by administering the antibody or the antigen-binding fragment thereof in combination with another anticancer agent.

DESCRIPTION OF DRAWINGS

FIG. 1 shows the results of an ELISA reaction for verification of the binding of individual antibody clones (about 1400) obtained through a phage display experiment on a PD-L1 antigen protein;

FIG. 2 shows the results of a FACS experiment on representative antibody clones to 293T cells in which the human PD-L1 gene is artificially expressed on the surface thereof in order to analyze the binding of the PD-L1-binding antibody clones to an antigen protein on the cell surface;

FIG. 3 shows the results of verification of a change in SPR sensorgram when the antibody sample is included together compared to the solution condition (blue line) containing only the PD-L1 antigen protein through an SPR-based performance evaluation test for confirming PD-1/PD-L1 binding inhibitory performance of 9 representative antibody clones;

FIG. 4 shows the results of analysis of binding of the IgG-type PD-L1 target antibody candidates to the mouse PD-L1 protein using an mIFN-γ-treated mouse colon cancer cell line MC38;

FIG. 5 shows results confirming the binding inhibitory performance between PD-1/PD-L1 proteins in an in-vitro cell-based performance verification test of candidate antibodies;

FIG. 6 shows the results of analysis of the in-vivo anticancer performance of candidate antibodies using a mouse-derived colon cancer cell line MC38 and a C57BL/6 syngeneic mouse model;

FIG. 7 shows results confirming the ability of the selected candidate antibody (KL001) to increase immune cell activity;

FIG. 8 shows results confirming the ability to increase immune cell activity of the KL01-13 candidate antibody selected after affinity maturation of candidate antibodies;

FIG. 9 shows results confirming the output increase pattern depending on the panning order of the performance improvement optimization experiment of candidate antibodies;

FIG. 10 shows the results of an ELISA reaction for affinity improvement antibody selection;

FIG. 11 shows the results of measuring the ability of the selected antibody to bind to human PD-L1 and mouse PD-L1 using a BIACORE™ surface plasmon resonance device;

FIG. 12 shows the results of evaluating the tumor growth inhibitory efficacy upon i.p. administration of the performance optimization antibody 'KL001-13', the pre-optimization antibody 'KL001', and the MPDL3280A comparative antibody in the MC38 subcutaneous syngeneic mouse model;

FIG. 13 shows the results of measuring the IC50 value of the selected antibody using an in-vitro cell-based assay;

FIG. 14 shows the results of verifying the in-vivo anticancer effect on the combined treatment of IL-2 and the KL001-13 antibody or the MPDL3280A comparative antibody;

FIG. 15 shows the results of verifying the in-vivo anticancer effect on the combined treatment of the CTLA-4 antibody (9D9) and the KL001-13 antibody or the MPDL3280A comparative antibody;

FIG. 16 shows the sequences of the CDRs of the antibody according to the present invention when using different numbering schemes in addition to the IMGT numbering scheme; and FIG. 17 shows the cross-reactivity of the antibody according to the invention to humans, mice, monkeys, and dogs.

MODE FOR INVENTION

Unless otherwise defined, all technical and scientific terms used herein have the same meanings as those typically understood by those skilled in the art to which the present invention belongs. Generally, the nomenclature used herein is well known in the art and is typical.

In one aspect, the present invention pertains to an antibody binding to PD-L1 or an antigen-binding fragment thereof, which comprises a heavy-chain CDR1 comprising a sequence having at least 90% sequence homology with the sequence of SEQ ID NO: 1, a heavy-chain CDR2 comprising a sequence having at least 90% sequence homology with the sequence of SEQ ID NO: 2, a heavy-chain CDR3 comprising a sequence having at least 90% sequence homology with the sequence of SEQ ID NO: 3 or SEQ ID NO: 11, a light-chain CDR1 comprising a sequence having at least 90% sequence homology with the sequence of SEQ ID NO: 5 or SEQ ID NO: 13, a light-chain CDR2 comprising a sequence having at least 90% sequence homology with the sequence of SEQ ID NO: 6, and a light-chain CDR3 comprising a sequence having at least 90% sequence homology with the sequence of SEQ ID NO: 7.

"PD-L1" as used herein is a ligand for the immunosuppressive receptor "programmed death receptor 1 (PD-1)" mainly expressed on activated T and B cells, and when PD-1 and ligands PD-L1 and/or PD-L2 are bound, antigen receptor signaling may be negatively regulated. Ligands for PD-1 (PD-L1 and PD-L2) may be constitutively expressed or induced in multiple cell types comprising non-hematopoietic tissues and various tumor types. PD-L1 is expressed on B cells, T cells, bone marrow cells, and dendritic cells (DCs), and is also expressed on peripheral cells, similar microvascular endothelial cells, and non-lymphatic organs such as the heart, lungs, etc. In contrast, PD-L2 is only found on macrophages and dendritic cells. The expression pattern of the PD-1 ligand may represent a role for PD-1 in maintaining peripheral tolerance, and may contribute to regulating auto-reactive T-cell and B-cell responses in the periphery. PD-L1 and PD-L2 are type 1 transmembrane receptors that contain both IgV- and IgC-like domains within the extracellular region. Both ligands contain short cytoplasmic domains having unknown signaling motifs.

Numerous studies have revealed that the interaction of PD-1 with the ligand thereof inhibits lymphocyte proliferation in vitro and in vivo. Blockade of the PD-1/PD-L1 interaction is known to increase T cell proliferation and cytokine production and to block cell cycle progression. Blockade of the PD-1/PD-L1 interaction may induce enhanced tumor-specific T-cell immunity, thus helping the immune system to clear tumor cells. Moreover, upon chronic HIV infection, HIV-specific CD8+ T cells are functionally impaired, and the abilities to produce cytokines and effector molecules and to proliferate the same are decreased. PD-1 is highly expressed in HIV-specific CD8+ T cells of HIV-infected individuals, and blockade of the PD-1/PD-L1 interaction is capable of improving the ability to proliferate HIV-specific T cells and to produce cytokines in response to HIV peptide stimulation, thereby enhancing T cell activity or antiviral immune response.

As used herein, the term "antibody" refers to an anti-PD-L1 antibody that specifically binds to PD-L1. A complete antibody that specifically binds to PD-L1 and also an antigen-binding fragment of the antibody molecule are included in the scope of the present invention.

A complete antibody has a structure having two full-length light chains and two full-length heavy chains, the light chains being respectively linked to the heavy chains through disulfide bonding. The heavy-chain constant region has gamma (γ), mu (μ), alpha (α), delta (δ) and epsilon (ε) types, and also has gamma 1 (γ1), gamma 2 (γ2), gamma 3 (γ3), gamma 4 (γ4), alpha 1 (α1) and alpha 2 (α2) subclasses. The light-chain constant region has kappa (κ) and lambda (λ) types.

The antigen-binding fragment of the antibody or the antibody fragment is a fragment having an antigen-binding function, and includes Fab, F(ab'), F(ab')$_2$, Fv and the like. Among these antibody fragments, Fab has a structure having light-chain and heavy-chain variable regions, a light-chain constant region, and a first heavy-chain constant region (CH1), and has one antigen-binding site. Fab' differs from Fab in that Fab' has a hinge region comprising at least one cysteine residue at the C-terminus of the heavy-chain CH1 domain.

The F(ab')$_2$ antibody is created by a disulfide bond between cysteine residues in the hinge region of Fab'. Fv is a minimal antibody fragment having only a heavy-chain variable region and a light-chain variable region. A two-chain Fv is a fragment in which a heavy-chain variable region and a light-chain variable region are linked by a non-covalent bond, and a single-chain Fv (scFv) is a fragment in which a heavy-chain variable region and a light-chain variable region are generally linked by a covalent bond via a peptide linker therebetween, or are directly linked at the C-terminus, forming a dimeric structure, like the two-chain Fv. Such antibody fragments may be obtained using proteases (for example, Fab may be obtained by restriction-cleaving a whole antibody with papain, and the F(ab')$_2$ fragment may be obtained by restriction-cleaving a whole antibody with pepsin), or may be prepared through genetic recombination technology.

In one embodiment, the antibody according to the invention is in the form of Fv (e.g. scFv) or in the form of a complete antibody. Also, the heavy-chain constant region may be any one selected from among isotypes such as gamma (γ), mu (μ), alpha (α), delta (δ), and epsilon (ε). For example, the constant region may be gamma 1 (IgG1), gamma 3 (IgG3), or gamma 4 (IgG4). The light-chain constant region may be a kappa or lambda type.

As used herein, the term "heavy chain" refers to a full-length heavy chain comprising a variable region domain VH comprising an amino acid sequence having a variable region sequence sufficient to confer specificity to an antigen and three constant region domains CH1, CH2 and CH3, and a fragment thereof. Also, as used herein, the term "light chain" refers to a full-length light chain comprising a variable region domain VL comprising an amino acid sequence having a variable region sequence sufficient to confer specificity to an antigen and a constant region domain CL, and a fragment thereof.

Examples of the antibody of the present invention include, but are not limited to, monoclonal antibodies, multispecific antibodies, human antibodies, humanized antibodies, chimeric antibodies, single-chain Fvs (scFV), single-chain antibodies, Fab fragments, F(ab') fragments, disulfide-linked Fvs (sdFV), anti-idiotype (anti-Id) antibodies, epitope-binding fragments of such antibodies, and the like.

A monoclonal antibody is an antibody obtained from a population of substantially homogeneous antibodies, in which the individual antibodies that make up the population are identical, except for possible naturally-occurring mutations that may be present in small amounts. The monoclonal antibody is highly specific and is induced against a single antigenic site. In contrast to typical (polyclonal) antibody preparations, which typically include different antibodies directed against different determinants (epitopes), each monoclonal antibody is directed against a single determinant on the antigen.

The term "epitope" refers to a protein determinant to which an antibody may specifically bind. The epitope is usually composed of a group of chemically active surface molecules, for example amino acids or sugar side chains, and generally has specific three-dimensional structural features and specific charge properties. Steric and nonsteric epitopes are distinguished in that binding to the former is lost but not to the latter in the presence of a denaturing solvent.

A non-human antibody in a "humanized" form is a chimeric antibody that contains a minimal sequence derived from a non-human (e.g. murine) immunoglobulin. In most cases, the humanized antibody is a human immunoglobulin (acceptor antibody), in which a residue from the hypervariable region of an acceptor is replaced with a residue from the hypervariable region of a non-human species (donor antibody) having the desired specificity, affinity and capability, for example, mice, rats, rabbits or non-human primates.

A "human antibody" is a molecule derived from human immunoglobulin, and means that all of the amino acid sequences constituting the antibody comprising a complementarity-determining region and a structural region are composed of human immunoglobulin.

A portion of the heavy chain and/or light chain is identical to or homologous with the corresponding sequence in an antibody derived from a particular species or belonging to a particular antibody class or subclass, while the remaining chain(s) includes a "chimeric" antibody (immunoglobulin) that is identical to or homologous with the corresponding sequence in an antibody derived from another species or belonging to another antibody class or subclass as well as fragments of such antibodies that exhibit the desired biological activity.

The "antibody variable domain" as used herein refers to the light-chain and heavy-chain portions of an antibody molecule comprising the amino acid sequences of a complementarity-determining region (CDR; i.e. CDR1, CDR2, and CDR3) and a framework region (FR). VH refers to the variable domain of a heavy chain, and VL refers to the variable domain of a light chain.

The "complementarity-determining region" (CDR; i.e. CDR1, CDR2, and CDR3) refers to an amino acid residue of the antibody variable domain that is necessary for antigen binding. Each variable domain typically has three CDRs, identified as CDR1, CDR2, and CDR3.

The present invention pertains to an antibody binding to PD-L1 or an antigen-binding fragment thereof, comprising a heavy-chain CDR1 comprising the sequence of SEQ ID NO: 1, a heavy-chain CDR2 comprising the sequence of SEQ ID NO: 2, a heavy-chain CDR3 comprising the sequence of SEQ ID NO: 3 or SEQ ID NO: 11, a light-chain CDR1 comprising the sequence of SEQ ID NO: 5 or SEQ ID NO: 13, a light-chain CDR2 comprising the sequence of SEQ ID NO: 6, and a light-chain CDR3 comprising the sequence of SEQ ID NO: 7 (the CDR numbering scheme used in the present patent is in accordance with 'IMGT numbering'). According to the present invention, the antibody binding to PD-L1 or the antigen-binding fragment thereof may include a heavy-chain variable region comprising the heavy-chain CDR1 of SEQ ID NO: 1, the heavy-chain CDR2 of SEQ ID NO: 2, and the heavy-chain CDR3 of SEQ ID NO: 3, or a heavy-chain variable region comprising the heavy-chain CDR1 of SEQ ID NO: 1, the heavy-chain CDR2 of SEQ ID NO: 2, and the heavy-chain CDR3 of SEQ ID NO: 11.

In the present invention, the antibody binding to PD-L1 or the antigen-binding fragment thereof may comprise a light-chain variable region comprising the light-chain CDR1 of SEQ ID NO: 5, the light-chain CDR2 of SEQ ID NO: 6, and the light-chain CDR3 of SEQ ID NO: 7, or a light-chain variable region comprising the light-chain CDR1 of SEQ ID NO: 13, the light-chain CDR2 of SEQ ID NO: 6, and the light-chain CDR3 of SEQ ID NO: 7.

TABLE 1

CDR sequence of antibody according to the present invention

| Classification | | CDR sequence | SEQ ID NO: |
|---|---|---|---|
| Heavy chain | CDR1 | GGTFSSYA | 1 |
| | CDR2 | IIPILGIA | 2 |
| | CDR3 | ARSGYSYAYGSFDY | 3 |
| | | ARSGYGYAYGSFDY | 11 |
| Light chain | CDR1 | GPTIGAGYD | 5 |
| | | GQTIGAGYD | 13 |
| | CDR2 | GNL | 6 |
| | CDR3 | QSYDSRLGVV | 7 |

Specifically, in the present invention, the antibody binding to PD-L1 or the antigen-binding fragment thereof may comprise: a heavy-chain variable region comprising the heavy-chain CDR1 of SEQ ID NO: 1, the heavy-chain CDR2 of SEQ ID NO: 2, and the heavy-chain CDR3 of SEQ ID NO: 3, and a light-chain variable region comprising the light-chain CDR1 of SEQ ID NO: 5, the light-chain CDR2 of SEQ ID NO: 6, and the light-chain CDR3 of SEQ ID NO: 7; or a heavy-chain variable region comprising the heavy-chain CDR1 of SEQ ID NO: 1, the heavy-chain CDR2 of SEQ ID NO: 2, and the heavy-chain CDR3 of SEQ ID NO: 11, and a light-chain variable region comprising the light-chain CDR1 of SEQ ID NO: 13, the light-chain CDR2 of SEQ ID NO: 6, and the light-chain CDR3 of SEQ ID NO: 7.

The "framework region" (FR) is a variable domain residue other than the CDR residue. Each variable domain typically has four FRs, identified as FR1, FR2, FR3, and FR4.

The PD-L1 antibody is monovalent or divalent and contains a single chain or two chains. Functionally, the binding affinity of the PD-L1 antibody falls within the range of $10^{-5}$ M to $10^{-12}$ M. For example, the binding affinity of the PD-L1 antibody may be $10^{-6}$ M to $10^{-12}$ M, $10^{-7}$ M to $10^{-12}$ M, $10^{-8}$ M to $10^{-12}$ M, $10^{-9}$ M to $10^{-12}$ M, $10^{-10}$ M to $10^{-12}$ M, $10^{-11}$ M to $10^{-12}$ M, $10^{-5}$ M to $10^{-11}$ M, $10^{-6}$ M to $10^{-11}$ M, $10^{-7}$ M to $10^{-11}$ M, $10^{-8}$ M to $10^{-11}$ M, $10^{-9}$ M to $10^{-11}$ M, $10^{-10}$ M to $10^{-11}$ M, $10^{-5}$ M to $10^{-10}$ M, $10^{-6}$ M to $10^{-10}$ M, $10^{-7}$ M to $10^{-10}$ M, $10^{-8}$ M to $10^{-10}$ M, $10^{-9}$ M to $10^{-10}$ M, $10^{-5}$ M to $10^{-9}$ M, $10^{-6}$ M to $10^{-9}$ M, $10^{-7}$ M to $10^{-9}$ M, $10^{-8}$ M to $10^{-9}$ M, $10^{-5}$ M to $10^{-8}$ M, $10^{-6}$ M to $10^{-8}$ M, $10^{-7}$ M to $10^{-8}$ M, $10^{-5}$ M to $10^{-7}$ M, $10^{-6}$ M to $10^{-7}$ M, or $10^{-5}$ M to $10^{-6}$ M.

The antibody binding to PD-L1 or the antigen-binding fragment thereof may comprise a heavy-chain variable region comprising a sequence having at least 90% sequence homology with the sequence of SEQ ID NO: 4 or SEQ ID NO: 12. The antibody binding to PD-L1 or the antigen-binding fragment thereof may comprise the heavy-chain variable region of SEQ ID NO: 4 or SEQ ID NO: 12. Also, the antibody binding to PD-L1 or the antigen-binding fragment thereof may comprise a light-chain variable region comprising a sequence having at least 90% sequence homology with the sequence of SEQ ID NO: 8 or SEQ ID NO: 14.

In a specific embodiment according to the present invention, the heavy-chain variable region of SEQ ID NO: 4 and the light-chain variable region of SEQ ID NO: 8 may be comprised, or the heavy-chain variable region of SEQ ID NO: 12 and the light-chain variable region of SEQ ID NO: 14 may be comprised.

Meanwhile, the definition of the CDR sequence (region) may differ slightly for an antibody having the same variable region depending on the numbering scheme thereof.

Specifically, as shown in Table 2 below, even in the same variable region, the CDR sequence may be defined differently depending on the numbering scheme.

TABLE 2

CDR sequence (region) depending on numbering scheme

| CDR | IMGT | Kabat | Chothia |
|---|---|---|---|
| CDR H1 | H26~H35B | H31~H35B | H26~H32 ... 34 |
| | H26~H33 | H31~H35 | H26~H32 |
| CDR H2 | H51~H56 | H50~H65 | H52~H56 |
| CDR H3 | H93~H102 | H95~H102 | H95~H102 |
| CDR L1 | L27~L32 | L24~L34 | L24~L34 |
| CDR L2 | L50~L51 | L50~L56 | L50~L56 |
| CDR L3 | L89~L97 | L89~L97 | L89~L97 |

Thus, the CDR sequence of the antibody according to the present invention has the sequence shown in Table 3 below when using different numbering schemes in addition to the IMGT numbering scheme (FIG. 16).

TABLE 3

CDR sequence (region) of antibody according to the present invention depending on numbering scheme

| CDR | IMGT | Kabat | Chothia |
|---|---|---|---|
| CDR H1 | GGTFSSYA (SEQ ID NO: 1) | SYAIS (SEQ ID NO: 22) | GGTFSSY (SEQ ID NO: 29) |

TABLE 3-continued

CDR sequence (region) of antibody according to the present invention depending on numbering scheme

| CDR | IMGT | Kabat | Chothia |
|---|---|---|---|
| CDR H2 | IIPILGIA (SEQ ID NO: 2) | RIIPILGIANYA (SEQ ID NO: 23) | IPILGI (SEQ ID NO: 30) |
| CDR H3 | ARSGYSYAYGSFDY (SEQ ID NO: 3) | SGYSYAYGSFDY (SEQ ID NO: 24) | SGYSYAYGSFDY (SEQ ID NO: 24) |
| | ARSGYGYAYGSFDY (SEQ ID NO: 11) | SGYGYAYGSFDY (SEQ ID NO: 25) | SGYGYAYGSFDY (SEQ ID NO: 25) |
| CDR L1 | GPTIGAGYD (SEQ ID NO: 5) | TGPTIGAGYDVH (SEQ ID NO: 26) | TGPTIGAGYDVH (SEQ ID NO: 26) |
| | GQTIGAGYD (SEQ ID NO: 13) | TGQTIGAGYDVH (SEQ ID NO: 27) | TGQTIGAGYDVH (SEQ ID NO: 27) |
| CDR L2 | GNL (SEQ ID NO: 6) | GNLNRPS (SEQ ID NO: 28) | GNLNRPS (SEQ ID NO: 28) |
| CDR L3 | QSYDSRLGVV (SEQ ID NO: 7) | QSYDSRLGVV (SEQ ID NO: 7) | QSYDSRLGVV (SEQ ID NO: 7) |

In one embodiment, the antibody according to the invention exhibits cross-reactivity to humans and mice as well as in humans and mammals other than humans. Specifically, the mammals other than humans may be monkeys or dogs (FIG. 17). As used therein, the term "phage display" is a technique for displaying a variant polypeptide as a fusion protein with at least a portion of an envelope protein on the surface of a phage, for example a filamentous phage particle. The usefulness of phage display lies in the fact that it may rapidly and efficiently classify sequences that bind to target antigens with high affinity in large libraries of randomized protein variants. Displaying peptide and protein libraries on phages has been used to screen millions of polypeptides in order to identify polypeptides having specific binding properties.

A phage display technique has proven to be a powerful tool for producing and selecting novel proteins that bind to specific ligands (e.g. antigens). Using a phage display technique, large libraries of protein variants may be produced, and sequences that bind with high affinity to target antigens may be rapidly classified. A nucleic acid encoding the variant polypeptide is fused with a nucleic acid sequence encoding a viral envelope protein, for example, a gene III protein or a gene VIII protein. A monovalent phage display system, in which a nucleic acid sequence encoding a protein or polypeptide is fused with a nucleic acid sequence encoding a portion of a gene III protein, has been developed. In the monovalent phage display system, a fused gene is expressed at a low level and a wild-type gene III protein is also expressed, so particle infectivity is maintained.

Demonstrating the expression of peptides on the surface of the filamentous phage and the expression of functional antibody fragments in the periplasm of E. coli is important in the development of antibody phage display libraries. Libraries of antibodies or antigen-binding polypeptides have been prepared in a number of ways, for example, through methods of altering a single gene by inserting a random DNA sequence or of cloning related gene sequences. The libraries may be screened for the expression of antibodies or antigen-binding proteins having desired characteristics.

The phage display technique has several advantages over typical hybridoma and recombinant methods for producing antibodies having desired characteristics. This technique allows the production of large antibody libraries having various sequences within a short time without using animals. The production of hybridomas or humanized antibodies may require a production period of several months. Moreover, since immunity is not required, the phage antibody library may produce antibodies against antigens that are toxic or have low antigenicity. The phage antibody libraries may be used to produce and identify novel therapeutic antibodies.

Techniques for producing human antibodies from immunized or non-immunized humans, germline sequences, or naive B-cell Ig repertoires using phage display libraries may be applied. A variety of lymphoid tissues may be used to prepare unsensitized or non-immunogenic antigen-binding libraries.

A technology capable of identifying and isolating high-affinity antibodies from phage display libraries is important for the isolation of novel therapeutic antibodies. The isolation of high-affinity antibodies from the libraries may depend on the size of the libraries, production efficiency in bacterial cells, and diversity of the libraries. The size of the libraries is reduced by improper folding of the antibody or antigen-binding protein and inefficient production due to the presence of the stop codon. Expression in bacterial cells may be inhibited when the antibody or antigen-binding domain does not fold properly. Expression may be improved by alternately mutating residues on the surface of the variable/constant interfaces or at selected CDR residues. The sequence of the framework region is an element for providing proper folding when producing antibody phage libraries in bacterial cells.

For the isolation of high-affinity antibodies, it is important to produce diverse libraries of antibodies or antigen-binding proteins. The CDR3 region has often been found to participate in antigen binding. Since the CDR3 region on the heavy chain varies considerably in size, sequence, and structural conformation, a variety of libraries may be prepared using the same.

Moreover, diversity may be created by randomizing the CDRs of the variable heavy and light chains using all 20 amino acids at each position. The use of all 20 amino acids may result in highly diverse variant antibody sequences, and may increase the chances of identifying novel antibodies.

The antibody or antibody fragment of the present invention may include not only the sequence of the anti-PD-L1 antibody of the present invention, but also biological equivalents thereof, within a range that enables specific recognition of PD-L1. For example, additional modifications may be made to the amino acid sequence of an antibody in order to further improve the binding affinity and/or other biological properties of the antibody. Such modifications include, for example, deletion, insertion, and/or substitution of the amino acid sequence residues of the antibody. The amino acid variations are based on the relative similarity of amino acid side-chain substituents, for example, hydrophobicity, hydrophilicity, charge, size, and the like. Based on analysis of the size, shape and type of amino acid side-chain substituents, all of arginine, lysine and histidine are positively charged residues, alanine, glycine and serine have similar sizes, and phenylalanine, tryptophan and tyrosine have similar shapes. Therefore, based on these considerations, arginine, lysine, and histidine may be regarded as biologically functional equivalents, alanine, glycine, and serine may be regarded as biologically functional equivalents, and phenylalanine, tryptophan, and tyrosine may be regarded as biologically functional equivalents.

Taking into consideration the above-described variations having equivalent biological activity, the antibody of the present invention or the nucleic acid molecule encoding the same is construed as comprising a sequence showing substantial identity to the sequence set forth in the sequence number. When the sequence of the present invention and any other sequences are aligned so as to correspond to each other as much as possible and the aligned sequence is analyzed using an algorithm commonly used in the art, the substantial identity refers to a sequence exhibiting at least 90% homology, preferably at least 95% homology, at least 96% homology, at least 97% homology, at least 98% homology, or at least 99% homology. Alignment methods for sequence comparison are known in the art. The NCBI Basic Local Alignment Search Tool (BLAST) is accessible through NBCI, etc., and may be used in conjunction with sequencing programs such as blastp, blastm, blastx, tblastn and tblastx on the Internet. BLAST is available at www.ncbi.nlm.nih.gov/BLAST/. A method for comparing sequence homology using this program may be found at www.ncbi.nlm.nih.gov/BLAST/blast_help.html.

Based thereon, the antibody of the present invention or the antigen-binding fragment thereof may have 90%, 91%, 92%, 93%, 94%, 95%, 96%, 97%, 98%, 99%, or higher homology with a specified sequence or all of the sequences described in the specification. Such homology may be determined through sequence comparison and/or alignment using methods known in the art. For example, the percentage sequence homology of a nucleic acid or protein of the present invention may be determined using a sequence comparison algorithm (i.e. BLAST or BLAST 2.0), manual alignment, or visual inspection.

In another aspect, the present invention pertains to a nucleic acid encoding the antibody or the antigen-binding fragment thereof.

An antibody or an antigen-binding fragment thereof may be recombinantly produced by isolating a nucleic acid encoding the antibody of the present invention or the antigen-binding fragment thereof. The nucleic acid is isolated and inserted into a replicable vector for further cloning (DNA amplification) or further expression. In still another aspect, based thereon, the present invention pertains to a vector comprising the nucleic acid.

As used herein, the term "nucleic acid" has a meaning comprehensively encompassing DNA (gDNA and cDNA) and RNA molecules, and nucleotides, which are the basic building blocks of nucleic acids, include natural nucleotides as well as analogues in which sugar or base regions are modified. The sequence of the nucleic acid encoding the heavy-chain and light-chain variable regions of the present invention may be modified. Such modification includes addition, deletion, or non-conservative or conservative substitution of nucleotides.

DNA encoding the antibody is easily isolated or synthesized using typical procedures (e.g. using an oligonucleotide probe capable of specifically binding to DNA encoding the heavy and light chains of the antibody). Many vectors are commercially available. A vector component generally includes, but is not limited to, at least one selected from among a signal sequence, an origin of replication, at least one marker gene, an enhancer element, a promoter, and a transcription termination sequence.

As used herein, the term "vector" refers to means for expressing a target gene in a host cell, comprising a plasmid vector, a cosmid vector, a viral vector such as bacteriophage vector, adenoviral vector, retroviral vector or adeno-associated viral vector, and the like. In the vector, the nucleic acid encoding the antibody is operably linked with a promoter.

As used herein, the term "operably linked" means a functional linkage between a nucleic acid expression control sequence (e.g. a promoter, a signal sequence, or an array of transcriptional regulator binding sites) and a different nucleic acid sequence, whereby the control sequence serves to control the transcription and/or translation of the different nucleic acid sequence.

When using a prokaryotic cell as a host, a strong promoter capable of propagating transcription (e.g. a tac promoter, lac promoter, lacUV5 promoter, lpp promoter, pLz promoter, pRz promoter, rac5 promoter, amp promoter, recA promoter, SP6 promoter, trp promoter, or T7 promoter), a ribosome-binding site for initiation of translation, and a transcription/translation termination sequence are generally included. In addition, for example, when a eukaryotic cell is used as a host, a promoter derived from the genome of a mammalian cell (e.g. a metallothionine promoter, β-actin promoter, human hemoglobin promoter or human muscle creatine promoter) or a promoter derived from mammalian viruses (e.g. an adenovirus late promoter, vaccinia virus 7.5K promoter, SV40 promoter, cytomegalovirus (CMV) promoter, tk promoter of HSV, mouse mammary tumor virus (MMTV) promoter, LTR promoter of HIV, promoter of Moloney virus, promoter of Epstein-Barr virus (EBV), or promoter of Rous sarcoma virus (RSV)) may be used, and generally has a polyadenylation sequence as a transcription termination sequence.

In some cases, the vector may be fused with another sequence in order to facilitate purification of the antibody expressed therefrom. Examples of the sequence that is fused include glutathione S-transferase (Pfizer Inc., USA), maltose-binding protein (New England Biolabs, USA), FLAG® peptide tag (MilliporeSigma, USA), and 6×His (hexahistidine; QIAGEN LLC, USA).

The vector contains, as a selective marker, an antibiotic resistance gene that is commonly used in the art, for example, a gene conferring resistance to ampicillin, gentamicin, carbenicillin, chloramphenicol, streptomycin, kanamycin, geneticin, neomycin, or tetracycline.

In yet another aspect, the present invention pertains to a cell transfected with the vector described above. Examples of the cell used to produce the antibody of the present invention may include, but are not limited to, prokaryotic cells, yeast cells, and higher eukaryotic cells.

Strains belonging to the genus *Bacillus*, such as *Escherichia coli, Bacillus subtilis*, and *Bacillus thuringiensis*, and prokaryotic host cells such as *Streptomyces, Pseudomonas* (e.g. *Pseudomonas putida*), *Proteus mirabilis*, and *Staphylococcus* (e.g. *Staphylococcus carnosus*) may be used.

Here, animal cells are of greatest interest, and examples of useful host cell lines may include, but are not limited to, COS-7, BHK, CHO, CHO-S, CHOK1, GS-CHO, DXB-11, DG-44, CHO/-DHFR, CV1, HEK293, TM4, VERO, HELA, MDCK, BRL 3A, W138, Hep G2, SK-Hep, MMT, TRI, MRC 5, FS4, 3T3, RIN, A549, PC12, K562, PER.C6, SP2/0, NS-0, U2OS, and HT1080.

In still yet another aspect, the present invention pertains to a method of producing the antibody or the antigen-binding fragment thereof comprising (a) culturing the cells described above and (b) purifying an antibody or an antigen-binding fragment thereof from the cultured cells.

The cells may be cultured in various media. Any commercially available medium may be used as a culture medium without limitation. All other essential supplements known to those skilled in the art may be contained in appropriate concentrations. Culture conditions, such as temperature, pH, etc., are those already used for the host cells selected for expression, as will be apparent to those skilled in the art.

For the purification of the antibody or the antigen-binding fragment thereof, impurities may be removed through, for example, centrifugation or ultrafiltration, and the resultant product may be purified using, for example, affinity chromatography. Other additional purification techniques may be used, such as anion or cation exchange chromatography, hydrophobic interaction chromatography, hydroxyapatite chromatography, and the like.

In a further aspect, the present invention pertains to a composition for preventing or treating cancer comprising the antibody described above as an active ingredient.

The present invention may address, for example, a pharmaceutical composition for the prevention or treatment of cancer comprising (a) a pharmaceutically effective amount of the antibody to PD-L1 or the antigen-binding fragment thereof according to the present invention and (b) a pharmaceutically acceptable carrier. In addition, the present invention pertains to a method of preventing or treating cancer comprising administering the antibody to PD-L1 or the antigen-binding fragment thereof according to the present invention in an effective amount required for a patient.

Since the composition uses the aforementioned anti-PD-L1 antibody or the antigen-binding fragment thereof according to the present invention as an active ingredient, a description of common contents therebetween is omitted.

Binding of PD-L1 to PD-1 negatively modulates T cell antigen-specific responses important for tolerance and prevention of autoimmune and immunopathology. However, excessive PD-L1/PD-1 interactions, which may be induced by chronic antigenic stimulation, may result in suppression of T cell antigen-specific responses and loss of T cells, which are characteristics of T cell exhaustion. T cell exhaustion is a state of T cell dysfunction that may occur in chronic infections and cancers. It is defined by poor effector function, sustained expression of inhibitory receptors, and a transcriptional state distinct from that of functional effector or memory T cells. Exhaustion interferes with the control of infection and tumor progression.

As demonstrated later with reference to the examples, the antibody or the antigen-binding fragment thereof according to the present invention binds with high affinity to PD-L1 and thus inhibits the formation of a PD-1/PD-L1 complex, and thereby may be usefully used to treat cancer that induces T cell exhaustion that evades anti-tumor T cell activity.

The present invention also pertains to a composition for combination therapy for preventing or treating cancer by administering the antibody or the antigen-binding fragment thereof according to the present invention in combination with another anticancer agent.

The present invention may address, for example, a composition for combination therapy for preventing or treating cancer comprising (a) a pharmaceutically effective amount of the antibody to PD-L1 or the antigen-binding fragment thereof according to the present invention and (b) a pharmaceutically acceptable carrier. The present invention also pertains to a combination therapy method for the prevention or treatment of cancer comprising administering the antibody to PD-L1 or the antigen-binding fragment thereof according to the present invention in an effective amount required for a patient.

Since the composition uses the aforementioned anti-PD-L1 antibody or antigen-binding fragment thereof according to the present invention as an active ingredient, a description of common contents therebetween is omitted.

As described above, the antibody according to the present invention is used in combination with another anticancer agent, thus making it possible to effectively target tumor cells overexpressing PD-L1 and to increase anti-tumor T cell activity, thereby enhancing the immune response targeting the tumor cells.

Other anti-neoplastic or immunogenic agents [(e.g. attenuated cancer cells, tumor antigens (including recombinant proteins, peptides and carbohydrate molecules), antigen-presenting cells, for example, dendritic cells pulsed with tumor-derived antigens or nucleic acids, immune-stimulating cytokines (e.g. IL-2, IFNα2, GM-CSF), and cells transfected with genes encoding immune-stimulating cytokines (which include, but are not limited to, for example, GM-CSF)], cells containing an antibody targeting a cancer antigen (e.g. CAR-T, CAR-NK), immunosuppressive inhibitors of the tumor microenvironment (e.g. IDO inhibitor), an oncolytic virus, standard cancer therapy (e.g. chemotherapy, radiation therapy or surgery), or other cancer-associated antigens may be used.

Moreover, the antibody or the antigen-binding fragment thereof according to the present invention may be used along with another antibody (examples of an antibody other than the PD-L1 antibody may include, but are not limited to, antibodies to VEGF, EGFR, Her2/neu, VEGF receptor, other growth factor receptors, CD20, CD40, CTLA-4, OX-40, 4-1BB, and ICOS).

Specifically, the antibody that may be used along with the antibody or the antigen-binding fragment thereof according to the present invention may be used without limitation, so long as it is an antibody capable of specifically binding to an antigen associated with cancer or autoimmune disease, and examples of such an antigen may include, but are not limited to, 4-1BB, integrin, angiopoietin, angiopoietin analogue 3, B-cell-activating factor (BAFF), B7-H3, CCR4, CD3, CD4, CD6, CD11a, CD19, CD20, CD22, CD30, CD33, CD38, CD40, CD52, CD62, CD79b, CD80, CGRP, OX-40, ICOS, Claudin-18, CTLA4, DLL3, EGF receptor, Fc receptor, FGF23, folate receptor, GD2, GM-CSF, HER2, Her2/neu, HER3, VEGF, VEGF receptor, interferon receptor, interferon gamma, IgE, IGF-1 receptor, interleukin 1, interleukin 2 receptor, interleukin 4 receptor, interleukin 5, interleukin 5 receptor, interleukin 6, interleukin 6 receptor, interleukin 7, interleukin 12/23, interleukin 13, interleukin 17A, interleukin 17 receptor A, interleukin 31 receptor, interleukin 36 receptor, LAG3, LFA3, NGF, PVSK9, PD-1, PD-L1, RANK-L, SLAMF7, and tissue factor.

More specifically, examples of the antibody that binds to the antigen described above include:
 antibodies to 4-1BB, such as utomilumab;
 antibodies to integrin, such as natalizumab, etrolizumab, vedolizumab, and bimagrumab;
 antibodies to amyloid beta, such as bapineuzumab, crenezumab, solanezumab, aducanumab, and gantenerumab;
 antibodies to angiopoietin, such as AMG 780;
 antibodies to angiopoietin analogue 3, such as evinacumab;
 antibodies to B-cell-activating factor (BAFF), such as tabalumab, lanalumab, and belimumab;
 antibodies to B7-H3, such as omburtamab;
 antibodies to CCR4, such as mogamulizumab;
 antibodies to CD3, such as otelixizumab, teplizumab, muromonab, tebentafusp, which is a bispecific antibody to GP100 and CD3, blinatumomab, which is a bispecific antibody to CD19 and CD3, and REGN1979, which is a bispecific antibody to CD20 and CD3;
antibodies to CD4, such as ibalizumab and zanolimumab;
antibodies to CD6, such as itolizumab;
antibodies to CD11a, such as efalizumab;
antibodies to CD19, such as inebilizumab, tafasitamab, and loncastuximab tesirine as an ADC;
antibodies to CD20, such as ocrelizumab, ublituximab, obinutuzumab, ofatumumab, rituximab, tositumomab, and ibritumomab tiuxetan as an ADC;
antibodies to CD22, such as epratuzumab, and as ADCs, inotuzumab ozogamicin and moxetumomab pasudotox;
ADCs to CD30, such as brentuximab vedotin;
ADCs to CD33, such as vadastuximab talirine and gemtuzumab ozogamicin;
antibodies to CD38, such as daratumumab and isatuximab;
antibodies to CD52, such as alemtuzumab;
antibodies to CD62, such as crizanlizumab;
ADCs to CD79b, such as polatuzumab vedotin;
antibodies to CD80, such as galiximab;
antibodies to CGRP, such as eptinezumab, fremanezumab, galcanezumab, and erenumab;
antibodies to Claudin-18, such as zolbetuximab;
antibodies to CTLA4, such as tremelimumab, zalifrelimab, and ipilimumab;
ADCs to DLL3, such as rovalpituzumab tesirine;
antibodies to EGF receptor, such as cetuximab, depatuxizumab, zalutumumab, necitumumab, and panitumumab;
antibodies to Fc receptor, such as nipocalimab and rozanolixizumab;
antibodies to FGF23, such as burosumab;
antibodies to folate receptor, such as farletuzumab, and mirvetuximab soravtansine as an ADC;
antibodies to GD2, such as dinutuximab and naxitamab;
antibodies to GM-CSF, such as otilimab;
antibodies to HER2, such as margetuximab, pertuzumab, trastuzumab, and as ADCs, trastuzumab deruxtecan, trastuzumab emtansine, and trastuzumab duocarmazine;
antibodies to HER3, such as patritumab;
antibodies to interferon receptor, such as anifrolumab;
antibodies to interferon gamma, such as emapalumab;
antibodies to IgE, such as ligelizumab and omalizumab;
antibodies to IGF-1 receptor, such as dalotuzumab, figitumumab, and teprotumumab;
antibodies to interleukin 1, such as gevokizumab and canakinumab;
antibodies to interleukin 2 receptor, such as daclizumab and basiliximab;
antibodies to interleukin 4 receptor, such as dupilumab;
antibodies to interleukin 5, such as mepolizumab and reslizumab;
antibodies to interleukin 5 receptor, such as benralizumab;
antibodies to interleukin 6, such as clazakizumab, olokizumab, sirukumab, and siltuximab;
antibodies to interleukin 6 receptor, such as sarilumab, satralizumab, tocilizumab, and REGN88;
antibodies to interleukin 7, such as secukinumab;
antibodies to interleukin 12/23, such as ustekinumab and briakinumab;
antibodies to interleukin 13, such as lebrikizumab and tralokinumab;
antibodies to interleukin 17A, such as ixekizumab and bimekizumab;
antibodies to interleukin 17 receptor A, such as brodalumab;
antibodies to interleukin 23, such as brazikumab, guselkumab, risankizumab, tildrakizumab, and mirikizumab;
antibodies to interleukin 31 receptor, such as nemolizumab;
antibodies to interleukin 36 receptor, such as spesolimab;
antibodies to LAG3, such as relatlimab;
antibodies to NASP2, such as narsoplimab;
antibodies to NGF, such as fasinumab and tanezumab;
antibodies to PVSK9, such as alirocumab, evolocumab, and bococizumab;
antibodies to PD-1, such as lambrolizumab, balstilimab, camrelizumab, cemiplimab, dostarlimab, prolgolimab, sintilimab, spartalizumab, tislelizumab, pembrolizumab, and nivolumab;
antibodies to PD-L1, such as atezolizumab, avelumab, envafolimab, durvalumab, and bintrafusp alpha, which is a bispecific antibody to TGF-beta and PD-L1;
antibodies to RANK-L, such as denosumab;
antibodies to SLAMF7, such as elotuzumab;
antibodies to tissue factor, such as concizumab and marstacimab;
antibodies to TNF, particularly TNFα, such as infliximab, adalimumab, golimumab, certolizumab pegol, which is an antibody fragment, and ozoralizumab, which is a bispecific antibody to TNF and albumin;
antibodies to VEGF, such as brolucizumab, ranibizumab, bevacizumab, and faricimab, which is a bispecific antibody to VEGF and Ang2; and
antibodies to VEGF receptor, such as ramucirumab,
but are not limited thereto.

Cancer, which is a disease to which the composition is applied, typically includes cancer that responds to immunotherapy and cancer that has not hitherto been implicated in immunotherapy. Non-limiting examples of the cancer to be treated may include melanoma (e.g. metastatic malignant melanoma), kidney cancer (e.g. clear cell carcinoma), prostate cancer (e.g. hormone-refractory prostate adenocarcinoma), pancreatic adenocarcinoma, breast cancer, colon cancer, lung cancer (e.g. non-small cell lung cancer), esophageal cancer, head and neck squamous cell carcinoma, liver cancer, ovarian cancer, cervical cancer, thyroid cancer, glioblastoma, glioma, leukemia, lymphoma, and other neoplasms. Additionally, the present invention encompasses refractory or relapsed cancer for which growth may be inhibited using the antibody of the present invention.

The antibody or the antibody fragment according to the present invention may also be used alone or in combination with a vaccine to stimulate an immune response to pathogens, toxins, and self-antigens. The antibody or the antigen-binding fragment thereof may be used to stimulate an immune response to viruses that infect humans, comprising but not limited to, for example, human immunodeficiency virus, hepatitis virus classes A, B and C, Epstein-Barr virus, human cytomegalovirus, human papilloma virus, and herpes virus. The antibody or the antigen-binding fragment thereof may be used to stimulate an immune response to infection of bacterial or fungal parasites, and other pathogens.

The present invention also pertains to a composition comprising the antibody or the antigen-binding fragment thereof according to the present invention and useful bacteria. The useful bacteria are used as bacteria or probiotics having anticancer efficacy, and examples thereof may include, but are not limited to, *Anaerococcus, Anaerostipes, Alistipes, Akkermansia, Bacillus, Bacteroides, Bifidobacte-*

*rium, Blautia, Capnocytophaga, Clostridium, Collinsella, Desulfovibrio, Dorea, Enterococcus, Escherichia, Eubacterium, Faecalibacterium, Fusobacterium, Gardnerella, Gemmiger, Klebsiella, Lactobacillus, Leuconostoc, Moryella, Paraprevotella, Parabacteroides, Phascolarctobacterium, Porphyromonas, Prevotella, Pseudobutyrivibrio, Roseburia, Rothia, Ruminococcus, Shigella, Streptococcus, Veillonella, Weissella*, and the like.

The pharmaceutically acceptable carrier contained in the composition of the present invention may include those commonly used in formulations, for example lactose, dextrose, sucrose, sorbitol, mannitol, starch, acacia gum, calcium phosphate, alginate, gelatin, calcium silicate, microcrystalline cellulose, polyvinylpyrrolidone, water, syrup, methyl cellulose, methylhydroxybenzoate, propylhydroxybenzoate, talc, magnesium stearate, and mineral oil, but is not limited thereto. The composition of the present invention may further include a lubricant, a wetting agent, a sweetening agent, a flavoring agent, an emulsifying agent, a suspending agent, a preservative, and the like, in addition to the above components.

The pharmaceutical composition of the present invention may be administered orally or parenterally, and examples of parenteral administration may include intravenous injection, subcutaneous injection, intramuscular injection, intraperitoneal injection, endothelial administration, topical administration, intranasal administration, intrapulmonary administration, intrarectal administration, etc.

When administered orally, the protein or peptide is digestible, and therefore the oral composition has to be formulated such that an active agent is coated or is protected from degradation in the stomach. Also, the pharmaceutical composition may be administered using any device capable of transporting the active agent to target cells.

The appropriate dose of the composition according to the present invention may vary depending on factors, such as the formulation method, administration mode, patient's age, weight, and gender, morbidity, food, time of administration, route of administration, excretion rate, and response sensitivity, and the dose that is effective for the desired treatment or prevention may be easily determined and prescribed by ordinarily skilled doctors. For example, the daily dose of the pharmaceutical composition of the present invention is 0.0001-100 mg/kg. As used herein, the term "pharmaceutically effective amount" refers to an amount sufficient to prevent or treat cancer.

The pharmaceutical composition of the present invention may be formulated into a unit dosage form or may be prepared in a multidose container using a pharmaceutically acceptable carrier and/or excipient in accordance with a method that may be easily carried out by a person of ordinary skill in the art to which the present invention belongs. Here, the formulation may take the form of a solution, suspension or emulsion in an oily or aqueous medium, or may take the form of an extract, powder latinor-pulvis, suppository, powder, granule, tablet, or capsule, and may further include a dispersant or stabilizer.

The composition of the present invention may be administered alone as a therapeutic agent, or may be administered in combination with another therapeutic agent, and may be administered sequentially or simultaneously with conventional therapeutic agents.

In still a further aspect, the present invention provides an antibody-drug conjugate in which a drug is conjugated to the anti-PD-L1 antibody or the antigen-binding fragment thereof according to the present invention, and a pharmaceutical composition comprising the same. In addition, the present invention provides a method of treating a tumor using the antibody-drug conjugate in which the drug is conjugated to the anti-PD-L1 antibody or the antigen-binding fragment thereof and the pharmaceutical composition comprising the same.

The anti-PD-L1 antibody or the antigen-binding fragment thereof may be bound to a drug via a linker. The linker is a site linking the anti-PD-L1 antibody or the antigen-binding fragment thereof to the drug. For example, the linker is cleavable under intracellular conditions, and specifically, the drug may be released from the antibody through cleavage of the linker in the intracellular environment.

The linker may be cleaved by a cleaving agent present in the intracellular environment, for example a lysosome or endosome, and may be, for example, a peptide linker that may be cleaved by an intracellular peptidase or protease enzyme such as a lysosomal or endosomal protease. Typically, a peptide linker has a length of at least two amino acids. The cleaving agent may include cathepsin B, cathepsin D, and plasmin, and is able to hydrolyze the peptide to release the drug into the target cells.

The peptide linker may be cleaved by thiol-dependent protease cathepsin-B, which is overexpressed in cancer tissues, and, for example, a Phe-Leu or Gly-Phe-Leu-Gly (SEQ ID NO: 86) linker may be used. Moreover, the peptide linker may be cleavable by, for example, an intracellular protease, and may be a Val-Cit linker or a Phe-Lys linker.

In one embodiment, the cleavable linker is pH-sensitive, and may be sensitive to hydrolysis at a certain pH value. In general, pH-sensitive linkers may be hydrolyzed under acidic conditions. Examples of acid-labile linkers capable of being hydrolyzed in the lysosome may include hydrazones, semicarbazones, thiosemicarbazones, cis-aconitic amides, orthoesters, acetals, ketal, and the like.

In another embodiment, the linker may be cleaved under reducing conditions, and may include, for example, a disulfide linker. Various disulfide bonds may be formed using SATA (N-succinimidyl-S-acetylthioacetate), SPDP (N-succinimidyl-3-(2-pyridyldithio)propionate), SPDB (N-succinimidyl-3-(2-pyridyldithio)butyrate), and SMPT (N-succinimidyl-oxycarbonyl-alpha-methyl-alpha-(2-pyridyl-dithio) toluene).

The drug and/or the drug-linker may be randomly conjugated via lysine of the antibody or via cysteine exposed upon reduction of a disulfide bond chain. In some cases, a linker-drug may be bound via a genetically engineered tag, for example, cysteine present in a peptide or protein. The genetically engineered tag, for example a peptide or protein, may include an amino acid motif that may be recognized by, for example, isoprenoid transferase. The peptide or protein may have a deletion at the carboxy terminus of the peptide or protein, or may have an addition through a covalent bond of a spacer unit to the carboxyl (C) terminus of the peptide or protein.

Also, the linker may be, for example, a non-cleavable linker, and the drug may be released through only a single step of antibody hydrolysis to thus produce, for example, an amino-acid/linker/drug complex. This type of linker may be a thioether group or a maleimidocaproyl group, and may remain stable in the blood.

The drug in the antibody-drug conjugate may be an agent exhibiting a pharmacological effect, and may be bound to an antibody, and specific examples thereof may include a chemotherapeutic agent, a toxin, microRNA (miRNA), siRNA, shRNA, and a radioactive isotope. The chemotherapeutic agent may be, for example, a cytotoxic agent or an immunosuppressive agent. Specifically, it may include a microtubulin inhibitor, a mitotic inhibitor, a topoisomerase inhibitor, or a chemotherapeutic agent capable of functioning as a DNA intercalator. It may also include an immunomodulatory compound, an anticancer agent, an antiviral agent, or combinations thereof.

Such a drug may be at least one selected from the group consisting of, for example, maytansinoid, auristatin, aminopterin, actinomycin, bleomycin, talisomycin, camptothecin, N8-acetylspermidine, 1-(2 chloroethyl)-1,2-dimethyl sulfonyl hydrazide, esperamicin, etoposide, 6-mercaptopurine, dolastatin, trichothecene, calicheamicin, taxol, taxane, paclitaxel, docetaxel, methotrexate, vincristine, vinblastine, doxorubicin, melphalan, mitomycin A, mitomycin C, chlorambucil, duocarmycin, L-asparaginase, mercaptopurine, thioguanine, hydroxyurea, cytarabine, cyclophosphamide, ifosfamide, nitrosourea, cisplatin, carboplatin, mitomycin, dacarbazine, procarbazine, topotecan, nitrogen mustard, cytoxan, 5-fluorouracil, CNU (bischloroethylnitrosourea), irinotecan, idarubicin, daunorubicin, dactinomycin, plicamycin, mitoxantrone, asparaginase, vinorelbine, chlorambucil, melphalan, carmustine, lomustine, busulfan, treosulfan, dacarbazine, teniposide, topotecan, 9-aminocamptothecin, crisnatol, trimetrexate, mycophenolic acid, tiazofurin, ribavirin, EICAR (5-ethynyl-1-beta-dribofuranosylimidazole-4-carboxamide), hydroxyurea, deferoxamine, floxuridine, doxifluridine, raltitrexed, cytarabine (ara C), cytosine arabinoside, fludarabine, tamoxifen, raloxifene, megestrol, goserelin, leuprolide acetate, flutamide, bicalutamide, EB1089, CB1093, KH1060, verteporfin, phthalocyanine, photosensitizer Pe4, demethoxy-hypocrellin A, interferon-α, interferon-γ, tumor necrosis factor, gemcitabine, Velcade, Revlimid, thalidomide, lovastatin, 1-methyl-4-phenylpyridinium ion, staurosporine, actinomycin D, dactinomycin, bleomycin A2, bleomycin B2, peplomycin, epirubicin, pirarubicin, zorubicin, mitoxantrone, verapamil, thapsigargin, nucleases, and toxins derived from bacteria or animals and plants, but is not limited thereto.

In yet a further aspect, the present invention provides a bispecific antibody in which the anti-PD-L1 antibody or the antigen-binding fragment thereof according to the present invention is bound to an antibody that binds to another antigen.

The antibody forming the bispecific antibody along with the anti-PD-L1 antibody or the antigen-binding fragment thereof according to the present invention may be used without limitation, so long as it is an antibody capable of binding specifically to an antigen associated with cancer or autoimmune disease. Examples of such an antigen may include, but are not limited to, 4-1BB, integrin, angiopoietin, angiopoietin analogue 3, B-cell-activating factor (BAFF), B7-H3, CCR4, CD3, CD4, CD6, CD11a, CD19, CD20, CD22, CD30, CD33, CD38, CD40, CD52, CD62, CD79b, CD80, CGRP, OX-40, ICOS, Claudin-18, CTLA4, DLL3, EGF receptor, Fc receptor, FGF23, folate receptor, GD2, GM-CSF, HER2, Her2/neu, HER3, VEGF, VEGF receptor, interferon receptor, interferon gamma, IgE, IGF-1 receptor, interleukin 1, interleukin 2 receptor, interleukin 4 receptor, interleukin 5, interleukin 5 receptor, interleukin 6, interleukin 6 receptor, interleukin 7, interleukin 12/23, interleukin 13, interleukin 17A, interleukin 17 receptor A, interleukin 31 receptor, interleukin 36 receptor, LAG3, LFA3, NGF, PVSK9, PD-1, PD-L1, RANK-L, SLAMF7, tissue factor, TGF-β, and the like.

More specifically, examples of the antibody that binds to the antigen described above include:
antibodies to 4-1BB, such as utomilumab;
antibodies to integrin, such as natalizumab, etrolizumab, vedolizumab, and bimagrumab;
antibodies to amyloid beta, such as bapineuzumab, crenezumab, solanezumab, aducanumab, and gantenerumab;
antibodies to angiopoietin, such as AMG 780;
antibodies to angiopoietin analogue 3, such as evinacumab;
antibodies to B-cell-activating factor (BAFF), such as tabalumab, lanalumab, and belimumab;
antibodies to B7-H3, such as omburtamab;
antibodies to CCR4, such as mogamulizumab;
antibodies to CD3, such as otelixizumab, teplizumab, muromonab, tebentafusp, which is a bispecific antibody to GP100 and CD3, blinatumomab, which is a bispecific antibody to CD19 and CD3, and REGN1979, which is a bispecific antibody to CD20 and CD3;
antibodies to CD4, such as ibalizumab and zanolimumab;
antibodies to CD6, such as itolizumab;
antibodies to CD11a, such as efalizumab;
antibodies to CD19, such as inebilizumab, tafasitamab, and loncastuximab tesirine as an ADC;
antibodies to CD20, such as ocrelizumab, ublituximab, obinutuzumab, ofatumumab, rituximab, tositumomab, and ibritumomab tiuxetan as an ADC;
antibodies to CD22, such as epratuzumab, and as ADCs, inotuzumab ozogamicin and moxetumomab pasudotox;
ADCs to CD30, such as brentuximab vedotin;
ADCs to CD33, such as vadastuximab talirine and gemtuzumab ozogamicin;
antibodies to CD38, such as daratumumab and isatuximab;
antibodies to CD52, such as alemtuzumab;
antibodies to CD62, such as crizanlizumab;
ADCs to CD79b, such as polatuzumab vedotin;
antibodies to CD80, such as galiximab;
antibodies to CGRP, such as eptinezumab, fremanezumab, galcanezumab, and erenumab;
antibodies to Claudin-18, such as zolbetuximab;
antibodies to CTLA4, such as tremelimumab, zalifrelimab, and ipilimumab;
ADCs to DLL3, such as rovalpituzumab tesirine;
antibodies to EGF receptor, such as cetuximab, depatuxizumab, zalutumumab, necitumumab, and panitumumab;
antibodies to Fc receptor, such as nipocalimab and rozanolixizumab;
antibodies to FGF23, such as burosumab;
antibodies to folate receptor, such as farletuzumab, and mirvetuximab soravtansine as an ADC;
antibodies to GD2, such as dinutuximab and naxitamab;
antibodies to GM-CSF, such as otilimab;
antibodies to HER2, such as margetuximab, pertuzumab, trastuzumab, and as ADCs, trastuzumab deruxtecan, trastuzumab emtansine, and trastuzumab duocarmazine;
antibodies to HER3, such as patritumab;
antibodies to interferon receptor, such as anifrolumab;
antibodies to interferon gamma, such as emapalumab;
antibodies to IgE, such as ligelizumab and omalizumab;
antibodies to IGF-1 receptor, such as dalotuzumab, figitumumab, and teprotumumab;
antibodies to interleukin 1, such as gevokizumab and canakinumab;
antibodies to interleukin 2 receptor, such as daclizumab and basiliximab;

antibodies to interleukin 4 receptor, such as dupilumab;
antibodies to interleukin 5, such as mepolizumab and reslizumab;
antibodies to interleukin 5 receptor, such as benralizumab;
antibodies to interleukin 6, such as clazakizumab, olokizumab, sirukumab, and siltuximab;
antibodies to interleukin 6 receptor, such as sarilumab, satralizumab, tocilizumab, and REGN88;
antibodies to interleukin 7, such as secukinumab;
antibodies to interleukin 12/23, such as ustekinumab and briakinumab;
antibodies to interleukin 13, such as lebrikizumab and tralokinumab;
antibodies to interleukin 17A, such as ixekizumab and bimekizumab;
antibodies to interleukin 17 receptor A, such as brodalumab;
antibodies to interleukin 23, such as brazikumab, guselkumab, risankizumab, tildrakizumab, and mirikizumab;
antibodies to interleukin 31 receptor, such as nemolizumab;
antibodies to interleukin 36 receptor, such as spesolimab;
antibodies to LAG3, such as relatlimab;
antibodies to NASP2, such as narsoplimab;
antibodies to NGF, such as fasinumab and tanezumab;
antibodies to PVSK9, such as alirocumab, evolocumab, and bococizumab;
antibodies to PD-1, such as lambrolizumab, balstilimab, camrelizumab, cemiplimab, dostarlimab, prolgolimab, sintilimab, spartalizumab, tislelizumab, pembrolizumab, and nivolumab;
antibodies to PD-L1, such as atezolizumab, avelumab, envafolimab, and durvalumab;
antibodies to RANK-L, such as denosumab;
antibodies to SLAMF7, such as elotuzumab;
antibodies to tissue factor, such as concizumab and marstacimab;
antibodies to TNF, particularly TNFα, such as infliximab, adalimumab, golimumab, certolizumab pegol, which is an antibody fragment, and ozoralizumab, which is a bispecific antibody to TNF and albumin;
antibodies to VEGF, such as brolucizumab, ranibizumab, bevacizumab, and faricimab, which is a bispecific antibody to VEGF and Ang2; and
antibodies to VEGF receptor, such as ramucirumab,
but are not limited thereto.

A better understanding of the present invention may be obtained through the following examples. These examples are merely set forth to illustrate the present invention, and are not to be construed as limiting the scope of the present invention, as will be apparent to those of ordinary skill in the art.

EXAMPLES

Example 1. PD-L1 Antigen Expression and Purification

Using a vector (Sino Biological) containing a PD-L1 cDNA gene as a template, the fragment containing the extracellular region (Met1-Thr239) from the signal sequence at the N-terminus of the PD-L1 gene was subjected to PCR amplification and inserted into the NheI and SfiI restriction enzyme sites of a pCEP4-Fc vector as a vector for fusion expression of the human Fc fragment, thus constructing a 'pCEP4-PDL1-Fc' vector.

Thereafter, the PD-L1 expression vector was introduced into FREESTYLE™ 293-F cells using FECTOPRO® (Polyplus (Sartorius Group)), which is a cell transfection reagent, according to the transfection method provided by the manufacturer, and culture was carried out for about 6 to 10 days so that the antigen protein was released out of the cells.

The PD-L1 antigen protein released to the cell culture media was purified through an open column purification method using a protein A resin (Amicogen), eluted with citric acid, and then neutralized with 1 M Tris solution at a pH of 9.4. The neutralized antigen protein was purified through a dialysis process 5 times with a 1×PBS buffer, and was used for subsequent experiments.

Example 2. Reamplification of Phage Library

1) The 'phage display' technique was used to select human antibodies binding to PD-L1. Three types of human antibody libraries were used for the selection of human antibody candidates through phage display, and were 1) a naive scFv library reported in 'PNAS, 1999 vol. 96, pp. 6953-6958', 2) a synthetic scFv library reported in 'Molecules and Cells, 2009, vol. 27, pp. 225-235', and 3) an 'LG naive scFv library' developed by LG Life Sciences.
2) For phage display, phages were reamplified from *E. coli* to thus produce scFv-displaying phages. This method was as follows: the library '1)' was produced using the 'Rescue of scFv-displaying phage' method in the paper, the library '2)' was produced according to the 'Library rescue' method mentioned in the paper, and the library '3)' was produced through a separate method, and a detailed description thereof was as follows.
3) 1 vial of phage-containing cells was thawed, seeded into 2 L of 2×YT (containing 1% glucose, 34 µg/ml chloramphenicol, and 5 mM $MgCl_2$), cultured in a shaking incubator at 37° C. until OD600 reached 0.5, mixed with a VCSM13 helper phage at an MOI value of 20, and cultured in an incubator at 37° C. for 45 minutes without shaking to allow complete infection of the helper phage into individual cells.
4) The infected cells were transferred to a 500 ml Sorvall tube and centrifuged at 5000 rpm for 15 minutes, after which the cell pellet was resuspended in 2 L of 2×YT (containing 1 mM IPTG, 34 µg/ml chloramphenicol, 70 µg/ml kanamycin, and 5 mM $MgCl_2$) and then cultured overnight in a shaking incubator (220 rpm) at 30° C., thus producing phages.
5) After overnight cell culture (220 rpm, 30° C.), the cell culture media was centrifuged at 4° C. and 8000 rpm for 20 minutes, the cell culture precipitate was discarded, and the supernatant was added with a PEG/NaCl (20% w/v PEG 6000, 0.25 M NaCl) solution in a volume corresponding to ⅕ of the volume of the supernatant and incubated on ice for about 1 hour to allow the phages to agglomerate and sink, followed by centrifugation at 8000 rpm at 4° C. for 20 minutes to afford a phage pellet. The supernatant was decanted, the phage pellet was resuspended in about 80 ml of PBS to obtain a phage solution sample, and impurities in the phage solution sample were removed using a 0.45 µm syringe filter, thereby completing the preparation of a phage library sample.

Example 3. Phage Panning

1) Using a Dynabeads™ M-270 Epoxy bead available from Dynal, about 10 µg of a PD-L1 antigen protein was coupled to 12.5 µL of beads according to the experimental method provided by the manufacturer to prepare magnetic beads to which the antigen protein was coupled, followed by a blocking reaction through incubation at room temperature for 1 hour in a PBS buffer containing 3% BSA.
2) About $10^{13}$ human antibody expressed on the surface of phages purified through PEG/NaCl precipitation using a syringe filter were suspended in a PBS solution containing 1% BSA and 0.05% Tween and placed in an immuno-tube (Nunc) coated with 12.5 µg/ml of a previously prepared human antibody (Green Cross, 10% IV-Globulin SN injection) sample, followed by a subtraction reaction to remove phages bound to the Fc region (at room temperature for 2 hours).
3) After completion of subtraction, the resulting phage solution was mixed with the magnetic beads to which the antigen protein was coupled, stirred at room temperature for about 2 hours so that the antibody phages capable of binding to the antigen protein were allowed to bind to the magnetic beads, and then placed in a magnetized MACS column (Miltenyi Biotech) to afford antibodies bound to the magnetic beads to which the antigen protein was coupled.
4) During panning, stringency was adjusted so that many high-affinity antibodies could be selected while increasing the number of washing processes, for example, first washing once with 6 ml of PBS, second and third washing two times with 6 ml of PBS, fourth washing three times with 7 ml of PBS, and the like.
5) After washing with the PBS buffer, 700 µl of a 0.25% trypsin solution was injected into a MACS column to fill the column with the trypsin solution, the column was cultured in an incubator at 37° C. for 30 minutes to induce phage elution, and the column was centrifuged at 1,000 rpm for 1 minute to obtain eluted phages, which were then mixed with freshly prepared ER2738 (NEB) E. coli cultured to the extent of OD600=about 0.7-0.8 to induce infection of E. coli with the eluted phages.
6) E. coli infected with the phages was spread on a solid LB plate (containing 1% glucose) including the corresponding antibiotics and cultured overnight in an incubator at 30° C. so that E. coli was able to grow to lawn. After completion of growth, E. coli covering the plate was harvested using a scraper, and the phage particles were reamplified through the method used in Example 2.

Example 4. Selection of Antibody Binding to PD-L1 Antigen Protein Through ELISA and FACS Experiments 1) In order to confirm binding to a PD-L1 antigen protein, periplasmic fractions containing antibody fragments were obtained from about 1,700 bacterial strains expressing individual antibodies, and ELISA and FACS selection experiments were performed.
2) In order to obtain an antibody fragment protein from each strain of E. coli, single-colony bacteria were seeded into a 96-deep-well plate in which about 1 ml of an LB medium was dispensed, cultured in a shaking incubator at 37° C., and then added with 1 mM IPTG when an OD600 value reached about 0.7-0.8, followed by overnight shaking incubation at 30° C. to induce expression of the antibody fragment in the periplasm of E. coli.
3) The next day, in order to extract the periplasmic component, the cultured E. coli was centrifuged (4,000 rpm, 15 minutes, 4° C.), the supernatant was decanted, and E. coli was completely resuspended in 80 µl of an ice-cold 1×TES buffer (20% w/v sucrose, 50 mM Tris, 1 mM EDTA, pH 8.0), allowed to stand on ice for 30 minutes, further added with 120 µl of an ice-cold 0.2×TES buffer, mixed, and allowed to stand for an additional about 30 minutes to induce extraction of the periplasmic component using osmotic pressure. Thereafter, the cells were removed through centrifugation, and the supernatant was used for ELISA and FACS verification experiments as the periplasmic component containing antibody fragments.
4) For the ELISA verification experiment to confirm the binding to the PD-L1 antigen protein, about 100 ng/well of the antigen protein was dissolved in 100 µl of a PBS buffer, and incubated overnight at 4° C. to thus coat a half-well size ELISA plate (Corning, 3690) therewith. The next day, the buffer was replaced with about 170 µl of a PBS buffer containing 3% BSA, followed by a blocking reaction through incubation at 37° C. for about 1 hour.
5) 50 µl of the supernatant resulting from periplasmic component extraction and 50 µl of PBS were incubated at room temperature for about 1 hour so that the antibody fragments were able to bind to the coated antigen protein, followed by washing 2-3 times. A PBS buffer containing anti-myc-HRP or anti-HA-HRP secondary antibodies was dispensed, followed by incubation at room temperature for about 1 hour and then washing 2-3 times with a PBS buffer.
6) 100 µl of an ELISA reaction solution containing tetramethylbenzidine (TMB), which is the substrate of HRP, was dispensed each time, and the binding of the antibody fragment to the PD-L1 antigen was determined by observing the color reaction.
7) A FACS experiment was performed in order to verify the binding of the selected antibody fragments to the native conformation of PD-L1 expressed on the surface of cells. To this end, the PD-L1 antigen protein was expressed in 293T cells through transfection, after which binding of the antibody fragments to the surface-expressed PD-L1 antigen was determined through flow cytometry, and the experimental procedure was performed according to the general FACS experimental method.
8) 293T cells introduced with the PD-L1 protein expression vector were divided so as to obtain about $5\times10^5$ to $1\times10^6$ cells/100 µl, dispensed in a 96-well V-bottom plate, subjected to a blocking reaction, and allowed to react with 100 µl of a mixed solution of the periplasmic component containing the PD-L1 antibody fragment with a PBS buffer at 1:1 at 4° C. (or on ice) for about 30 to 60 minutes, thus inducing binding of the antibody fragment to the antigen protein. Thereafter, unbound components were removed through centrifugation (1,000 rpm for 1 minute at 4° C.), washing was performed with a FACS buffer, and the resulting cells were resuspended in a FACS buffer containing a 1:400 dilution of anti-tag-Alexa Fluor 488 secondary antibodies, followed by reaction at 4° C. for an additional 30 to 60 minutes. Thereafter, unbound components were removed through centrifugation (1,000 rpm, 1 minute, 4° C.), the fluorescently labeled cells were resuspended in 400 to 700 µl of a FACS buffer, and the presence or absence of fluorescence staining of the cells was analyzed using a FACSCalibur (Becton Dickinson) flow cytometer.

As shown in FIG. 1, the periplasmic component was obtained from about 1800 colonies derived from the 3$^{rd}$ and 4$^{th}$ elutions of the PD-L1 protein panning experiment, an ELISA reaction was carried out in order to verify binding thereof to the PD-L1 antigen protein coated on the 96-well plate, and the clones exhibiting color reaction were subjected to sequencing. As a result, about 72 individual antibody clones were obtained.

As shown in FIG. 2, based on the results of FACS on 293T cells introduced with the PD-L1 protein in order to verify the ability of the native conformation of these 72 individual clones to bind to the PD-L1 protein, a number of antibodies were found to bind to the surface of the cells on which the PD-L1 protein was expressed.

Example 5. PD-1/PD-L1 Binding Inhibition Assay Based on BLI Technology

1) An experiment for selecting a functional antibody was conducted based on the principle of 'bio-layer interferometry (BLI)' using an Octet device available from Pall. Specifically, hydration of AR2G biosensors, activation of EDC/sulfo-NHS, and inactivation of unreacted functional groups using 1 M ethanolamine coated with 5 µg/ml PD-1 protein in 10 mM sodium acetate at a pH of 5, and incubation in a 1× running buffer were performed, resulting in equilibration.
2) In order to determine the effect of interfering on the interaction between the PD-L1 antigen and the PD-1 protein due to the binding of the PD-L1 antigen protein and the antibody fragment, the biosensor coated with the PD-1 protein was immersed in a well in which the PD-L1 antigen protein and the PD-L1 binding antibody (or comparative antibody) were mixed, and a mass change on the surface of the biosensor attributable to the binding of the PD-L1 antigen protein in the solution was measured.
3) The experimental results were analyzed using data analysis software provided for use with the Octet device.

As shown in FIG. 3, whether binding of the PD-L1 antigen protein in the solution to the PD-1 protein coated on the biosensor was inhibited by allowing the selected antibody to bind to PD-L1 through sequential reaction of the selected scFv antibody and PD-L1-Fc after binding of the PD-1-Fc protein to the Octet biosensor was evaluated.

The binding inhibitory performance of individual antibody candidates having different heavy-chain and light-chain variable regions was measured using the Octet device, and thus, when the antibody fragments were incubated together, about 50 or more antibody candidates (among a total of 72 candidate antibodies) exhibiting a characteristic in that the increase in the sensorgram pattern due to the decrease in PD-L1 binding was decreased were identified.

Example 6: IgG Conversion

1) The variable regions VH and VL of about 58 individual antibodies were subjected to PCR amplification using a set of human antibody primers for amplifying the VH and VL regions of individual antibodies, identified through sequencing of individual antibody clones, followed by purification.
2) The VH fragments were treated with KpnI or BamHI, and NheI restriction enzymes, purified, and inserted into the corresponding restriction enzyme site of the pCEP4-VH vector for heavy-chain expression, and the VL fragments were treated with KpnI or BamHI, and BsiWI restriction enzymes, purified, and inserted into the corresponding restriction enzyme site of the pCEP4-VL vector for light-chain expression, thus obtaining vectors capable of expressing individual antibodies in animal cells (58 types of each of heavy-chain and light-chain expression vectors).
3) Each vector was purified using a DNA Maxi-prep kit available from QIAGEN LLC, and FREESTYLE™ 293-F cells (Thermo Fisher Scientific Inc.) were transfected therewith using a FECTOPRO® transfection reagent available from Polyplus (Sartorius Group), thus expressing individual antibodies. After culture, the resulting supernatant was subjected to an affinity purification process using a protein A resin to purify the antibody protein.
4) In order to serve as a control antibody, the heavy-chain and light-chain variable region amino acids of MK3475, which is a PD-1 target antibody developed by Merck & Co., Inc., and MPDL3280A, which is a PD-L1 target antibody developed by Genentech, Inc., were identified in respective patents, cDNA was synthesized and inserted into the pCEP4-VH vector and the pCEP4-VL vector to prepare expression vectors, and the same procedures as for the candidate antibodies were performed, whereby the two antibodies were produced, purified, and used as control antibodies.

TABLE 4

Heavy-chain and light-chain variable region amino acid sequences of MK3475 and MPDL3280A antibodies

| Antibody name | Sequence | No. |
|---|---|---|
| MPDL3280A VH-CH1-hinge-CH2-CH3 | EVQLVESGGGLVQPGGSLRLSCAASGFTFSDSWIHWVRQASEQ PGKGLEWVAWISPYGGSTYYADSVKGRFTISADTSKNTAY LQMNSLRAEDTAVYYCARRHWPGGFDYWGQGTLVTVSSAS TKGPSVFPLAPSSKSTSGGTAALGCLVKDYFPEPVTVSWN SGALTSGVHTFPAVLQSSGLYSLSSVVTVPSSSLGTQTYI CNVNHKPSNTKVDKKVEPKSCDKTHTCPPCPAPELLGGPS VFLFPPKPKDTLMISRTPEVTCVVVDVSHEDPEVKFNWYV DGVEVHNAKTKPREEQYNSTYRVVSVLTVLHQDWLNGKEY KCKVSNKALPAPIEKTISKAKGQPREPQVYTLPPSRDELT KNQVSLTCLVKGFYPSDIAVEWESNGQPENNYKTTPPVLD SDGSFFLYSKLTVDKSRWQQGNVFSCSVMHEALHNHYTQK SLSLSPGK | ID NO: 17 |

TABLE 4-continued

Heavy-chain and light-chain variable region amino acid sequences of MK3475 and MPDL3280A antibodies

| Antibody name | Sequence | No. |
|---|---|---|
| MPDL3280A VL-Ck | DIQMTQSPSSLSASVGDRVTITCRASQDVSTAVAWYQQKPSEQ GKAPKLLIYSASFLYSGVPSRFSGSGSGTDFTLTISSLQP EDFATYYCQQYLYHPATFGQGTKVEIKRTVAAPSVFIFPP SDEQLKSGTASVVCLLNNFYPREAKVQWKVDNALQSGNSQ ESVTEQDSKDSTYSLSSTLTLSKADYEKHKVYACEVTHQG LSSPVTKSFNRGEC | SEQ ID NO: 18 |
| MK3475 VH-CH1-hinge-CH2-CH3 | QVQLVQSGVEVKKPGASVKVSCKASGYTFTNYYMYWVRQASEQ PGQGLEWMGGINPSNGGTNFNEKFKNRVTLTTDSSTTTAY MELKSLQFDDTAVYYCARRDYRFDMGFDYWGQGTTVTVSS ASTKGPSVFPLAPSSKSTSGGTAALGCLVKDYFPEPVTVS WNSGALTSGVHTFPAVLQSSGLYSLSSVVTVPSSSLGTQT YICNVNHKPSNTKVDKKVEPKSCDKTHTCPPCPAPELLGG PSVFLFPPKPKDTLMISRTPEVTCVVVDVSHEDPEVKFNW YVDGVEVHNAKTKPREEQYNSTYRVVSVLTVLHQDWLNGK EYKCKVSNKALPAPIEKTISKAKGQPREPQVYTLPPSRDE LTKNQVSLTCLVKGFYPSDIAVEWESNGQPENNYKTTPPV LDSDGSFFLYSKLTVDKSRWQQGNVFSCSVMHEALHNHYT QKSLSLSPGK | SEQ ID NO: 19 |
| MK3475 VL-Ck | EIVLTQSPATLSLSPGERATLSCRASKGVSTSGYSYLHWYSEQ QQKPGQAPRLLIYLASYLESGVPARFSGSGSGTDFTLTIS SLEPEDFAVYYCQHSRDLPLTFGGGTKVEIKRTVAAPSVF IFPPSDEQLKSGTASVVCLLNNFYPREAKVQWKVDNALQS GNSQESVTEQDSKDSTYSLSSTLTLSKADYEKHKVYACEV THQGLSSPVTKSFNRGEC | SEQ ID NO: 20 |

Example 7. Mouse PD-L1 Binding FACS Assay

1) 'MC38' ($5\times10^6$ cells/10 ml) cells from a murine colon cancer cell line expressing mouse PD-L1 were treated with 100 ng/ml IFN-γ and cultured for about 48 hours to increase the expression level of PD-L1 on the surface of the cancer cell line.
2) After culture, the MC38 cells were divided so as to obtain about $5\times10^5$ to $1\times10^6$ cells/100 μl and dispensed in a 96-well V-bottom plate, followed by a blocking reaction according to the general FACS experimental method, after which the purified PD-L1 antibodies were allowed to react at a concentration of 10 μg/ml at 4° C. (or on ice) for about 30 to 60 minutes, after which unbound antibodies were washed and removed using a FACS wash buffer through centrifugation (1,000 rpm for 1 minute at 4° C.).
3) The antibody-bound cells were resuspended in a FACS buffer containing a 1:400 dilution of goat α-human Alexa Fluor 488 secondary antibodies and then allowed to react at 4° C. for about 30 to 60 minutes. Thereafter, unbound secondary antibodies were washed with a FACS wash buffer through centrifugation (1,000 rpm for 1 minute at 4° C.).
4) The cells were resuspended in 400 to 700 μl of a FACS buffer, after which the presence or absence of fluorescence staining of the cells was analyzed using a FACSCalibur (Becton Dickinson) flow cytometer, so the ability of the primary antibodies to bind to the surface of the mouse PD-L1 protein was confirmed.

As shown in FIG. 4, based on the results confirming the ability to bind to the surface of MC38 cells expressing mouse PD-L1 using the candidate antibodies expressed and purified in the form of IgG through FACS, a large number of antibodies were found to exhibit the ability to bind to mouse PD-L1. In particular, it was confirmed that KL001 (PL110) and PL112 antibodies had very strong binding ability.

Example 8. PD-1/PD-L1 Binding Blockade Assay

1) Various experimental methods are known as in-vitro cell-based efficacy verification methods for confirming the binding inhibitory performance of a PD-1 immune checkpoint protein and a PD-L1 protein as a ligand thereof, but the PD-L1 performance inhibition ability of the selected antibody clones was verified using the 'PD-1/PD-L1 Blockade Bioassay', which is a cell-based assay kit provided by Promega Corporation, and in Promega Corporation's PD-1/PD-L1 Blockade Bioassay kit, the intensity of the luminescence value measured for the cells was proportional to the intensity of the PD-1/PD-L1 binding inhibitory performance.
2) The experiment was conducted according to the protocol provided in Promega Corporation's PD-1/PD-L1 Blockade Bioassay kit, and is briefly summarized below.
3) One day before the assay, 'thaw-and-use PD-L1 cells' were thawed in a water bath at 37° C., added to a cell recovery medium, and mixed with gentle stirring, after which about 100 μl thereof was dispensed each time into a white-bottomed assay plate using a multi-channel pipette, followed by overnight incubation.
4) On the day of the assay, the supernatant was decanted, and samples for efficacy evaluation, namely serially diluted solution, comparative antibody, and candidate antibody samples, were added in a 40 μl solution volume into each well, after which thaw-and-use PD1 effector cells (CS187105) were taken out of a freezer, thawed in a water bath at 37° C., and carefully suspended in an assay buffer, and 40 µl thereof was dispensed into each well treated with the antibody sample.

5) The activation-inhibition reaction of Jurkat cells (PD-1 effector cells) was allowed to occur in a $CO_2$ incubator at 37° C. for 6 hours, and 80 µl of a Bio-Glo luciferase assay solution containing a luciferase substrate, which was heated until warm, was placed in each well, and the luminescence value was measured using a VICTOR multilabel plate reader (Perkin Elmer).

As shown in FIG. 5, based on the results of the in-vitro PD-1/PD-L1 blockade bioassay by Promega Corporation on 58 PD-L1-binding antibodies purified in the form of IgG, it was confirmed that candidate clones having strong PD-1/PD-L1 binding inhibitory performance similar to the PD-1 target antibody (MK3475 antibody) and the PD-L1 target antibody (MPDL3280A antibody) used as the control antibodies were discovered.

The PD-1/PD-L1 binding inhibitory performance of the candidate antibodies was taken as a value relative to 100% inhibitory performance of the MK3475 antibody, and the #50 clone and the KL001 clone exhibited 91% and 89% inhibitory performance, respectively. The KL001 clone showed cross-reactivity to the human-mouse PD-L1 antigen, and the #50 clone showed a characteristic of binding only to human PD-L1, and these clones were respectively designated with the development candidate codenames KL001 and KL002.

Example 9. In-Vivo MC38/C57BL/6 Syngeneic Mouse Model Study

1) Murine colon cancer MC38 cells were cultured in a medium supplemented with 10% fetal bovine serum at 37° C. and 5% $CO_2$ for about 1 week, and the morphology, viability, doubling time, and *mycoplasma* contamination thereof were checked. Uncontaminated cancer cells in a normal state were prepared for use in animal experiments, and when injected into experimental animals, cells with a cell viability of 95% or more were used.

2) The MC38 cells were harvested using trypsin-EDTA and suspended at a concentration of $1\times10^7$ cells/ml in cold PBS for transplantation, and the cell suspension thus prepared was subcutaneously injected in an amount of $5\times10^5$ cells/50 µl into the right hind leg of C57BL/6 mice using a syringe for transplantation. Thereafter, the tumor formation and growth were periodically observed, and the tumor volume was calculated by substituting the measured tumor lengths into the following equation.

[Tumor volume=$(a^2b)/2$; a=the short length of the tumor, b=the long length of the tumor]

3) When the tumor size reached 80 mm³±20, the mice were reclassified depending on the volume and grouped into control groups (a PBS treatment group and a comparative antibody treatment group) and 4 types of PD-L1 target antibody treatment groups, about 200 µg/200 µl of the antibody sample was administered through intraperitoneal injection, and the injection cycle was set to 3 times (1 day, 4 days, and 7 days) at intervals of 3 days after the first injection.

4) The growth of cancer tissue was measured every 3 days before the start of treatment with the antibody sample and every 2 days after the start of treatment, and a tumor growth curve was created with the tumor volume from the start date of treatment with the antibody sample to the end of the experiment (for about 2 weeks) and prepared to be used as validation data for antibody efficacy evaluation. When the tumor volume reached the limit determined by the Institutional Animal Care and Use Committee (IACUC), the corresponding animals were euthanized. At the end of the experiment, the mice were euthanized, the tumor was excised, the tumor was weighed, and the shape of the tumor was photographed.

5) In order to compare the in-vivo anticancer performance of antibodies showing high inhibitory performance and antibodies showing medium performance in the in-vitro efficacy evaluation test, an in-vivo efficacy evaluation experiment was performed using the four types of antibodies, #50 (=KL002), KL001 (PL110), #8 and #61 and the control antibody MPDL3280A.

As shown in FIG. 6, based on the results of analysis of the in-vivo anticancer performance of the candidate antibodies using the mouse-derived colon cancer cell line MC38 and the C57BL/6 syngeneic mouse model, the KL001 (PL110) antibody candidate having human-mouse cross-reactivity exhibited excellent anticancer efficacy, and the #50 (=KL002) antibody binding only to human PD-L1 exhibited no anticancer efficacy.

Also, for the clones #8 and #61, which did not show high performance in the in-vitro efficacy experiment, the in-vivo anticancer efficacy performance was not comparatively high.

Example 10. Ex-Vivo Immunoregulatory Activity Test of KL001 Antibody

1) In order to verify the ex-vivo efficacy of candidate antibodies on the interaction between immune cells in the blood by confirming whether immune activity may be enhanced by the binding of the PD-L1 target candidate antibody in the immune activity limitation phenomenon due to PD-1/PD-L1 binding induced in immune activation conditions between immune cells in the human body, peripheral blood mononuclear cells (PBMCs) were isolated from human blood, PBMCs stimulated with superantigens, SEA, or SEB were treated with immune anticancer antibodies, and changes in activity between immune cells were measured.

2) After obtaining approval from the Institutional Review Board (IRB) of the Blood Management Headquarters of the Korean Red Cross, a red blood cell concentrate (cRBC) was purchased from the Gangwon Blood Center, diluted at 1:1 with PBS, and centrifuged on a Ficoll-Paque, so red blood cells (RBC), peripheral blood mononuclear cells (PBMC), and plasma were separated depending on the specific gravity of the cells, and the PBMC portion was extracted and used for the experiment.

3) The separated peripheral blood mononuclear cells (PBMC) were dispensed at $1\times10^5$ cells/100 µl into 96 wells (u-bottom), after which each well was treated with 0.003 µg/100 µl of SEB (Staphylococcal enterotoxin B, super-antigen, Toxin Technology), and then with 10 µg/ml of each of the experimental group and control group antibodies to create conditions for activating immune cells. After 96 hours, the amount of IL-2 generated due to the activation of immune cells in the cell culture media was quantified using an IL-2

ELISA kit, thereby verifying the immunoregulatory activity of the candidate antibodies against human immune cells.

As shown in FIGS. 7 and 8, in the immune cell activation test through the SEB assay, it was confirmed that random crosslinking between APCs and T cells occurred during SEB treatment and that the immune cell activity was increased, and thus IL-2 secretion was increased. The immune cell activation ability of the previously selected candidate antibody (KL001) was confirmed (the figure shows the average of five experiments), and the KL001-13 candidate antibody selected after affinity maturation of the candidate antibodies was also confirmed to exhibit similar ability to regulate immune cell activity.

TABLE 5

Sequence of candidate antibody

| Antibody name | Item | SEQUENCE | SEQ ID NO |
|---|---|---|---|
| KL001 (PL110) | Heavy chain CDR1 | GGTFSSYA | 1 |
| | Heavy chain CDR2 | IIPILGIA | 2 |
| | Heavy chain CDR3 | ARSGYSYAYGSFDY | 3 |
| | VH | QVQLVESGAEVKKPGSSVKVSCKASGGT FSSYAISWVRQAPGQGLEWMGRIIPILG IANYAQKFQGRVTVTADKSTSTAYMELS SLRSEDTAVYYCARSGYSYAYGSFDYWG QGTLVTVSS | 4 |
| | Light chain CDR1 | GPTIGAGYD | 5 |
| | Light chain CDR2 | GNL | 6 |
| | Light chain CDR3 | QSYDSRLGVV | 7 |
| | VL | QLVLTQPPSVSGAPGQTVTISCTGPTIG AGYDVHWYQQLPGAAPKLLIYGNLNRPS GVPDRFSGSKSGTSASLAITDLQAEDEA DYYCQSYDSRLGVVFGGGTKLTVL | 8 |
| | VH-CH1-hinge-CH2-CH3 | QVQLVESGAEVKKPGSSVKVSCKASGGT FSSYAISWVRQAPGQGLEWMGRIIPILG IANYAQKFQGRVTVTADKSTSTAYMELS SLRSEDTAVYYCARSGYSYAYGSFDWGQ GTLVTVSSASTKGPSVFPLAPSSKSTSG GTAALGCLVKDYFPEPVTVSWNSGALTS GVHTFPAVLQSSGLYSLSSVVTVPSSSL GTQTYICNVNHKPSNTKVDKKVEPKSCD KTHTCPPCPAPELLGGPSVFLFPPKPKD TLMISRTPEVTCVVVDVSHEDPEVKFNW YVDGVEVHNAKTKPREEQYNSTYRVVSV LTVLHQDWLNGKEYKCKVSNKALPAPIE KTISKAKGQPREPQVYTLPPSRDELTKN QVSLTCLVKGFYPSDIAVEWESNGQPEN NYKTTPPVLDSDGSFFLYSKLTVDKSRW QQGNVFSCSVMHEALHNHYTQKSLSLSP GK | 9 |
| | VL-Cκ | QLVLTQPPSVSGAPGQTVTISCTGPTIG AGYDVHWYQQLPGAAPKLLIYGNLNRPS GVPDRFSGSKSGTSASLAITDLQAEDE ADYYCQSYDSRLGVVFGGGTKLTVLRTV AAPSVFIFPPSDEQLKSGTASVVCLLNN FYPREAKVQWKVDNALQSGNSQESVTEQ DSKDSTYSLSSTLTLSKADYEKHKVYAC EVTHQGLSSPVTKSFNRGEC | 10 |
| KL001-13 | Heavy chain CDR1 | GGTFSSYA | 1 |
| | Heavy chain CDR2 | IIPILGIA | 2 |
| | Heavy chain CDR3 | ARSGYSYAYGSFDY | 11 |
| | VH | QVQLVESGAEVKKPGSSVKVSCKASGGT FSSYAISWVRQAPGQGLEWMGRIIPILG IANYAQKFQGRVTVTADKSTSTAYMELS SLRSEDTAVYYCARSGYSYAYGSFDYWG QGTLVTVSS | 12 |
| | Light chain CDR1 | GPTIGAGYD | 13 |
| | Light chain CDR2 | GNL | 6 |
| | Light chain CDR3 | QSYDSRLGVV | 7 |
| | VL | QLVLTQPPSVSGAPGQTVTISCTGPTIG AGYDVHWYQQLPGAAPKLLIYGNLNRPS GVPDRFSGSKSGTSASLAITDLQAEDEA DYYCQSYDSRLGVVFGGGTKLTVL | 14 |
| | VH-CH1-hinge-CH2-CH3 | QVQLVESGAEVKKPGSSVKVSCKASGGT FSSYAISWVRQAPGQGLEWMGRIIPILG IANYAQKFQGRVTVTADKSTSTAYMELS SLRSEDTAVYYCARSGYSYAYGSFDWGQ GTLVTVSSASTKGPSVFPLAPSSKSTSG GTAALGCLVKDYFPEPVTVSWNSGALTS GVHTFPAVLQSSGLYSLSSVVTVPSSSL GTQTYICNVNHKPSNTKVDKKVEPKSCD KTHTCPPCPAPELLGGPSVFLFPPKPKD TLMISRTPEVTCVVVDVSHEDPEVKFNW YVDGVEVHNAKTKPREEQYNSTYRVVSV LTVLHQDWLNGKEYKCKVSNKALPAPIE KTISKAKGQPREPQVYTLPPSRDELTKN QVSLTCLVKGFYPSDIAVEWESNGQPEN NYKTTPPVLDSDGSFFLYSKLTVDKSRW QQGNVFSCSVMHEALHNHYTQKSLSLSP GK | 15 |
| | VL-Cκ | QLVLTQPPSVSGAPGQTVTISCTGQTIG AGYDVHWYQQLPGAAPKLLIYGNLNRPS GVPDRFSGSKSGTSASLAITDLQAEDEA DYYCQSYDSRLGVVFGGGTKLTVLRTVA APSVFIFPPSDEQLKSGTASVVCLLNNF YPREAKVQWKVDNALQSGNSQESVTEQD SKDSTYSLSSTLTLSKADYEKHKVYACE VTHQGLSSPVTKSFNRGEC | 16 |

TABLE 5-continued

Sequence of candidate antibody

| Antibody name | Item | SEQUENCE | SEQ ID NO |
|---|---|---|---|
| | VL-C$_\lambda$ | QLVLTQPPSVSGAPGQTVTISCTGQTIG AGYDVHWYQQLPGAAPKLLIYGNLNRPS GVPDRFSGSKSGTSASLAITDLQAEDEA DYYCQSYDSRLGVVFGGGTKLTVLGQPK AAPSVTLFPPSSEELQANKATLVCLISD FYPGAVTVAWKADSSPVKAGVETTTPSK QSNNKYAASSYLSLTPEQWKSHRSYSCQ VTHEGSTVEKTVAPTECS | 21 |

Example 11. Affinity Maturation Experiment

1) A focused mutagenesis library was constructed by intensively introducing mutagenesis in the heavy-chain CDR 2 and 3 regions and the light-chain CDR 1 and 3 regions in the basic backbone of the KL001 antibody.
2) The fragments in which mutagenesis was introduced to the VH and VL regions of the KL001 clone were amplified as inserts for library construction using extension PCR, the KL001 fragment was treated with a restriction enzyme for cloning into a phage display vector 'pComb3XSS', and a ligation reaction was carried out on the vector treated with the same restriction enzyme.
3) The ligated pComb3X phage display vector and the insert were transformed into electroporation competent cells, produced using ER2738 cells, to construct a KL001 antibody display mutant library.
4) Using a VCSM13 helper phage, phages displaying KL001 mutant antibodies were produced and then purified through a precipitation process using PEG and NaCl.
5) Using the biotinylated PD-L1-Fc antigen, 3-4 panning rounds were performed, and the colonies obtained from the 3$^{rd}$ and 4$^{th}$ panning rounds were used for an ELISA reaction for affinity improvement antibody selection.
6) The selected antibody fragments were expressed in the periplasm using IPTG, periplasmic fractions were obtained using sucrose, and then antibody candidates expected to show increased binding ability were selected through ELISA using a plate coated with the PD-L1 antigen.
7) The selection of candidate antibodies having increased binding ability was completed using competitive ELISA.

As shown in FIG. 9, the focused mutagenesis DNA fragments resulting from introduction of site-directed mutagenesis in the heavy-chain CDR 2 and 3 regions and the light-chain CDR 1 and 3 regions of the KL001 antibody were linked through overlap PCR to prepare a Fab-type antibody backbone, which was then inserted into the SfiI restriction enzyme site of the phage display vector 'pComb3XSS' through ligation and transformed into E. coli ER2738 cells for phage display through electroporation, thereby constructing a '1.3×10$^9$'-sized KL001 antibody display mutant library. In order to enrich the antibody clones, having strong binding ability using the biotinylated PD-L1-Fc antigen, 3-4 panning rounds were performed under stringent experimental conditions in a manner such that the amount of the antigen was decreased. Here, it was confirmed from the input versus output measurement results of panning that the amounts of strong binders were effectively increased through panning.

As shown in FIG. 10, the periplasmic fractions were obtained from about 1600 individual colonies (set1 to set16) resulting from the 3$^{rd}$ and 4$^{th}$ panning rounds, an ELISA reaction for affinity improvement antibody selection was performed, and candidate clones showing a positive signal were primarily selected (about 130 clones).

Competitive ELISA was performed in order to determine whether the antigen-binding ability was improved (or whether the Koff value was improved), incubation was carried out for an additional about 4 hours in a solution containing the PD-L1 antigen protein, and antibody clones maintaining binding were confirmed, so about 27 types of antibody candidates that were strongly bound to the PD-L1 coated on the plate compared to KL001 were identified (the original antibody KL001, which is a comparative group, showed an ELISA value of '0.278', and the affinity improvement antibodies were identified as clones representing values higher than that).

As is apparent from Table 6 below, the amino acid sequences of antibodies into which different mutations were introduced were identified through sequencing of all of the antibodies expected to show increased binding ability.

In Table 6, the sequence GPTIGAGYD in all instances is SEQ ID NO: 5, the sequence GNL in all instances is SEQ ID NO: 6, the sequence QSYDSRLGVV in all instances is SEQ ID NO: 7, the sequence GGTFSSYA in all instances is SEQ ID NO: 1, and the sequence IIPILGIA in all instances is SEQ ID NO: 2.

TABLE 6

| | Light Chain | | | Heavy Chain | | |
|---|---|---|---|---|---|---|
| Clone | LCDR1 | LCDR2 | LCDR1 | HCDR1 | HCDR2 | HCDR3 |
| PL110 (KL001) | GPTIGAGYD (SEQ ID No: 5) | GNL (SEQ ID No: 6) | QSYDSRLGV V (SEQ ID No: 7) | GGTFSSYA (SEQ ID No: 1) | IIPILGIA (SEQ ID No: 2) | ARSGYSYAYGSF DY (SEQ ID No: 3) |
| KL001-01 | GPTIGAGYD | GNL | QSYD<u>RT</u>LGV V (SEQ ID No: 42) | GGTFSSYA | IIPILGIA | A<u>Q</u>SGYGYAYGSF DY (SEQ ID No: 63) |
| KL001-02 | GPTIG<u>Q</u>GYD (SEQ ID No: 31) | GNL | QSYDSRLGV V | GGTFSSYA | IIPILGIA | ARSG<u>H</u>GYAYGSF DY (SEQ ID No: 64) |

TABLE 6-continued

| | Light Chain | | | Heavy Chain | | |
|---|---|---|---|---|---|---|
| Clone | LCDR1 | LCDR2 | LCDR1 | HCDR1 | HCDR2 | HCDR3 |
| KL001-03 | GPTIGAGYD | GNL | QSYDSTQGV (SEQ ID No: 43) | GGTFSSYA | IIPILGIA | ARSGPGYAYGSFDY (SEQ ID No: 65) |
| KL001-04 | GPTIGAGYD | GNL | QSYDSTLGV (SEQ ID No: 44) | GGTFSSYA | IIPILGIA | ARSGYGYAYGSFAA (SEQ ID No: 66) |
| KL001-05 | GPTIGAGYD | GNL | QSYDSRLGV | GGTFSSYA | IIPILGIA | ARSGYGYAYGSFDM (SEQ ID No: 67) |
| KL001-06 | GPTIGAGYD | GNL | QSYDSRLGV | GGTFSSYA | IIPILGIA | ARSGYGYAYGSFDV (SEQ ID No: 68) |
| KL001-07 | GPTIGAGYD | GNL | QSYDSRLGV | GGTFSSYA | QIPILGIA (SEQ ID No: 56) | ARSGYGYAYGSFDY (SEQ ID No: 69) |
| KL001-08 | GPTIGAGYD | GNL | QSYDSTHGV (SEQ ID No: 45) | GGTFSGYA (SEQ ID No: 55) | IIPALGIA (SEQ ID No: 57) | ARSGYGYAYGSFDY (SEQ ID No: 70) |
| KL001-09 | GPPIGAGYD (SEQ ID No: 32) | GNL | QSYDSTPGV (SEQ ID No: 46) | GGTFSSYA | IIPILQIA (SEQ ID No: 58) | ARSGYGYAYGSFDY (SEQ ID No: 71) |
| KL001-10 | GPTIGAGYD | GNL | QSYDQTLGV (SEQ ID No: 47) | GGTFSSYA | IIPILGIA | ARSGYGYAYGSFDY (SEQ ID No: 72) |
| KL001-11 | GPTIGAGYD | GNL | QSYDRTLGV (SEQ ID No: 48) | GGTFSSYA | IIPILGIA | ARSGYGYAYGSFDY (SEQ ID No: 73) |
| KL001-12 | GPTIGAGYD | GNL | QSYDSALGV (SEQ ID No: 49) | GGTFSSYA | IIPILGIA | ARSGYGYAYGSFDY (SEQ ID No: 74) |
| KL001-13 | GQTIGAGYD (SEQ ID No: 33) | GNL | QSYDSRLGV | GGTFSSYA | IIPILGIA | ARSGYGYAYGSFDY (SEQ ID No: 75) |
| KL001-14 | GPQIGAGYD (SEQ ID No: 34) | GNL | QSYDSRLGV | GGTFSSYA | IIPILGIA | ARSGYGYAYQSFDY (SEQ ID No: 76) |
| KL001-15 | GPTIQAGYD (SEQ ID No: 35) | GNL | QSYDSRLGV | GGTFSSYA | IIPILGIA | ARSGYGYAYGSFDY (SEQ ID No: 77) |
| KL001-16 | GPTIGAGYD | GNL | QSYDSRLGV | GGTFSSYA | IIPILGIA | ARSGYGYAYGSFDY (SEQ ID No: 78) |
| KL001-17 | GPVIGAGYD (SEQ ID No: 36) | GNL | QSYDSRLGV | GGTFSSYA | IIPILGIA | ARSGYGYAYGSFDY (SEQ ID No: 79) |
| KL001-18 | GQTIGAGYD (SEQ ID No: 37) | GNL | QSYDSTEGV (SEQ ID No: 50) | GGTFSSYA | IIPILGIA | ARSGYGYAYGSFDY (SEQ ID No: 80) |
| KL001-19 | GPTIGAGYD | GNL | QSYDSTVGV (SEQ ID No: 51) | GGTFSSYA | IIPILGIA | ARSGYGYAYGSFDY (SEQ ID No: 81) |
| KL001-20 | GPTIGAGYD | GNL | QSYDSTLGV (SEQ ID No: 44) | GGTFSSYA | IIPIMGIA (SEQ ID No: 59) | ARSGYGYAYGSFDY (SEQ ID No: 82) |
| KL001-21 | GPTIGAGYD | GNL | QAYDSTLGV (SEQ ID No: 52) | GGTFSSYA | IIPVLGIA (SEQ ID No: 60) | ARSGYGYAYGSFDY (SEQ ID No: 83) |

TABLE 6-continued

| | Light Chain | | | Heavy Chain | | |
|---|---|---|---|---|---|---|
| Clone | LCDR1 | LCDR2 | LCDR1 | HCDR1 | HCDR2 | HCDR3 |
| KL001-22 | GPTIGAGYD | GNL | QSYDSTLGV V (SEQ ID No: 44) | GGTFSSYA (SEQ ID No: 61) | ISPILGIA DY | ARSGYGYAYGSF (SEQ ID No: 84) |
| KL001-23 | GPTIGAGYD | GNL | QSYDSRLGV V | GGTFSSYA | IIPILGIA DH | ARSGYGYAYGVF (SEQ ID No: 85) |
| KL001-24 | GPTIGAGFD (SEQ ID No: 38) | GNL | QSYDSRLGV V | GGTFSSYA | IIPILGQA (SEQ ID No: 62) | ARSGYGYAYGSF DY |
| KL001-25 | QPTIGAGYD (SEQ ID No: 39) | GNL | QSMDSTLGV V (SEQ ID No: 53) | GGTFSSYA | IIPILGIA | ARSGYGYAYGSF DY |
| KL001-26 | GPTIGQGYD (SEQ ID No: 40) | GNL | QSYDSRLGV V | GGTFSSYA | IIPILGIA | ARSGYGYAYGSF DY |
| KL001-27 | GQTIGAGYD (SEQ ID No: 41) | GNL | QSYDSTDGV V (SEQ ID No: 54) | GGTFSSYA | IIPILGIA | ARSGYGYAYGSF DY |

In order to measure the ability of the affinity improvement antibodies to interfere with the interaction between the PD-L1 antigen and the PD-1 protein due to the binding of the PD-L1 antigen protein and the antibody fragment, a biosensor coated with the PD-1 protein was immersed in a well in which the PD-L1 antigen protein and the PD-L1 binding antibody (or comparative antibody) were mixed, and thus a mass change on the surface of the biosensor attributable to the binding of the PD-L1 antigen protein in the solution was measured using the BLI-based Octet device mentioned in Example 5.

Table 7 below shows the results of binding ability of the affinity improvement antibodies, analyzed using data analysis software specifically provided for use with the Octet device.

TABLE 7

Binding ability of affinity improvement antibodies

| No. | Sample ID | KD (M) | $R^2$ |
|---|---|---|---|
| 1 | MPDL3280A | 2.089E-11 | 0.9978 |
| 2 | KL001(PL110) | 5.842E-11 | 0.9994 |
| 3 | KL001-02 | 2.160E-11 | 0.9987 |
| 4 | KL001-04 | 1.362E-11 | 0.9975 |
| 5 | KL001-06 | 1.686E-11 | 0.9981 |
| 6 | KL001-07 | 1.367E-11 | 0.9988 |
| 7 | KL001-08 | 1.417E-11 | 0.9991 |
| 8 | KL001-09 | 2.165E-11 | 0.9986 |
| 9 | KL001-10 | 2.007E-11 | 0.9985 |
| 10 | KL001-11 | 1.629E-11 | 0.998 |
| 11 | KL001-12 | 1.502E-11 | 0.9991 |
| 12 | KL001-13 | 4.885E-12 | 0.9988 |
| 13 | KL001-14 | 2.044E-11 | 0.9992 |
| 14 | KL001-15 | 5.798E-12 | 0.9982 |
| 15 | KL001-16 | 9.082E-12 | 0.9981 |
| 16 | KL001-17 | 1.827E-11 | 0.9989 |
| 17 | KL001-18 | 1.607E-11 | 0.9983 |
| 18 | KL001-19 | 6.552E-12 | 0.9983 |
| 19 | KL001-20 | 2.128E-11 | 0.9982 |
| 20 | KL001-21 | 2.831E-11 | 0.9986 |
| 21 | KL001-22 | 4.903E-11 | 0.9986 |
| 22 | KL001-23 | 2.674E-11 | 0.9989 |
| 23 | KL001-24 | 4.078E-11 | 0.9992 |

TABLE 7-continued

Binding ability of affinity improvement antibodies

| No. | Sample ID | KD (M) | $R^2$ |
|---|---|---|---|
| 24 | KL001-26 | 5.722E-11 | 0.9991 |
| 25 | KL001-27 | 6.117E-11 | 0.9986 |

Example 12. BIACORE™ Surface Plasmon Resonance Assay

1) In order to measure the ability of the candidate antibody to bind to the PD-L1 antigen protein, binding strength was measured using a BIACORE™ T200 device based on the principle of surface plasmon resonance (SPR).
2) In the analysis of binding affinity of the anti-PD-L1 antibody using an antibody capture method, an anti-human IgG (Fc) antibody was first immobilized on the surface of a CM5 chip using a Human Antibody Capture Kit according to the guide for the experimental method provided by the manufacturer, and the candidate antibodies KL001-8 and KL001-13 were diluted in a PBS-P running buffer, injected at a flow rate of 10 μl/min for 30 seconds, and captured at a level of 300 to 330 RU, after which the human PD-L1 antigen protein (Sino Biological) was subjected to serial 2-fold dilution from 5 nM, and association and dissociation reactions were observed at a flow rate of 30 μl/min (respective reaction times therefor were set to 4 and 7 minutes). In the measurement of the binding ability to the mouse PD-L1 antigen protein, the binding ability was measured through serial 2-fold dilution from 10 nM and association and dissociation for 4 min and 3 min, respectively, at a flow rate of 30 μl/min.
3) In order to remove the bound antibody every cycle, a regeneration solution (3 M $MgCl_2$) was injected at a flow rate of 30 μl/min for 30 seconds, and the experimental data were obtained using a 1:1 binding model of BIA evaluation software version 1.0.

4) In the experiment for analysis of the binding affinity of the anti-PD-L1 antibody using the antigen capture method, the anti-his antibody was immobilized on the surface of a CM5 chip using a His Capture Kit according to the manufacturer's instructions, the PD-L1 antigen protein was captured, the candidate antibody was subjected to serial 2-fold dilution from 2.5 nM, and the binding ability thereof was measured through association and dissociation for 4 min and 7 min, respectively, at a flow rate of 30 μl/min.

As shown in FIG. 11, the anti-human IgG (Fc) antibody was immobilized in flow cell Nos. 3 and 4. Immobilization was performed in accordance with instructions for the Human Antibody Capture Kit, indicating immobilization within the range of about 11,000 to 13,000 RU in each flow cell. The antibodies KL001-8 and KL001-13 were captured using a running buffer (PBS-P), PD-L1 was subjected to serial dilution and injected, and kinetics was measured, based on which it was confirmed that the KL001-8 antibody exhibited binding ability of KD=$6.714 \times 10^{-11}$ M to human PD-L1 and $6.401 \times 10^{-9}$ M to mouse PD-L1, and the KL001-13 antibody exhibited binding ability of about KD=$6.320 \times 10^{-11}$ M to human PD-L1 and $2.797 \times 10^{-9}$ M to mouse PD-L1.

Example 13. Evaluation of Anticancer Efficacy Through Single Treatment Using In-Vivo Syngeneic Mouse Model The anticancer efficacy of antibody candidates was confirmed using an in-vivo syngeneic mouse model.

As shown in FIG. 12, two types of performance-optimizing antibodies and the MPDL3280A antibody were i.p. administered in the MC38 subcutaneous syngeneic mouse model, and the tumor growth inhibitory efficacy thereof was evaluated. Relative to the control group administered with PBS, the MPDL3280A group showed 94.3% inhibition, the KL001 (PL110) group showed 97.5% inhibition, the binding affinity improvement antibody KL001-13 group showed 98.9% inhibition, and no change in body weight due to the drug was observed.

TABLE 8

Table showing results of TGI (% tumor growth inhibition, TGI %=$(1-(T/C)) \times 100$)

| Group | TGI (%) |
| --- | --- |
| Control | — |
| MPDL3280A | 94.3% |
| KL001(PL110) | 97.5% |
| KL001-13 | 98.9% |

Example 14. Measurement of IC50 for Verification of In-Vitro Efficacy

1) In order to confirm the in-vitro performance improvement effect of the candidate antibodies obtained through studies for improving affinity and physical properties in contrast with the comparative antibody, the IC50 value for the inhibitory effect was verified by measuring the PD-1/PD-L1 binding inhibitory ability of serially diluted candidate antibody and comparative antibody samples using a 'PD-1/PD-L1 Blockade Bioassay' kit provided by Promega Corporation.
2) The experiment was carried out according to the protocol provided in Promega Corporation's PD-1/PD-L1 Blockade Bioassay kit, and is summarized below.
3) One day before the assay, 'thaw-and-use PD-L1 cells' were thawed in a water bath at 37° C., added to a cell recovery medium, and mixed with gentle stirring, and about 100 μl thereof was dispensed each time into a white-bottomed assay plate using a multi-channel pipette, followed by overnight incubation.
4) On the day of the assay, the supernatant was decanted, and samples for efficacy evaluation, namely serially diluted solution, comparative antibody, and candidate antibody samples, were added in a 40 μl solution volume into each well, after which thaw-and-use PD1 effector cells (CS187105) were taken out of the freezer, thawed in a water bath at 37° C., and carefully suspended in an assay buffer, and 40 μl thereof was dispensed into each well treated with the antibody sample.
5) The Jurkat cell activation-inhibition reaction was allowed to occur in a $CO_2$ incubator at 37° C. for 6 hours, 80 μl of a BIO-GLO™ luciferase assay solution containing a luciferase substrate, which was heated until warm, was added to each well, and the luminescence value was measured using a VICTOR™ multi-label plate reader (Perkin Elmer).

As shown in FIG. 13, based on the results confirming the performance level of the selected antibodies by measuring the IC50 value of the selected antibody using the in-vitro cell-based assay, most of the affinity improvement antibody candidates had low IC50 concentration values compared to the comparative antibody MPDL3280A, indicative of improved ability to regulate immune activity.

TABLE 9

| IC50 measurement results | | | | | | | | |
| --- | --- | --- | --- | --- | --- | --- | --- | --- |
| Luminescence | MPDL3280A | PL110 M(D) | #13 | #15 | #19 | #16 | #4 | #7 |
| Top | 59862 | 59658 | 61558 | 58115 | 60870 | 59137 | 56657 | 58929 |
| LogIC50 | -7.054 | -7.082 | -7.166 | -7.176 | -7.216 | -7.219 | -7.293 | -7.171 |
| IC50 (g/mL) | 8.821E-08 | 8.282E-08 | 6.817E-08 | 6.663E-08 | 6.083E-08 | 6.035E-08 | 5.089E-08 | 6.75E-08 |
| Rank | | | 14 | 10 | 4 | 3 | 1 | 11 |
| Luminescence | #8 | #12 | #18 | #11 | #6 | 2-24 | #17 | #10 |
| Top | 60894 | 57414 | 60739 | 61380 | 63285 | 66538 | 67423 | 67283 |
| LogIC50 | -7.093 | -7.189 | -7.17 | -7.122 | -7.183 | -7.183 | -7.17 | -7.135 |
| IC50 (g/mL) | 8.078E-08 | 6.478E-08 | 6.764E-08 | 7.556E-08 | 6.56E-08 | 6.554E-08 | 6.761E-08 | 7.325E-08 |
| Rank | 20 | 6 | 13 | 19 | 9 | 8 | 12 | 18 |
| Luminescence | #14 | #20 | #2 | #9 | #23 | #21 | MPDL3280A-2 | PL110 M(D)-2 |
| Top | 67101 | 68842 | 60910 | 64566 | 67022 | 65912 | 66366 | 68526 |
| LogIC50 | -7.196 | -7.155 | -7.262 | -7.162 | -7.187 | -7.139 | -7.073 | -7.052 |
| IC50 (g/mL) | 6.372E-08 | 6.992E-08 | 5.476E-08 | 6.893E-08 | 6.496E-08 | 7.259E-08 | 8.45E-08 | 8.863E-08 |
| Rank | 5 | 16 | 2 | 15 | 7 | 17 | | |

Example 15. Evaluation of Anticancer Effect Through Combined Treatment In Vivo 1) In order to verify whether a synergistic effect was observed in the anticancer performance evaluation animal model when the PD-L1 immune anticancer antibody candidate was used in combination with other anticancer agents, an experiment was conducted to verify the efficacy of a representative immune activation protein, namely recombinant IL-2, a CTLA-4 antibody (9D9 clone, BioXcell), and the PD-L1 target candidate antibody (KL001-13) when used in combination.
2) For the development of combined therapy using the KL001-13 antibody, a combined treatment experiment was performed using an MC38 mouse colon cancer cell line and a 6-week-old C57BL/6 male (a) mouse model, the groups being divided into a total of 8 groups including four groups administered with PBS, IL-2, CTLA-4, and KL001-13 alone and four groups co-administered with IL-2+KL001-13, CTLA-4+KL001-13, IL-2+MPDL3280A, and CTLA-4+MPDL3280A, with 8 mice in each group (n=8).
3) The mouse colon cancer MC38 cell line was cultured at 70-90% cell density, treated with 0.25% trypsin-EDTA, harvested, and resuspended in DMEM media (serum free) at a cell concentration of $1 \times 10^6$ cells/100 µl to prepare an MC38 cell sample with cell viability ≥95%, which was then subcutaneously injected in an amount of $1 \times 10^6$ cells/100 µl into the left side of the body of C57BL/6 mice anesthetized with 2.5% avertin and allowed to grow for about 7 to 10 days in the experimental animal mice until the tumor size of the injected MC38 cell line reached 100 mm³. Here, the size of the tumor was calculated as follows.

[Tumor volume=$(a^2b)/2$; $a$=the short length of the tumor, $b$=the long length of the tumor]

4) When the size of the tumor reached 100 mm³, the prepared PBS, candidate antibody, comparative antibody, and cytokine IL-2 were intraperitoneally injected, either alone or in combination. Here, the KL001-13, MPDL3280A, and CTLA-4 antibodies were administered a total of 4 times alone or in combination at a concentration of 10 mg/kg (200 µg/100 µl) at an interval of 3 days, and IL-2 cytokine was administered a total of 5 times alone or in combination at a concentration of $1 \times 10^4$ IU/100 µl at an interval of 2 days. The tumor size (mm³) was measured 3 times a week, and the extent of growth of the tumor was observed. In the test for verifying the combined efficacy of IL-2 and the KL001-13 antibody, IL-2 is generally administered daily in animal experiments due to the short half-life of IL-2 in animals, but in the present experiment, IL-2 was administered in a small amount every 2 days in order to determine whether IL-2 as an immune activity stimulant exhibited a synergistic effect when used in combination with the PD-L1 target antibody.

As shown in FIG. 14, when IL-2 and the KL001-13 antibody were administered in combination, it could be observed that the anticancer efficacy was significantly increased compared to when IL-2 and the KL001-13 antibody were administered alone, and also that the anticancer effect thereof was superior to the combined effect of IL-2 and the MPDL3280A antibody available from Genentech, with which the comparative group was treated.

As shown in FIG. 15, based on the results of verification of the efficacy of administration of the immune checkpoint protein CTLA-4 target antibody (9D9 clone, BioXcell) and the KL001-13 antibody, either alone or in combination, a good anticancer effect was observed in the group administered with PD-L1 alone compared to the group administered with CTLA-4 antibody alone, and when these two antibodies were administered in combination, an outstanding synergistic effect was exhibited, to the extent that many cases in which cancer cells were completely killed were observed. In particular, it was observed that the combined effect of the KL001-13 antibody was superior to the combined efficacy of the CTLA-4 antibody and the MPDL3280A antibody available from Genentech used as the comparative antibody.

INDUSTRIAL APPLICABILITY

According to the present invention, it can be confirmed that the antibody binding to PD-L1 or the antigen-binding fragment thereof exhibits human-mouse, human-monkey and human-dog cross-reactivity, binds to PD-L1 with very high affinity, and inhibits the formation of a PD-1/PD-L1 complex. In addition, excellent effects can be exhibited in in-vitro cell-based assays, in-vivo efficacy experiments, and combination therapy experiments. Thereby, the antibody binding to PD-L1 or the antigen-binding fragment thereof according to the present invention can be effectively used for the prevention or treatment of cancer as desired, and can exhibit a synergistic effect when used in combination with another anticancer agent.

Although specific embodiments of the present invention have been disclosed in detail as described above, it will be obvious to those of ordinary skill in the art that the description is merely of preferable exemplary embodiments, and is not to be construed as limiting the scope of the present invention. Therefore, the substantial scope of the present invention will be defined by the appended claims and equivalents thereto.

[Sequence List Free Text]

An electronic file is attached.

The invention claimed is:

1. An antibody binding to PD-L1 or an antigen-binding fragment thereof, comprising:
a heavy-chain variable region comprising a heavy-chain CDR1 of SEQ ID NO: 1, a heavy-chain CDR2 of SEQ ID NO: 2, and a heavy-chain CDR3 of SEQ ID NO: 3, a light-chain variable region comprising a light-chain CDR1 of SEQ ID NO: 5, a light-chain CDR2 of SEQ ID NO: 6, and a light-chain CDR3 of SEQ ID NO: 7; or
a heavy-chain variable region comprising a heavy-chain CDR1 of SEQ ID NO: 1, a heavy-chain CDR2 of SEQ ID NO: 2, and a heavy-chain CDR3 of SEQ ID NO: 11, a light-chain variable region comprising a light-chain CDR1 of SEQ ID NO: 13, a light-chain CDR2 of SEQ ID NO: 6, and a light-chain CDR3 of SEQ ID NO: 7.

2. The antibody or the antigen-binding fragment thereof according to claim 1, comprising a heavy-chain variable region comprising the sequence of SEQ ID NO: 4 or SEQ ID NO: 12.

3. The antibody or the antigen-binding fragment thereof according to claim 1, comprising a light-chain variable region comprising the sequence of SEQ ID NO: 8 or SEQ ID NO: 14.

4. An antibody-drug conjugate in which a drug is conjugated to the antibody or the antigen-binding fragment thereof according to claim 1.

5. A bispecific antibody in which the antibody or the antigen-binding fragment thereof according to claim 1 is bound to an antibody binding to another antigen.

6. A nucleic acid encoding the antibody or the antigen-binding fragment thereof according to claim 1.

7. An expression vector comprising the nucleic acid according to claim 6.

8. A recombinant cell transfected with the expression vector according to claim 7.

9. A method of producing an antibody binding to PD-L1 or an antigen-binding fragment thereof, comprising:
(a) culturing the cell according to claim 8;
(b) expressing the antibody binding to PD-L1 or an antigen-binding fragment thereof by the cell by said culturing; and
(c) isolating the antibody binding to PD-L1 or an antigen-binding fragment thereof by purifying the antibody or an antigen-binding fragment thereof from the cultured cell.

10. A method for treating cancer expressing PD-L1 in a subject in need of treatment for said cancer, comprising administering the antibody or the antigen-binding fragment thereof according to claim 1 to the subject.

11. A method of combination therapy for treating cancer expressing PD-L1 in a subject in need of treatment for said cancer, comprising administering to the subject the antibody or the antigen-binding fragment thereof according to claim 1 in combination with another anticancer agent.

* * * * *

UNITED STATES PATENT AND TRADEMARK OFFICE
CERTIFICATE OF CORRECTION

PATENT NO. : 12,331,120 B2  
APPLICATION NO. : 17/441914  
DATED : June 17, 2025  
INVENTOR(S) : Dae Hee Kim et al.

Page 1 of 1

It is certified that error appears in the above-identified patent and that said Letters Patent is hereby corrected as shown below:

In the Specification

Column 12, Lines 12-13, "pLz promoter, pRz promoter" should be -- pLλ promoter, pRλ promoter --.

Column 22, Line 13, "1×PBS" should be -- 1X PBS --.

Column 24, Line 5, "1×TES" should be -- 1X TES --.

Column 24, Line 8, "0.2×TES" should be -- 0.2X TES --.

Column 41, Line 16, "male (♂)" should be -- male (♂) --.

Signed and Sealed this  
Eighteenth Day of November, 2025

John A. Squires  
*Director of the United States Patent and Trademark Office*